(12) United States Patent
Chan et al.

(10) Patent No.: US 9,714,437 B2
(45) Date of Patent: Jul. 25, 2017

(54) PRODUCTION OF FATTY ALCOHOLS FROM ENGINEERED MICROORGANISMS

(71) Applicant: Codexis, Inc., Redwood City, CA (US)

(72) Inventors: Kaman Chan, San Bruno, CA (US); Fernando Valle, Burlingame, CA (US); Yoram Barak, Greenwich, CT (US); Louis Clark, San Francisco, CA (US); Kristian Karlshoej, Naperville, IL (US); Jonathan Vroom, South San Francisco, CA (US); Jovana Nazor, Santa Clara, CA (US); Claus M Krebber, Palo Alto, CA (US); Kenneth Mitchell, Santa Clara, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 15/149,859

(22) Filed: May 9, 2016

(65) Prior Publication Data

US 2016/0244787 A1    Aug. 25, 2016

Related U.S. Application Data

(63) Continuation of application No. 14/394,817, filed as application No. PCT/US2013/037472 on Apr. 19, 2013, now abandoned, which is a continuation-in-part of application No. PCT/US2012/069444, filed on Dec. 13, 2012, and a continuation-in-part of application No. PCT/US2012/069553, filed on Dec. 13, 2012.

(60) Provisional application No. 61/636,044, filed on Apr. 20, 2012, provisional application No. 61/674,053, filed on Jul. 20, 2012.

(51) Int. Cl.
| | |
|---|---|
| *C12N 15/00* | (2006.01) |
| *C12P 7/04* | (2006.01) |
| *C12N 9/10* | (2006.01) |
| *C12N 9/16* | (2006.01) |
| *C12N 9/00* | (2006.01) |
| *A61K 8/34* | (2006.01) |
| *A61Q 19/00* | (2006.01) |
| *C07C 31/125* | (2006.01) |
| *C11D 3/20* | (2006.01) |
| *C12P 5/02* | (2006.01) |
| *C12P 7/64* | (2006.01) |
| *C12N 9/02* | (2006.01) |
| *C12N 15/70* | (2006.01) |

(52) U.S. Cl.
CPC ............... *C12P 7/04* (2013.01); *A61K 8/342* (2013.01); *A61Q 19/00* (2013.01); *C07C 31/125* (2013.01); *C11D 3/2031* (2013.01); *C12N 9/0008* (2013.01); *C12N 9/1029* (2013.01); *C12N 9/16* (2013.01); *C12N 9/93* (2013.01); *C12N 15/70* (2013.01); *C12P 5/02* (2013.01); *C12P 7/6436* (2013.01); *C12Y 203/01086* (2013.01); *C12Y 301/02* (2013.01); *C12Y 602/01003* (2013.01); *A61K 2800/10* (2013.01); *C12Y 102/0105* (2013.01); *C12Y 301/02014* (2013.01); *Y02E 50/17* (2013.01)

(58) Field of Classification Search
CPC ...................................................... C12N 15/00
See application file for complete search history.

(56) References Cited

U.S. PATENT DOCUMENTS

| | | |
|---|---|---|
| 4,356,196 A | 10/1982 | Hultquist |
| 4,461,648 A | 7/1984 | Foody |
| 4,556,430 A | 12/1985 | Converse et al. |
| 4,600,590 A | 7/1986 | Dale |
| 5,037,663 A | 8/1991 | Dale |
| 5,171,592 A | 12/1992 | Holtzapple et al. |
| 5,344,771 A | 9/1994 | Davies et al. |
| 5,512,482 A | 4/1996 | Voelker et al. |
| 5,723,761 A | 3/1998 | Voelker et al. |
| 5,910,631 A | 6/1999 | Topfer et al. |
| 5,939,544 A | 8/1999 | Karstens et al. |
| 5,955,329 A | 9/1999 | Yuan et al. |
| 6,106,888 A | 8/2000 | Dale et al. |
| 6,117,679 A | 9/2000 | Stemmer |
| 6,143,538 A | 11/2000 | Somerville et al. |
| 6,150,512 A | 11/2000 | Yuan |
| 6,176,176 B1 | 1/2001 | Dale et al. |
| 6,376,246 B1 | 4/2002 | Crameri et al. |
| 6,586,182 B1 | 7/2003 | Patten et al. |
| 7,332,311 B2 | 2/2008 | Lardizabal et al. |
| 7,465,791 B1 | 12/2008 | Hallberg et al. |
| 7,629,157 B2 | 12/2009 | Davis et al. |
| 7,754,457 B2 | 7/2010 | Foody et al. |

(Continued)

FOREIGN PATENT DOCUMENTS

| | | |
|---|---|---|
| WO | 2007/136762 A2 | 11/2007 |
| WO | 2008/119082 A2 | 10/2008 |

(Continued)

OTHER PUBLICATIONS

Altschul, S., et al., "Basic local alignment search tool," J. Mol. Biol., 215: 403-410 (1990).

(Continued)

*Primary Examiner* — Maryam Monshipouri
(74) *Attorney, Agent, or Firm* — Codexis, Inc.

(57) ABSTRACT

The invention generally relates to the production of a fatty alcohol composition from recombinant microbial cells. The fatty alcohols are produced by expressing a gene encoding a heterologous fatty alcohol forming acyl-CoA reductase ("FAR"); a gene encoding a heterologous thioesterase ("TE") gene and a gene encoding an acyl-CoA synthetase ("ACS").

8 Claims, 1 Drawing Sheet

(56) References Cited

U.S. PATENT DOCUMENTS

| | | |
|---|---|---|
| 7,783,428 B2 | 8/2010 | Gustafsson et al. |
| 8,110,670 B2 | 2/2012 | Hu et al. |
| 8,574,878 B2 | 11/2013 | Behrouzian et al. |
| 2006/0195947 A1 | 8/2006 | Davis et al. |
| 2007/0031953 A1 | 2/2007 | Dunson, Jr. et al. |
| 2008/0104724 A1 | 5/2008 | Sticklen et al. |
| 2008/0220990 A1 | 9/2008 | Fox |
| 2009/0312196 A1 | 12/2009 | Colbeck et al. |
| 2010/0203614 A1 | 8/2010 | Whalen et al. |
| 2010/0242345 A1 | 9/2010 | Keasling et al. |
| 2011/0000125 A1 | 1/2011 | McDaniel et al. |
| 2012/0009640 A1 | 1/2012 | Behrouzian et al. |

FOREIGN PATENT DOCUMENTS

| | | |
|---|---|---|
| WO | 2009/045651 A2 | 4/2009 |
| WO | 2010/075483 A2 | 7/2010 |
| WO | 2011/008535 A1 | 1/2011 |
| WO | 2011/008565 A1 | 1/2011 |
| WO | 2011/019858 A1 | 2/2011 |
| WO | 2012/006114 A2 | 1/2012 |

OTHER PUBLICATIONS

Altschul, S.F., et al., "Gapped BLAST and PSI-BLAST: a new generation of protein database search programs," Nucleic Acids Res., 25(17):3389-3402 (1997).
Archer, C.T., et al., "The genome sequence of E. coli W (ATCC 9637): comparative genome analysis and an improved genome-scale reconstruction of E. coli," BMC Genomics, 12:9[2011].
Brosius, J., et al., "Spacing of the -10 and -35 Regions in the tac Promoter," J. Biol. Chem., 260(6): 3539-3541 [1985].
Cantu, D.C., et al., "Thioesterases: a new perspective based on their primary and tertiary structures," Protein Science, 19(7):1281-1295 (2010).
Cantu, D.C., et al., "ThYme: a database for thioester-active enzymes," Nucleic Acid Research, 39:D342-D346 (2011).
Carter, P., "Site-directed mutagenesis," Biochem. J., 237:1-7 [1986].
Court, D.L., et al., "Genetic Engineering Using Homologous Recombination," Annual Rev. Genet., 36:361-388 [2002].
Datsenko, K.A., et al., "One-step inactivation of chromosomal genes in Escherichia coli K-12 using PCR products," PNAS, 97(12): 6640-6645 [2000].
Datta, S., et al., "A set of recombineering plasmids for gram-negative bacteria," Gene, 379: 109-115 (2006).
De Boer, H.A., et al., "The tac promoter: A functional hybrid derived from the trp and lac promoters," Proc. Natl Acad. Sci. USA, 80: 21-25 (1983).
Doan, T.T.P., et al., "Functional expression of five Arabidopsis fatty acyl-CoA reductase genes in Escherichia coli," J. Plant Physiol., 166: 787-796 [2009].
Dower, W.J., et al., "High efficiency transformation of E. coli by high voltage electroporation," Nucleic Acids Research, 16(13): 6127-6145 [1988].
Eblen, D.R., et al., "Studies to Select Appropriate Nonpathogenic Surrogate Escherichia coli Strains for Potential Use in Place of Escherichia coli O157:H7 and Salmonella in Pilot Plant Studies," J. of Food Protection, 68(2):282-291 [2005].
Hayashi, K., et al., "Highly accurate genome sequences of Escherichia coil K-12 strains MG1655 and W3110," Mol. Syst. Biol., 2(2006.0007):1-5 [2005].
Henikoff, S., et al., "Amino acid substitution matrices from protein blocks," Proc. Natl. Acad. Sci. USA, 89:10915-10919 [1992].
Hofvander, P., et al., "A prokaryotic acyl-CoA reductase performing reduction of fatty acyl-CoA to fatty alcohol," FEBS Letters, 585(22):3538-3543 (2011).
Ishige, T., et al., "Long-Chain Aldehyde Dehydrogenase That Participates in n-Alkane Utilization and Wax Ester Synthesis in Acinetobacter sp. Strain M-1," Appl. Environ. Microbiol., 66:3481-3486 (2000).

Jones, A., et al., "Palmitoyl-Acyl Carrier Protein (ACP) Thioesterase and the Evolutidnary-Origin of Plant ACyl-ACP Thioesterases," The Plant Cell, 7:359-371 (1995).
Kalscheuer, R., et al., "Neutral Lipid Biosynthesis in Engineered Escherichia coli: Jojoba Oil-Like Wax Esters and Fatty Acid Butyl Esters," Appl. Environ. Microbiol., 72:1373-79 [2006].
Lathe, R., et al., "Plasmid and bacteriophage vectors for excision of intact inserts," Gene, 57:193-201 [1987].
Lerner, C.G., et al., "Low copy number plasmids for regulated low-level expression of cloned genes in Escherichia coli with blue/white insert screening capability," Nucleic Acids Research, 18(15):4631 [1990].
Li, J.J., et al., "Reductions" in Modern Organic Synthesis in the Laboratory, Oxford University Press, Inc., p. 81-83 [2007].
Ling, M.M., et al., "Approaches to DNA Mutagenesis: An Overview," Anal. Biochem., 254(2):157-78 [1997].
Link, A.J., et al., "Methods for generating precise deletions and insertions in the genome of wild-type Escherichia coli: application to open reading frame characterization," J. Bact., 179: 6228-6237 [1997].
Metz, J.G., et al., "Purification of a Jojoba Embryo Fatty Acyl-Coenzyme A Reductase and Expression of Its cDNA in High Erucic Acid Rapeseed," Plant Physiol., 122:635-644 [2000].
Minshull, J., et al., "Protein evolution by molecular breeding," Curr. Op. Chem. Biol., 3:284-290 [1999].
Morgan-Kiss, R.M., et al., "The Escherichia coli fadK (ydiD) Gene Encodes an Anerobically Regulated Short Chain Acyl-CoA Synthetase," J. Biol. Chem., 279:37324-37333 [2004].
Moto, K., et al., "Pheromone gland-specific fatty-acyl reductase of the silkmoth, Bombyx mori," PNAS, 100(16):9156-9161 [2003].
Needleman, S., et al., "A general method applicable to the search for similarities in the amino acid sequence of two proteins," J. Mol. Biol. 48:443-453 (1970).
Nevoigt, E., et al., "Engineering of Promoter Replacement Cassettes for Fine-Tuning of Gene Expression in Saccharomyces cerevisiae," Appl. Environ. Microbiol., 72:5266-5273 (2006).
Notredame, C., et al., "T-COFFEE: A novel method for multiple sequence alignments," JMB, 302:205-217, [2000].
Orosz, A., et al., "Analysis of the complex transcription termination region of the Escherichia coli rrnB gene," Eur. J. Biochem., 201: 653-659 [1991].
Reiser, S., et al., "Isolation of mutants of Acinetobacter calcoaceticus deficient in wax ester synthesis and complementation of one mutation with a gene encoding a fatty acyl coenzyme A reductase," J. Bacteriol., 179:2969-2975 (1997).
Sadler, J.R., et al., "A perfectly symmetric lac operator binds the lac repressor very tightly," PNAS, 80: 6785-6789 [1983].
Smith, M., "In Vitro Mutagenesis," Ann. Rev. Genet., 19:423-462 [1985].
Steen, E.J., et al., "Microbial production of fatty-acid-derived fuels and chemicals from plant biomass", Nature, 463:559-562 [2010].
Terpe, K., "Overview of bacterial expression systems for heterologousprotein production: from molecular and biochemicalfundamentals to commercial systems," Appl. Microbiol. Biotechnol., 72:211-222 [2006].
The UniProt Consortium, "The Universal Protein Resource (UniProt) in 2010," Nucleic Acid Res., 38:D142-D148 [2010].
Tsujita, T., et al., "Fatty Acid Alcohol Ester-Synthesizing Activity of Lipoprotein Lipase" J. Biochem. 126:1074-1079 [1999].
Villa-Komaroff, L., et al., "A bacterial clone synthesizing proinsulin," Proc. Natl Acad. Sci. USA, 75:3727-3731 (1978).
Voelker, T.A., et al., "Alteration of the specificity and regulation of fatty acid synthesis of Escherichia coli by expression of a plant medium-chain acyl-acyl carrier protein thioesterase," J. Bacteriol., 176:7320-7327[1994].
Warrens, A.N., et al., "Splicing by overlap extension by PCR using asymmetric amplification: an improved technique for the generation of hybrid proteins of immunological interest," Gene, 186(1):29-35 [1997].
Weil, J., et al. "Pretreatment of Yellow Poplar Sawdust by Pressure Cooking in Water," Appl. Biochem. Biotechnol., 68(1-2): 21-40 [1997].

(56) References Cited

OTHER PUBLICATIONS

Zheng, Y., et al., "Optimization of fatty alcohol biosynthesis pathway for selectively enhanced production of C12/14 and C16/18 fatty alcohols in engineered *Escherichia coli*", Microbial Cell Factories, 11(65): E pp. 1-11 [May 20, 2012].

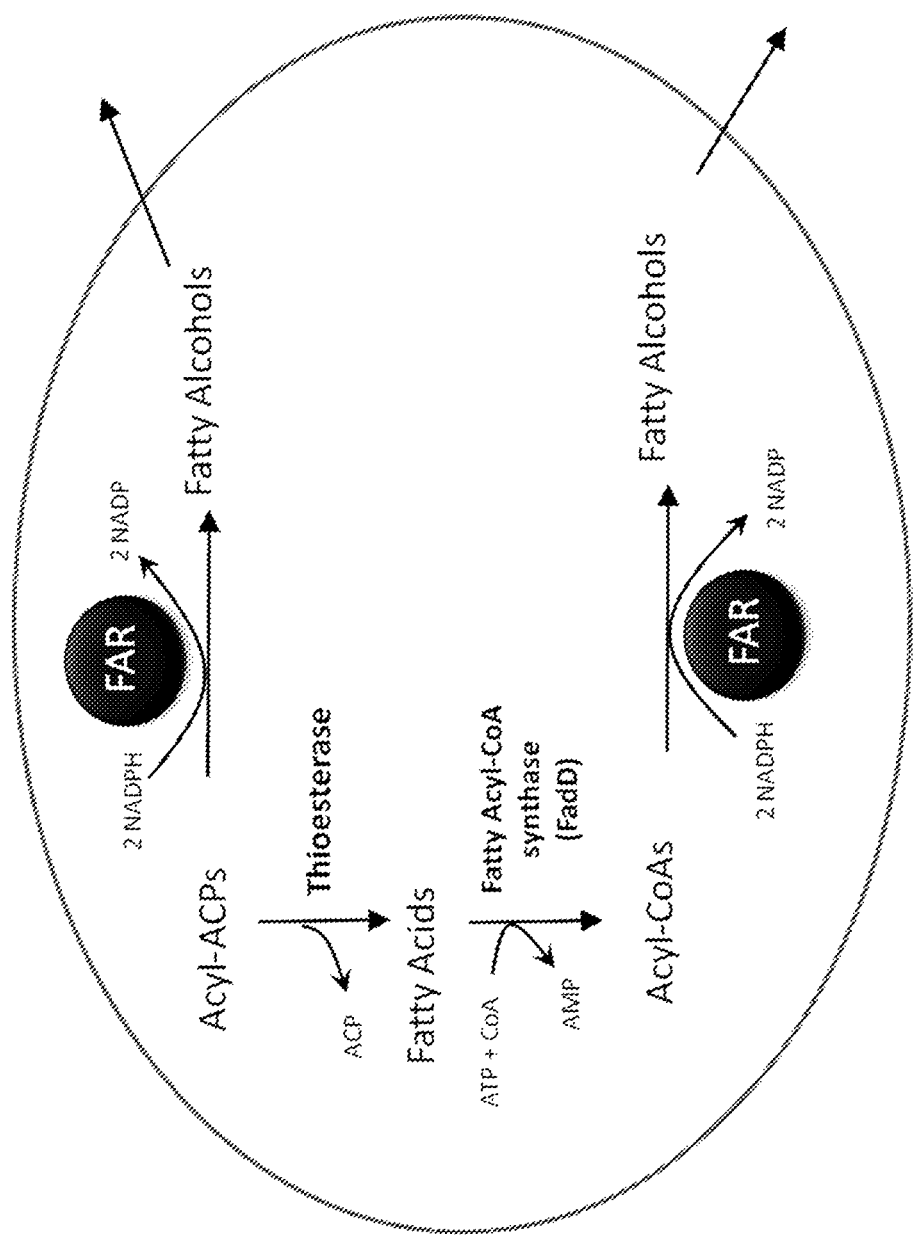

PRODUCTION OF FATTY ALCOHOLS FROM ENGINEERED MICROORGANISMS

CROSS-REFERENCE TO RELATED APPLICATIONS

This application claims priority to co-pending U.S. patent application Ser. No. 14/394,817, filed Oct. 16, 2014, which claims priority to PCT/US2013/037472, filed Apr. 19, 2013, which claims priority to U.S. Provisional Application No. 61/636,044, filed Apr. 20, 2012; U.S. Provisional Application No. 61/674,053, filed Jul. 20, 2012; PCT International Application No. PCT/US2012/069444, filed Dec. 13, 2012; and PCT International Application No. PCT/US2012/069553, filed Dec. 13, 2012; the entire content of each of which is hereby incorporated by reference for all purposes.

REFERENCE TO A SEQUENCE LISTING, A TABLE, OR A COMPUTER PROGRAM LISTING APPENDIX SUBMITTED AS AN ASCII FILE

The Sequence Listing written in file CX5-113WO2_ST25.TXT, created on May 9, 2016, 94,208 bytes, machine format IBM-PC, MS-Windows operating system, is hereby incorporated by reference.

FIELD OF THE INVENTION

This invention relates to recombinant microorganisms and particularly recombinant bacterial microorganisms exhibiting improved properties, especially improved production of fatty alcohols comprising carbon chain lengths of one or more of C12, C14 and C16.

BACKGROUND OF THE INVENTION

Crude petroleum has traditionally been used as a primary source for raw materials for producing numerous specialty chemicals. Particular specialty chemicals that can be produced from the petrochemical raw materials include fatty alcohols. Fatty alcohols have many industrial and commercial uses. For example, fatty alcohols act as surfactants which are useful in personal care and household products, such as detergents. Fatty alcohols are also used in waxes, lubricating oils, cosmetics and solvents. However, obtaining fatty alcohols from crude petroleum requires a significant amount of energy and involves the use of a non-renewable energy source.

Further, even those fatty alcohols that are obtained from renewable sources such as from plant or animal derived fatty acids generally are prepared using a hydrogenation step. Hydrogenation is a costly process step but is utilized to eliminate the double bonds of unsaturated fatty acids. A number of prior art references disclose genetically engineered microorganisms that produce products including fatty acid derivatives such as fatty acid esters and fatty alcohols. For example reference is made to International application publications WO 2007/136762; WO 2008/119082; WO2010/075483; WO2011/008535; and WO 2011/019858; and U.S. Pat. No. 6,143,538. However a need still exists in the field for improved fatty alcohol production from bioengineered microorganisms that is efficient and cost effective and further that is tailored for use in particular industrial applications, such as for example in detergent compositions per se and in the production of surfactants for use therein. In addition, for certain industrial applications, the presence of one or more double bonds in a fatty alcohol is not a desirable characteristic because the double bond lowers the melting point, reduces the shelf-life and reduces the heat stability of the fatty alcohol. Therefore, compositions and methods that provide products having increased saturation levels in fatty alcohols are also commercially beneficial.

BRIEF SUMMARY OF THE INVENTION

The invention relates to the production of a fatty alcohol composition from cultured recombinant microbial cells. Generally the fatty alcohols are produced by expressing a gene encoding a heterologous fatty alcohol forming acyl-CoA reductase ("FAR"); a gene encoding a heterologous thioesterase ("TE") gene and a gene encoding an acyl-CoA synthetase ("ACS"). The recombinant microbial cells in some embodiments are *E. coli* cells. Further the invention relates to fatty alcohol compositions comprising the fatty alcohols or derivatives thereof produced by the recombinant microbial cells. These fatty alcohol compositions may be used inter alia in detergent compositions, cleaning compositions and personal care compositions.

In certain embodiments, the fatty alcohols are produced by a biosynthetic pathway depicted in FIG. 1. In certain embodiments of this pathway, a fatty acid is activated by ATP and reduced to generate an acyl-CoA by a fatty acyl CoA synthase. The acyl CoA is further reduced by a FAR to produce fatty alcohols.

In one aspect, the invention provides a recombinant bacterial microorganism comprising (a) a gene encoding a heterologous thioesterase ("TE"); (b) a gene encoding a heterologous fatty alcohol forming acyl-CoA reductase ("FAR") and (c) an over-expressed acyl-CoA synthetase ("ACS"); wherein the recombinant bacterial microorganism when cultured in the presence of a carbon source under suitable culture conditions produces a fatty alcohol composition. In certain embodiments, the recombinant bacterial microorganism is an *E. coli*. In certain embodiments, the TE is encoded by a fatB gene. In some aspects the TE has an amino acid sequence comprising at least 85% (88%, 90%, 91%, 92%, 93%, 94%, 95%, 96%, 97%, 98%, or 99%) sequence identity to SEQ ID NO:10 or SEQ ID NO:35. In some aspects, the fatB gene encoding the TE comprises at least 85% (88%, 90%, 91%, 92%, 93%, 94%, 95%, 96%, 97%, 98%, or 99%) sequence identity to SEQ ID NO:9 or SEQ ID NO:34. In certain embodiments, the FAR is encoded by a gene selected from the following organisms *Marinobacter algicola*, *Marinobacter aquaeolei*, *Oceanobacter* sp., *Mus musculus*, or *Hahella chejuensis*. In certain embodiments, the FAR has an amino acid sequence comprising at least 75% (80%, 85%, 90%, 91%, 92%, 93%, 94%, 95%, 96%, 97%, 98%, 99% or even 100%) sequence identity to SEQ ID NO: 2, SEQ ID NO: 4, SEQ ID NO:6, SEQ ID NO:37, or SEQ ID NO:39. In certain embodiments, the gene encoding the FAR comprises a nucleic acid sequence having at least 90% (91%, 92%, 93%, 94%, 95%, 96%, 97%, 98%, 99% or even 100%) sequence identity to SEQ ID NO:3, SEQ ID NO:5, SEQ ID NO: 7, SEQ ID NO: 36 or SEQ ID NO: 38. In certain embodiments, the nucleic acid sequence encoding the FAR is a codon optimized polynucleotide sequence. In certain embodiments, the ACS has an amino acid sequence comprising at least 85% (88%, 90%, 91%, 92%, 93%, 94%, 95%, 96%, 97%, 98%, 99% or even 100%) sequence identity to SEQ ID NO: 8. In certain embodiments, the gene encoding ACS comprises a nucleic acid sequence having at least 90% (91%, 92%, 93%, 94%, 95%, 96%, 97%, 98%, 99% or even 100%) sequence identity to SEQ ID NO: 7.

In a second aspect, the invention provides the embodiments presented in the first aspect and further comprises a recombinant bacterial microorganism comprising an inactivated fadR gene and/or an inactivated fadE. In certain embodiments the inactivated fadR gene comprises a nucleic acid sequence having at least 90% (91%, 92%, 93%, 94%, 95%, 96%, 97%, 98%, 99% or even 100%) sequence identity to SEQ ID NO: 11. In certain embodiments, the inactivated fadE gene comprises a nucleic acid sequence having at least 90% (91%, 92%, 93%, 94%, 95%, 96%, 97%, 98%, 99% or even 100%) sequence identity to SEQ ID NO: 13.

In another aspect, the invention provides a fatty alcohol composition produced by a recombinant bacterial microorganism as embodied in the first or second aspect. In certain embodiments, the fatty alcohol composition comprises at least 60% (65%, 70%, 75%, 80%, 85%, 90% or 95% by weight of C12, C14, or C16 fatty alcohols or any combination thereof.

In a further aspect, the invention provides a method of producing a fatty alcohol composition. In certain embodiments, the method comprises culturing a recombinant bacterial microorganism as encompassed in the first or second aspect under suitable culture conditions with a suitable carbon source to produce a fatty alcohol composition and producing said fatty alcohol composition. In certain embodiments, at least 50% of the produced fatty alcohols are secreted into the culture. In certain embodiments the method further comprises recovering the produced fatty alcohol composition from the culture. In certain embodiments, the recovered fatty alcohols are used to produce alkanes and/or fatty esters. In certain embodiments, the produced fatty alcohol composition comprises at least 60% (65%, 70%, 75%, 80%, 85%, 90% or 95%) by weight of C12, C14, or C16 fatty alcohols or any combination thereof. In certain embodiments, the produced fatty alcohol composition comprises at least 0.5 g/L (and also at least 5.0 g/L) of fatty alcohols. In certain embodiments, the recombinant microorganism that produces the fatty alcohol composition is cultured at a temperature in the range of 20° C. to 45° C.; a pH in the range of pH 5 to pH 7; and for a time in the range of from 16 hours to 144 hours. In certain embodiments, the microorganism is cultured in the presence of fermentable sugars obtained from a cellulosic feedstock.

In yet another aspect, the invention provides a fatty alcohol composition comprising the fatty alcohols produced according to any one of the aspects above wherein the fatty alcohol composition is used in a detergent composition, a personal care composition or a cleaning composition.

In other aspects the invention provides a recombinant bacterial microbial culture that produces a composition of fatty alcohols said fatty alcohol composition comprising fatty alcohols having a carbon chain length of at least 60% of C12, C14 and C16 fatty alcohols, the culture comprising a recombinant bacterial microorganism comprising (a) a gene encoding a heterologous thioesterase ("TE"); (b) a gene encoding a heterologous fatty alcohol forming acyl-CoA reductase ("FAR") and (c) an over-expressed acyl-CoA synthetase ("ACS"). In some embodiments of this aspect the recombinant bacterial culture is comprised of E. coli cells. In other embodiments of this aspect the heterologous TE has an amino acid sequence comprising at least 90% or at least 95% sequence identity to SEQ ID NO: 10 or SEQ ID NO: 35; the heterologous FAR has an amino acid sequence comprising at least 90% or at least 95% sequence identity to SEQ ID NOs: 2, 4, 6, 37 or 39 (and in particular at least 95% or at least 98% sequence identity to SEQ ID NO: 37 or SEQ ID NO: 39); and the over-expressed ACS has an amino acid sequence comprising at least 90% or at least 95% sequence identity to SEQ ID NO: 8. In yet further embodiments of this aspect the fatty alcohol composition comprises fatty alcohols having a carbon chain length of at least 20% (and also at least 30% and in some cases at least 50%) of C12 fatty alcohols and in other embodiments the fatty alcohol composition comprises at least 80% by weight of C12, C14 or C16 fatty alcohols. In some embodiments of this aspect, at least 50% of the fatty alcohols produced by the recombinant bacterial cells are secreted from said cells into culture. In further embodiments, the fatty alcohol composition produced by the recombinant cells is recovered from the extracellular culture and/or the recombinant bacterial cells.

BRIEF DESCRIPTION OF THE DRAWINGS

FIG. 1 illustrates a pathway for the production of fatty alcohols in a recombinant cell according to an embodiment of the invention, wherein the fatty alcohols are secreted from the recombinant cell.

DEFINITIONS

Unless defined otherwise herein, all technical and scientific terms used herein have the same meaning as commonly understood by one of ordinary skill in the art to which this invention pertains. Many technical dictionaries are known to those of skill in the art. Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art.

Also, as used herein, the singular "a", "an," and "the" include the plural references, unless the context clearly indicates otherwise. Further, the term "or" is used in the present application to mean the disjunctive "or" and the conjunctive "and".

Amino acids are designated using the three-letter symbols or one-letter symbols recommended by the IUPAC-IUB Biochemical Nomenclature Commission. Unless otherwise indicated, nucleic acids are written left to right in 5' to 3' orientation; amino acid sequences are written left to right in amino to carboxy orientation, respectively. "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

As used herein, the term "comprising" and its cognates are used in their inclusive sense (i.e., equivalent to the term "including" and its corresponding cognates).

The term "fatty alcohol" as used herein refers to an aliphatic alcohol of the formula R—OH, where the R group is at least 4, 5, 6, 7, 8, 9, 10, 11, 12, 13, 14, 15, 16, 17, 18, 19, 20 or more carbons in length. R can be saturated or unsaturated. Further saturated or unsaturated fatty alcohols can be described as "Ca:b-OH", wherein "a" is an integer that represents the total number of carbon atoms in the fatty alcohol and "b" is an integer that refers to the number of double bonds in the carbon chain. In some embodiments, a fatty alcohol produced according to the methods disclosed herein is a C8-C24 saturated or unsaturated fatty alcohol (i.e., a C8, C9, C10, C11, C12, C13, C14, C15, C16, C17, C18, C19, C20, C21, C22, or C24 fatty alcohol). In some embodiments, multiple fatty alcohols are produced with varying saturation levels. For example, in some embodiments, C10, C12, C14, C16 and/or C18 fatty alcohols are produced. However, it is not intended that the present invention be limited to any particular fatty alcohol nor fatty alcohol saturation level. In some embodiments, one or more of the following fatty alcohols is produced: 1-decanol (C10: 0), 1-dodecanol (C12:0), 1-tetradecanol (C14:0), 1-hexadecanol (C16:0), 1-octadecanol (C18:0).

The term "carbon chain length" as used herein means the number of carbon atoms in a carbon chain of a fatty alcohol, fatty alcohol substrate or fatty alcohol derivative. For example the term "C12 fatty alcohol" refers to a fatty alcohol molecule having 12 carbons.

The phrase "preference for cleaving a substrate having a certain carbon chain length" or "predominantly cleaving a substrate having a certain carbon chain length" means that an enzyme cleaves or hydrolyzes mainly substrates having a defined number of carbon atoms. The preference is not necessarily exclusive. For example, an enzyme may have a preference for cleaving substrates with chain lengths of 12 carbons, may still cleave substrates having chain length of 10 or 14 carbon atoms. A more specific non-limiting example includes but is not limited to a TE that predominantly hydrolyzes C12 acyl ACP. The enzyme may still cleave a C10 or C14 ACP substrate.

The term a "fatty alcohol composition" as used herein, means a composition which encompasses at least one fatty alcohol and which is produced from an engineered (e.g. recombinant) microbial organism according to the methods of the invention. The fatty alcohol compositions of the invention may include one or more fatty alcohols. For example a fatty alcohol composition may include only C12 fatty alcohols or a fatty alcohol composition may include a combination of C12, C14 and C16 fatty alcohols and these fatty alcohols may be saturated or unsaturated fatty alcohols and linear, or branched.

The term "fatty acid" as used herein means a compound having the formula $RCO_2H$, wherein R is at least two carbons in length. In general R is between 4 and 22 carbons. Fatty acids may be saturated or unsaturated and further R may be linear or branched.

The term "fatty acyl-ACP as used herein means a compound having the formula RCOS-ACP, wherein "R" is at least three carbons in length and may be a straight chain or branched chain and saturated or unsaturated. The abbreviation "ACP" refers to an acyl carrier protein.

The terms "fatty acyl-CoA reductase", "fatty acyl reductase", and "fatty acyl acyl-ACP reductase" (EC 1,1.1.*) are used interchangeably herein to refer to an enzyme that catalyzes the reduction of a fatty acyl-CoA, a fatty acyl-ACP, or other fatty acyl thioester complex to a fatty alcohol, in a reaction linked to the oxidation of NAD(P)H to NAD(P)$^+$. The abbreviation "FAR" is used herein to refer to these fatty alcohol forming enzymes. In some embodiments, a FAR enzyme includes functional fragments. In some embodiments, the FAR enzyme is a modified or variant FAR, wherein a wild-type FAR has been genetically modified to include at least 1 (at least 2, 3, 4, 5, 6, 7, 8, 9, 10, 12, 15, 20, 25, 30 or more) amino acid alterations (e.g., substitutions, deletions and/or insertions) as compared to a reference FAR.

The term "acyl-CoA" refers to an acyl thioester formed between the carbonyl carbon of an alkyl chain and the sulfydryl group of the 4'-phosphopantetthionyl moiety of co-enzyme A (CoA) which has the formula R—C(O)—S-CoA, wherein R is an alkyl group having at least 4 carbon atoms and preferably between 10 and 14 carbon atoms. R may be straight or branched and saturated or unsaturated.

The term "FadD" enzyme as used herein refers to an "acyl-CoA synthetase ("ACS") (EC 6.2.1 (acid-thiol ligases)). In some embodiments, the ACS is classified as EC 6.2.1.3. These ACSs are also known as long chain fatty acid-CoA ligases. An ACS catalyzes the reaction of free fatty acids (both saturated and unsaturated fatty acids) into metabolically active CoA esters (e.g., acyl-CoA) during fatty acid degradation. In E. coli FadD is encoded by a fadD gene. In some embodiments the FadD may be classified as EC 2.3.1.86 (fatty acyl CoA synthase).

The term "FadK" enzyme as used herein is another acyl-CoA synthetase found in E. coli and other bacteria (ACS) (EC 6.2.1) that catalyzes the reaction of free fatty acids having preferentially C10 or less carbon chain lengths. In some cases the gene (fadK) encoding FadK has also been known as ydiD. Reference is made to Morgan-Kiss R M et al., 2004 J. Biol. Chem., 279:37324-37333.

In some bacterial organisms, (e.g. E. coli) fadD and fadK genes both occur and encode enzymes having ACS activity. In some bacterial organisms there may be more than two genes which encode enzymes having ACS activity.

The term "thioesterase or thioester hydrolase (TE)" enzyme used herein means an enzyme having thioesterase activity. TEs are identified as members of EC 3.1.2.1 to EC 3.1.2.27 and also EC3.1.1.5 and EC 3.1.2.-) and these enzyme which hydrolyze the thioester bond between a carbonyl group and a sulfur atom are classified based on enzyme function and substrate identity. In addition, TEs are classified based on the ThYme database (Thioester-active enzyme). In this classification system, TEs have been classified based on amino acid sequence similarity. Under the ThYme system, TEs are further divided into 24 different families (TE1-TE24). Reference is made to D. C. Cantu et al., (2010) Protein Science, 19:1281-1295 and D. C. Cantu et al., (2011) Nucleic Acid Research 39:doi10:1093/nar/gkq1072. TEs according to the invention will have the ability to catalyze a thioester cleavage reaction hydrolyzing a thioester into an acid and a thiol. TEs useful in the invention may be obtained from a number of sources including plant, bacterial, algal, and fungal sources.

The phrase "fatty acid biosynthetic enzymes" as used herein means a complex of enzymes involved in a number of reactions to produce saturated and unsaturated fatty acids. The process is primed by the enzymatic conversion of malonyl-CoA into malonyl-ACP and continues by successive addition of 2 carbons derived from malonyl-ACP residues, providing ACP intermediates (i.e., acyl-ACPs). There are at least 8 enzymes involved fatty acid biosynthesis including FabA, FabB, FabD, FabF, FabG, FabH, FabI, and FabZ, collectively and individually referred to herein as "fatty acid biosynthetic" enzymes. Furthermore, the ACP protein plays a key role in fatty acid biosynthesis by anchoring the nascent acyl chain and making the acyl chain accessible to other enzymes.

The phrase "altered level of expression" means a polynucleotide or polypeptide in a recombinant microorganism encompassed by the invention is present in an amount or concentration that is different (e.g. greater or less) than the amount or concentration when compared to a corresponding reference microorganism.

The term "FadR" protein as used herein refers to a multifunctional dual regulator of E. coli that exerts negative control over the fatty acid degradative regulon and activates expression of fabA and fabF. The FadR regulator is encoded by a fadR gene. A "regulon" comprises a set of genes under control of a single regulatory protein.

The term "FadE" enzyme as used herein means an acyl-CoA dehydrogenase enzyme (EC 1.3.99.-) such as from E. coli. A FadE gene is also known as yafH.

Throughout the specification a reference may be made using an abbreviated gene name or an enzyme name. For example "fadD" refers to a gene encoding an acyl-CoA synthetase enzyme (ACS) or as sometimes referred to herein a FadD enzyme.

The term "analogous sequence" or "homologous sequence" as used herein means a sequence wherein the function of the gene is essentially the same as a reference gene. For example, a reference gene may be a fadD gene from E. coli. In some embodiments, the analogous sequence will have at least about 60%, for example, at least about 65%, 70%, 75%, 80%, 85%, 88%, 90%, 91%, 92%, 93%, 94%, 95%, 96%, 97%, 98%, or 99% sequence identity with the reference sequence.

The term "wild-type" or "native" as used herein in reference to a polypeptide or protein mean a polypeptide or protein expressed by a naturally occurring microorganism found in nature. When used in reference to a microorganism, the term means a naturally occurring (not genetically modified or engineered) microorganism.

The term "substrate" as used herein refers to a substance or compound that is converted or suitable for conversion into another compound (e.g., a product) by the action of at least one enzyme. The term includes not only a single compound but also combinations comprising more than one compound.

The term "conversion" as used herein refers to the enzymatic transformation of a substrate to at least one corresponding product. "Percent conversion" refers to the percent of the substrate that is converted to the product(s) within a specified period of time and under specified conditions.

Nucleic acid sequences may be "introduced" into a cell by protoplast fusion, transfection, transduction, transformation, electroporation or any other suitable method known in the art. A nucleic acid sequence introduced into a eukaryotic or prokaryotic cell may be integrated into a chromosome or may be maintained as an episome.

The terms "transformed" and "stably transformed" as used herein refer to a cell that has a non-native (i.e., heterologous) polynucleotide sequence integrated into its genome or as an episomal plasmid that is maintained for at least two generations.

The term "gene" as used herein refers to a polynucleotide (e.g., a DNA segment), that encodes a polypeptide and includes regions preceding and following the coding regions as well as intervening sequences (introns) between individual coding segments (exons).

The terms "endogenous" or "homologous" when used in reference to a gene refers to a gene that is found in a parental strain of a cell (e.g., a fungal or bacterial cell). As used herein in making comparisons between nucleic acid sequences, "homologous genes" (or "homologue" genes) refers to genes from different, but usually related species, which correspond to each other and are identical or very similar to each other. The term encompasses genes that are separated by speciation (i.e., the development of new species) (e.g., orthologous genes), as well as genes that have been separated by genetic duplication (e.g., paralogous genes).

The term "heterologous" polynucleotide as used herein means any polynucleotide that is introduced into a host cell by laboratory techniques, and includes polynucleotides that are removed from a host cell, subjected to laboratory manipulation, and then reintroduced into a host cell.

In some embodiments, when "heterologous" is used with reference to a nucleic acid or polypeptide, the term refers to a sequence that is not normally expressed and secreted by an organism (e.g., a "wild-type" organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

As used herein, a "heterologous enzyme" is used in reference to an enzyme that is encoded by a heterologous gene. However, it is also contemplated herein that a heterologous gene can encode an endogenous or homologous enzyme. As used herein, the term "heterologous gene" refers to a gene that occurs in a form not found in a parental strain of the host cell. Thus, in some embodiments, a heterologous gene is a gene that is derived from a species that is different from the species of the host cell expressing the gene. In some embodiments, a heterologous gene is a modified version of a gene that is endogenous to the host cell (e.g., an endogenous gene subjected to manipulation and then introduced or transformed into the host cell). For example, in some embodiments, a heterologous gene has an endogenous coding sequence, but has modifications in the promoter sequence. Similarly, in other embodiments, a heterologous gene encodes the same amino acid sequence as an endogenous gene, but has modifications in codon usage and/or to noncoding regions (e.g., introns), and/or combinations thereof. In some embodiments, the heterologous gene is a gene that has been modified to overexpress a gene product of interest.

The term "expression" as used herein includes any step involved in the production of a polypeptide including, but not limited to, transcription, post-transcriptional modification, translation, post-translational modification, and secretion.

The term "overexpression" as used herein refers to any state in which a gene is caused to be expressed at an elevated rate or level as compared to the endogenous expression rate or level for that gene. In some embodiments, "overexpression" includes an elevated translation rate or level of the gene compared to the endogenous translation rate or level for that gene. In some embodiments, overexpression includes an elevated transcription rate or level of the gene compared to the endogenous transcription rate or level for that gene. It is intended that the term encompass overexpression of endogenous, as well as heterologous proteins.

The term "recombinant" as used herein includes reference to a cell or vector, that has been modified by the introduction of a heterologous nucleic acid sequence or that the cell is derived from a cell so modified. Thus, for example, recombinant cells express genes that are not found in identical form within the native (i.e., non-recombinant) form of the cell or express native genes that are otherwise abnormally expressed, under-expressed or not expressed at all as a result of deliberate human intervention. "Recombinant," "engineered," and "non-naturally occurring," when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (i.e., non-recombinant) form of the cell or express native genes that are otherwise expressed at a different level.

The term "plasmid" as used herein refers to a circular double-stranded (ds) DNA construct used as a cloning vector, and which forms an extrachromosomal self-replicating genetic element in some eukaryotes or prokaryotes, or integrates into the host chromosome.

The term "operably linked" as used herein refers to a configuration in which a control sequence is appropriately placed (i.e., in a functional relationship) at a position relative to a polynucleotide of interest such that the control sequence directs or regulates the expression of the polynucleotide and/or polypeptide of interest. Thus, a nucleic acid is "operably linked" to another nucleic acid sequence when it is placed into a functional relationship with another nucleic acid sequence.

The term "control sequence" as used herein includes all components, which are necessary and/or advantageous for the expression of a polynucleotide of the present disclosure. Each control sequence may be native or foreign to the polynucleotide of interest. Such control sequences include, but are not limited to, leaders, polyadenylation sequences, propeptide sequences, promoters, signal peptide sequences, and transcription terminators.

The terms "modified host cell", "engineered host cell" or "recombinant host cell" as used herein refer to a cell whose genetic material has been altered using genetic engineering techniques. A genetically modified cell also refers to a derivative of or the progeny of a cell whose genetic material has been altered using genetic engineering techniques. An example of a genetic modification as a result of genetic engineering techniques includes a modification to the genomic DNA. Another example of a genetic modification as a result of genetic engineering techniques includes introduction of a stable heterologous nucleic acid into the cell.

The phrase "a corresponding engineered cell grown under essentially the same culture conditions" as used herein means a reference host cell (either engineered or native) which is grown under essentially the same culture conditions, including but not limited to pH, temperature, time, and culture media as compared to an engineered cell encompassed by the invention and to which the reference cell is being compared to. In some specific nonlimiting examples the engineered cell encompassed by the invention which comprises heterologous polynucleotides encoding a TE, FAR (i.e., FAR-V4) and FadD will be compared to a reference cell comprising the same FAR (i.e., FAR-V4) under essentially the same conditions.

The term "carbon source" as used herein refers to a substrate that is suitable for use as a source of carbon for cell growth.

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology—Hybridization with Nucleic Acid Probes*," Part 1, Chapter 2, Elsevier, New York, (1993), incorporated herein by reference). For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. ("low" stringency), at least at 55° C. ("medium" or "moderate" stringency), at least at 60° C. ("medium-high" stringency), at least at 65° C. ("high" stringency), and at least at 70° C. ("very high" stringency). In some embodiments, the stringency conditions include those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. In other embodiments, the stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors to accomplish the desired stringency.

The phrase "naturally-occurring enzyme" as used herein refers to an enzyme having an unmodified amino acid sequence which is identical to that found in nature (i.e., "wild-type"). Naturally occurring enzymes include native enzymes (i.e., those enzymes naturally expressed or found in the particular microorganism).

The term "variant" or "mutant" as used interchangeably herein refer to a polypeptide sequence or polynucleotide sequence encoding a polypeptide, said sequence comprising one or more modifications relative to a corresponding wild-type enzyme (or other specified reference sequence) or the wild-type polynucleotide (or other specified reference sequence) such as substitutions, insertions, deletions, and/or truncations of one or more specific amino acid residues or of one or more specific nucleotides or codons in the polypeptide or polynucleotide. In some embodiments, reference to a variant at an amino acid residue refers to a substitution of the amino acid residue for another amino acid residue. Mutagenesis and directed evolution methods are well known in the art for creating variants. See, e.g., U.S. Pat. No. 7,783, 428; U.S. Pat. No. 6,586,182; U.S. Pat. No. 6,117,679; and Ling, et al., 1999, "Approaches to DNA mutagenesis: an overview," *Anal. Biochem.*, 254(2):157-78; Smith, 1985, "In vitro mutagenesis," *Ann. Rev. Genet.*, 19:423-462; Carter, 1986, "Site-directed mutagenesis," *Biochem. J.*, 237:1-7; Minshull, et al., 1999, "Protein evolution by molecular breeding," *Current Opinion in Chemical Biology*, 3:284-290;

The terms "isolated" or "recovered" as used herein refer to a material that is removed from its original environment (e.g., the natural environment, if it is naturally occurring). For example, the material is said to be "isolated" when it is present in a particular composition in a higher or lower concentration than exists in a naturally-occurring or wild-type organism or in combination with components not normally present upon expression from a naturally-occurring or wild-type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still considered to be isolated, in that such vector or composition is not part of its natural environment. In some embodiments, the term isolated refers to fatty alcohol compounds of varying chain lengths which are isolated or recovered from an engineered cell according to the invention.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, the term "biologically active fragment," or "functional fragment" refers to a polypeptide that has an amino-terminal and/or carboxy-terminal deletion(s) and/or internal deletion(s), but where the remaining amino acid sequence is identical to the corresponding positions in the sequence to which it is being compared (e.g., a full-length FAR of the present invention) and that retains substantially all of the activity of the full-length polypeptide. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length polypeptide to which the functional fragment is being compared to (e.g., a functional fragment of a FAR polypeptide may comprises at least 80%, (85%, 90%, 93%, 95%, 96%, 97%, 98%, or 99%) of the amino acid sequence of SEQ ID NOs: 4, 6, 37 or 39).

The term "inactivated" as applied to a gene refers to any genetic modification that decreases or eliminates the expression of the gene and/or the functional activity of the corresponding gene product (mRNA and/or protein). The term encompasses complete or partial inactivation, suppression, deletion, interruption, blockage, promoter alterations, antisense RNA, dsRNA, or down-regulation of a gene. This can be accomplished, for example, by gene "knockout," inactivation, mutation (e.g., insertion, deletion, point, or frameshift mutations that disrupt the expression or activity of the gene product), or by use of inhibitory RNAs (e.g., sense, antisense, or RNAi technology). A deletion may encompass all or part of a gene's coding sequence. The term "knockout" refers to the deletion of most (at least about 95%, at least about 96%, at least about 97%, at least about 98%, or at least about 99%) or all (100%) of the coding sequence of a gene. In some embodiments, any number of nucleotides can be deleted, from a single base to an entire piece of a chromosome.

With respect to "homologs," reference to particular gene names is for illustration and not limitation. It is understood that gene names vary from organism to organism and reference to a gene name is not intended to be limiting, but is intended to encompass homologs and polymorphic variants with equivalent activity. In certain embodiments, the invention includes a polynucleotide or polypeptide sequence with at least about 50%, about 60%, about 70%, about 75%, about 80%, about 85%, about 90%, about 91%, about 92%, about 93%, about 94%, about 95%, about 96%, about 97%, about 98%, or about 99% identity with the named gene or gene product.

The terms "peptide," "polypeptide," and "protein" are used interchangeably herein to refer to a polymer of amino acid residues. In various aspects of the invention, the availability of a polypeptide sequence of a specific enzyme provides a description of all polynucleotides capable of encoding the polypeptide of known sequence because of the known correspondence of particular codons and the amino acids they encode. In certain embodiments, the degeneracy of the genetic code is used to produce a large number of polynucleotides that encode a polypeptide described herein.

"Identity" or "percent identity" in the context of two or more polypeptide sequences or two or more polynucleotide sequences refers to two or more sequences or sub-sequences that are the same or have a specified percentage of amino acid residues or nucleotide residues that are the same. For example, the sequence can have a percent identity of at least about 50%, about 60%, about 70%, about 75%, about 80%, about 85%, about 90%, about 91%, about 92%, about 93%, about 94%, about 95%, about 96%, about 97%, about 98%, or about 99% over a specified region to a reference sequence when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a polypeptide has sequence identity to SEQ ID NO:2 or any other sequence as herein disclosed is the BLAST algorithm, which is described in Altschul et al., 1990, *J. Mol. Biol.* 215:403-410, which is incorporated herein by reference. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915). Other programs that may be used include the Needleman-Wunsch procedure, J. Mol. Biol. 48: 443-453 (1970), using blosum62, a Gap start penalty of 7 and gap extend penalty of 1; and gapped BLAST 2.0 (see Altschul, et al. 1997, Nucleic Acids Res., 25:3389-3402) both available to the public at the National Center for Biotechnology Information Website.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation, Version 8.01, July 2009, WorldWideWeb.tcoffee.org), or Protein Align. In Protein Align, alignments are computed by optimizing a function based on residue similarity scores (obtained from applying an amino acid substitution matrix to pairs of aligned residues) and gap penalties. Penalties are imposed for introducing and extending gaps in one sequence with respect to another. The final optimized function value is referred to as the alignment score. When aligning multiple sequences, Protein Align optimizes the "sum of pairs" score, i.e., the sum of all the separate pairwise alignment scores.

As used herein, the term "culturing" refers to growing a population of microbial cells under suitable conditions using any suitable medium (e.g., liquid, solid, or semi-solid media).

The term "extracellular environment" means the aqueous solution surrounding a cell membrane, excluding the intracellular space. For example, a secreted enzyme or a compound is found in the extracellular environment. In some embodiments, the extracellular environment comprises the culture medium used to grow the cell.

The term "contacting" refers to combining an enzyme and a substrate under conditions in which the enzyme can act on the substrate. Those skilled in the art will recognize that mixing a solution containing an enzyme with a substrate will effect "contacting." Similarly, in the context of culturing microorganisms, culturing microorganisms in a media containing a substrate (e.g., a fermentable sugar) will effect "contacting" the microorganism with the substrate.

The term "fermentable sugars" refers to simple sugars (monosaccharides, disaccharides and short oligosaccharides) such as but not limited to glucose, xylose, galactose, arabinose, mannose and sucrose. Fermentable sugar is any sugar that a microorganism can utilize or ferment.

The terms "cleaning compositions" and "cleaning formulations" refer to compositions that find use in the removal of undesired compounds from items to be cleaning, such as fabric, dishes, contact lenses, other solid substrates, hair (shampoos), skin (soaps and creams), teeth (mouthwashes, toothpastes, etc.), etc. The terms further refer to any composition that is suited for cleaning, bleaching, disinfecting and/or sterilizing any object and/or surface. It is intended that the terms include, but are not limited to detergent compositions (e.g., laundry and fine fabric detergents), hard surface cleaning formulations (e.g., for glass, wood, ceramics and metal countertops, windows, etc.), oven cleaners, carpet cleaners, fabric fresheners, fabric softeners, hand and machine dish detergents, dish rinse aids, and textile and laundry pre-spotters. In addition, the terms encompass cleaning compositions for use in household and institutional use, including but not limited to liquid cleaning and disinfecting agents, such as anti-bacterial handsoaps and wipes, cleaning bars, mouthwashes, denture cleaners, car shampoos, bathroom cleaners, hair shampoos and conditioners/rinses for humans and other animals, shower gels, foam baths, etc. Indeed, it is not intended that the term be limited to any particular cleaning composition. The terms encompass any materials/compounds selected for the particular type of cleaning compositions desired and the form of the product (e.g., liquid, gel, granule, or spray), as long as the composition is compatible with the fatty alcohol(s) of the present invention. The specific selection of cleaning composition materials are readily made by considering the surface, item or fabric to be cleaned, and the desired form of the composition for the cleaning conditions during use.

DETAILED DESCRIPTION OF THE INVENTION

1. Thioesterase

According to one embodiment of the invention, a microbial host cell is engineered to express a heterologous thioesterase ("TE"). The thioesterase may be one that preferentially uses C12, C14 or C16 ACPs. Depending on the TE used, a homogenous population of fatty alcohols may be produced. For example, if the TE is one that predominantly uses C12 ACPs then the fatty alcohol composition produced by a recombinant microbial cell according to the invention will predominantly comprise fatty alcohols having a carbon chain length of C12.

In some embodiments preferred TEs are those that are classified as TE from the Family TE14 in the ThYme database. These sequences may be downloaded from GenBank and UniProt databases (Nucleic Acid Res 201038: D142-D148).

Some nonlimiting examples of TEs that may be used include the "class I" and "class II" acyl-ACP TE fat genes (e.g. fatA or fatB genes and reference is made to A. Jones et al., 1995, Plant Cell 7:359-371). In particular, FatB are preferred TEs (e.g. plant acyl-ACP TEs) useful in the invention. In some embodiments, the TE may be a bacterial acyl-ACP TE. FatB may be obtained for example from *Umbellularia california* having Accession number Q41635; and AAA34215; *Ulmus Americana* having Accession number AAB71731, *Cuphea hookeriana* Accession numbers Q39513; AAC49269; AAC49269; and AAC72881; *Cinnamonum camphorum* having Accession number Q39473; AAC49151; and acyl-ACP thioesterases from *Cuphea palustris* (AAC49179; and U.S. Pat. No. 5,955,329). Other TEs include without limitation CnFatB (*Cocos nucifera*, e.g. JF338903; JF338904 and JF338905); ccFAT (*Cinnamomum camphora*); pdFat (*Parabacteroides distasonis*, ATCC 8503); gsFat (*Geobacillus* sp. Y412MC10); pvFAT (*Paenibacillus vortex* V453); pm FAT (*Parabacteroides merdae* ATCC 43184); cvFatB (*Cuphea viscosissima*, JF338906; JF338907; and JF338908); eoFat (*Elaeis oleifera*) AAD42220 (*Elaeis guineensis*) and mlFat (*Madhuca longofolia* var. *latifolia*).

In some embodiments, homologous or analogous TE genes will be used for the heterologous expression of a TE enzyme.

It is known that different acyl-ACP TE have different degrees of chain length specificity. In some preferred embodiments, the TE useful in the invention is a TE having a preference for cleaving chain lengths of any one of C12, C14 and/or C16 fatty acids from ACP. In some embodiments, having a preference for cleaving chain lengths of any one of C12, C14 and/or C16 fatty acids from ACP means that the thioester hydrolysis will produce fatty acids having at least 85% (such as at least 90%, 93%, 95%, 96% or more) of any one of C12, C14 and/or C16 carbon chain lengths.

In one embodiment, the TE is encoded by a gene comprising the polynucleotide sequence having at least 70% (at least 75%, 80%, 85%, 90%, 93%, 95%, 97%, 99%, and even 100%) sequence identity to the polynucleotide sequence of SEQ ID NO: 9 or SEQ ID NO: 34.

SEQ ID NO: 9 - Polynucleotide sequence encoding a thioesterase:
ATGACAATGATTACGCCGAGCTCTGAACTCACCCTTACGAAAGGGAATAA

AAGCTGGTCATCGACAGCTGTAGCTGCCGCTTTAGAGTGGAAACCAAAAC

CGAAATTACCTCAGCTTCTTGACGACCACTTCGGCCTGCATGGTTTAGTA

TTCCGCAGAACGTTTGCCATAAGAAGCTACGAAGTAGGACCAGATCGTTC

TACCTCTATACTTGCTGTGATGAATCATATGCAGGAAGCCACGTTAAATC

ACGCAAAGAGCGTCGGGATCCTTGGGGACGGATTCGGCACCACATTGGAA

ATGAGTAAGCGGGACCTGATGTGGGTTGTTCGTCGTACCCACGTAGCGGT

CGAACGGTATCCAACATGGGGCGATACTGTTGAAGTGGAGTGCTGGATTG

GCGCTTCCGGAAACAACGGAATGCGCAGAGATTTTCTGGTGCGGGACTGT

AAAACTGGGGAAATCTTAACGCGCTGTACCTCCCTGTCCGTTCTGATGAA

CACGCGTACCCGGAGATTAAGTACGATTCCGGACGAAGTCCGTGGTGAAA

TCGGTCCCGCTTTTATTGACAACGTGGCGGTAAAAGACGACGAGATCAAA

AAGTTGCAGAAATTGAACGATTCCACAGCAGATTACATACAGGGCGGTCT

TACGCCCCGTTGGAACGACTTGGATGTGAATCAGCACGTAAATAACCTTA

AATATGTGGCGTGGGTGTTCGAGACCGTTCCCGACTCTATTTTTGAAAGT

CACCACATTTCCAGCTTTACGCTGGAGTACAGACGCGAGTGTACGCGCGA

TTCCGTTTTACGTTCCCTCACCACGGTGTCTGGCGGATCTTCCGAAGCTG

GGTTAGTGTGTGATCACTTGCTGCAACTTGAAGGCGGAAGTGAAGTTCTT

CGGGCCCGCACGGAATGGCGTCCCAAACTGACCGATTCCTTCCGCGGAAT

ATCAGTAATTCCGGCCGAGCCGCGGGTATAA.

SEQ ID NO: 10 - TE Polypeptide sequence encoded by the polynucleotide sequence of SEQ ID NO: 9:
MTMITPSSELTLTKGNKSWSSTAVAAALEWKPKPKLPQLLDDHFGLHGLV

FRRTFAIRSYEVGPDRSTSILAVMNHMQEATLNHAKSVGILGDGFGTTLE

MSKRDLMWVVRRTHVAVERYPTWGDTVEVECWIGASGNNGMRRDFLVRDC

KTGEILTRCTSLSVLMNTRTRRLSTIPDEVRGEIGPAFIDNVAVKDDEIK

KLQKLNDSTADYIQGGLTPRWNDLDVNQHVNNLKYVAWVFETVPDSIFES

HHISSFTLEYRRECTRDSVLRSLTTVSGGSSEAGLVCDHLLQLEGGSEVL

RARTEWRPKLTDSFRGISVIPAEPRV

SEQ ID NO: 34 - Polynucleotide sequence encoding a thioesterase "BTE":
ATGACCTTAGAGTGGAAACCAAAACCGAAATTACCTCAGCTTCTTGACGA

CCACTTCGGCCTGCATGGTTTAGTATTCCGCAGAACGTTTGCCATAAGAA

GCTACGAAGTAGGACCAGATCGTTCTACCTCTATACTTGCTGTGATGAAT

CATATGCAGGAAGCCACGTTAAATCACGCAAAGAGCGTCGGGATCCTTGG

GGACGGATTCGGCACCACATTGGAAATGAGTAAGCGGGACCTGATGTGGG

TTGTTCGTCGTACCCACGTAGCGGTCGAACGGTATCCAACATGGGGCGAT

ACTGTTGAAGTGGAGTGCTGGATTGGCGCTTCCGGAAACAACGGAATGCG

CAGAGATTTTCTGGTGCGGGACTGTAAAACTGGGGAAATCTTAACGCGCT

GTACCTCCCTGTCCGTTCTGATGAACACGCGTACCCGGAGATTAAGTACG

ATTCCGGACGAAGTCCGTGGTGAAATCGGTCCCGCTTTTATTGACAACGT

GGCGGTAAAAGACGACGAGATCAAAAAGTTGCAGAAATTGAACGATTCCA

CAGCAGATTACATACAGGGCGGTCTTACGCCCCGTTGGAACGACTTGGAT

GTGAATCAGCACGTAAATAACCTTAAATATGTGGCGTGGGTGTTCGAGAC

CGTTCCCGACTCTATTTTTGAAAGTCACCACATTTCCAGCTTTACGCTGG

AGTACAGACGCGAGTGTACGCGCGATTCCGTTTTACGTTCCCTCACCACG

GTGTCTGGCGGATCTTCCGAAGCTGGGTTAGTGTGTGATCACTTGCTGCA

ACTTGAAGGCGGAAGTGAAGTTCTTCGGGCCCGCACGGAATGGCGTCCCA

AACTGACCGATTCCTTCCGCGGAATATCAGTAATTCCGGCCGAGCCGCGG

GTATAA

SEQ ID NO: 35 - TE Polypeptide sequence encoded by the polynucleotide sequence of SEQ ID NO: 34:
MTLEWKPKPKLPQLLDDHFGLHGLVFRRTFAIRSYEVGPDRSTSILAVMN

HMQEATLNHAKSVGILGDGFGTTLEMSKRDLMWVVRRTHVAVERYPTWGD

TVEVECWIGASGNNGMRRDFLVRDCKTGEILTRCTSLSVLMNTRTRRLST

IPDEVRGEIGPAFIDNVAVKDDEIKKLQKLNDSTADYIQGGLTPRWNDLD

VNQHVNNLKYVAWVFETVPDSIFESHHISSFTLEYRRECTRDSVLRSLTT

VSGGSSEAGLVCDHLLQLEGGSEVLRARTEWRPKLTDSFRGISVIPAEPR

V

In some embodiments, the TE enzyme will comprise at least 70% (at least 75%, 80%, 85%, 90%, 93%, 95%, 97%, 99%, and even 100%) sequence identity to the polypeptide sequence of SEQ ID NO: 10 or SEQ ID NO: 35. In some embodiments, the TE gene will comprise at least 85% sequence identity to the polynucleotide sequence of SEQ ID NO: 9 or SEQ ID NO: 34. In some embodiments, the TE enzyme will comprise at least 85% sequence identity to the polypeptide sequence of SEQ ID NO: 10 or SEQ ID NO: 35. In some embodiments, the TE gene will comprise at least 97% sequence identity to the polynucleotide sequence of SEQ ID NO: 9 or SEQ ID NO: 34. In some embodiments, the TE enzyme will comprise at least 97% sequence identity to the polypeptide sequence of SEQ ID NO: 10 or SEQ ID NO: 35. In some embodiments, the TE gene will comprise at least 99% sequence identity to the polynucleotide sequence of SEQ ID NO: 9 or SEQ ID NO: 34. In some embodiments, the TE enzyme will comprise at least 99% sequence identity to the polypeptide sequence of SEQ ID NO: 10 or SEQ ID NO: 35. In some embodiments, the TE gene will comprise the polynucleotide sequence of SEQ ID NO: 9 or SEQ ID NO: 34. In some embodiments, the TE enzyme will comprise the polypeptide sequence of SEQ ID NO: 10 or SEQ ID NO: 34. In some embodiments the gene encoding the TE enzyme is derived from *Umbelluria californica* (California Bay "CaBay" or "BTE") and in other embodiments the gene encoding the TE enzyme is derived from *Cinnamomum camphorum*.

In some embodiments, the TE enzyme will be a functional fragment of a native TE, such as a TE having deletions at the N-terminal amino acid positions. In certain embodiments, the functional fragment will comprise at least 90% (at least 93%, at least 95%, at least 97% and at least 99%) of the reference enzyme. In certain embodiments, the functional fragment will include a deletion of at least 1, 2, 3, 4, 5, 6, 7, 8, 9, 10 or more amino acid residues. In some embodiments, the TE is a variant enzyme having at least 1, at least 5, at least 10, at least 15 or more amino acid modifications, such as substitutions. Non-limiting examples include the TE FatB genes from California Bay, *Cinnamomun camphora*, or from various *Cuphea* species such as those disclosed in WO 2011/008565 and reference is made to SEQ ID NOs. 21, 48, 52, 56, 60, 64, 66, 70, 72, 76, 80, 82, 86, 90, 92, 94, 96 and 100 described therein.

Further acyl-ACP TEs that are useful according to the invention are described in the following references: U.S. Pat. No. 5,344,771; U.S. Pat. No. 5,512,482; U.S. Pat. No. 6,150,512; U.S. Pat. No. 5,723,761; U.S. Pat. No. 5,910,631 and WO2010/075483.

Various assays are known which can be used to test for TE activity in a recombinant microorganism transformed with a vector comprising a polynucleotide encoding a TE according to the invention (See, Voelker and Davies, 1994, J. Bacteriol. 76:7320).

2. Acyl-CoA Synthetase

As described above, the term "acyl-CoA synthetase" is used synonymously with ACS or acyl-CoA synthetase or FadD. These enzymes mediate the formation of acyl-CoA esters (See, FIG. 1). According to an embodiment of the invention, a microbial host cell is engineered to express a recombinant ACS. ACS that can be expressed to produce acyl-CoA includes the *E. coli* fadD gene comprising the polynucleotide sequence of SEQ ID NO: 7 which encodes the ACS comprising the polypeptide sequence of SEQ ID NO: 8.

SEQ ID NO: 7 - Polynucleotide sequence of E. coli fadD:
ATGAAGAAGGTTTGGCTTAACCGTTATCCCGCGGACGTTCCGACGGAGAT
CAACCCTGACCGTTATCAATCTCTGGTAGATATGTTTGAGCAGTCGGTCG
CGCGCTACGCCGATCAACCTGCGTTTGTGAATATGGGGGAGGTAATGACC
TTCCGCAAGCTGGAAGAACGCAGTCGCGCGTTTGCCGCTTATTTGCAACA
AGGGTTGGGGCTGAAGAAAGGCGATCGCGTTGCGTTGATGATGCCTAATT
TATTGCAATATCCGGTGGCGCTGTTTGGCATTTTGCGTGCCGGGATGATC
GTCGTAAACGTTAACCCGTTGTATACCCCGCGTGAGCTTGAGCATCAGCT
TAACGATAGCGGCGCATCGGCGATTGTTATCGTGTCTAACTTTGCTCACA
CACTGGAAAAAGTGGTTGATAAAACCGCCGTTCAGCACGTAATTCTGACC
CGTATGGGCGATCAGCTATCTACGGCAAAAGGCACGGTAGTCAATTTCGT
TGTTAAATACATCAAGCGTTTGGTGCCGAAATACCATCTGCCAGATGCCA
TTTCATTTCGTAGCGCACTGCATAACGGCTACCGGATGCAGTACGTCAAA
CCCGAACTGGTGCCGGAAGATTTAGCTTTTCTGCAATACACCGGCGGCAC
CACTGGTGTGGCGAAAGGCGCGATGCTGACTCACCGCAATATGCTGGCGA
ACCTGGAACAGGTTAACGCGACCTATGGTCCGCTGTTGCATCCGGGCAAA
GAGCTGGTGGTGACGGCGCTGCCGCTGTATCACATTTTTGCCCTGACCAT
TAACTGCCTGCTGTTTATCGAACTGGGTGGGCAGAACCTGCTTATCACTA
ACCCGCGCGATATTCCAGGGTTGGTAAAAGAGTTAGCGAAATATCCGTTT
ACCGCTATCACGGGCGTTAACACCTTGTTCAATGCGTTGCTGAACAATAA
AGAGTTCCAGCAGCTGGATTTCTCCAGTCTGCATCTTTCCGCAGGCGGTG
GGATGCCAGTGCAGCAAGTGGTGGCAGAGCGTTGGGTGAAACTGACCGGA
CAGTATCTGCTGGAAGGCTATGGCCTTACCGAGTGTGCGCCGCTGGTCAG
CGTTAACCCATATGATATTGATTATCATAGTGGTAGCATCGGTTTGCCGG
TGCCGTCGACGGAAGCCAAACTGGTGGATGATGATGATAATGAAGTACCA
CCAGGTCAACCGGGTGAGCTTTGTGTCAAAGGACCGCAGGTGATGCTGGG
TTACTGGCAGCGTCCCGATGCTACCGATGAAATCATCAAAAATGGCTGGT
TACACACCGGCGACATCGCGGTAATGGATGAAGAAGGATTCCTGCGCATT
GTCGATCGTAAAAAAGACATGATTCTGGTTTCCGGTTTTAACGTCTATCC
CAACGAGATTGAAGATGTCGTCATGCAGCATCCTGGCGTACAGGAAGTCG
CGGCTGTTGGCGTACCTTCCGGCTCCAGTGGTGAAGCGGTGAAAATCTTC
GTAGTGAAAAAAGATCCATCGCTTACCGAAGAGTCACTGGTGACTTTTTG
CCGCCGTCAGCTCACGGGATACAAAGTACCGAAGCTGGTGGAGTTTCGTG
ATGAGTTACCGAAATCTAACGTCGGAAAAATTTTGCGACGAGAATTACGT
GACGAAGCGCGCGGCAAAGTGGACAATAAAGCCTAA SEQ ID NO: 8 - Polypeptide sequence of acyl-CoA synthetase encoded by the fadD polynucleotide sequence of SEQ ID NO: 7:
MKKVWLNRYPADVPTEINPDRYQSLVDMFEQSVARYADQPAFVNMGEVMT
FRKLEERSRAFAAYLQQGLGLKKGDRVALMMPNLLQYPVALFGILRAGMI
VVNVNPLYTPRELEHQLNDSGASAIVIVSNFAHTLEKVVDKTAVQHVILT
RMGDQLSTAKGTVVNFVVKYIKRLVPKYHLPDAISFRSALHNGYRMQYVK -continued

PELVPEDLAFLQYTGGTTGVAKGAMLTHRNMLANLEQVNATYGPLLHPGK

ELVVTALPLYHIFALTINCLLFIELGGQNLLITNPRDIPGLVKELAKYPF

TAITGVNTLFNALLNNKEFQQLDFSSLHLSAGGGMPVQQVVAERWVKLTG

QYLLEGYGLTECAPLVSVNPYDIDYHSGSIGLPVPSTEAKLVDDDDNEVP

PGQPGELCVKGPQVMLGYWQRPDATDEIIKNGWLHTGDIAVMDEEGFLRI

VDRKKDMILVSGFNVYPNEIEDVVMQHPGVQEVAAVGVPSGSSGEAVKIF

VVKKDPSLTEESLVTFCRRQLTGYKVPKLVEFRDELPKSNVGKILRRELR

DEARGKVDNKA

In some embodiments, the fadD gene will comprise at least 70%, (at least 75%, at least 80%, at least 85%, at least 90%, at least 93%, at least 95%, at least 97%, at least 99%, and even 100%) sequence identity to the polynucleotide sequence of SEQ ID NO: 7. In some embodiments, the ACS enzyme will comprise at least 70%, (at least 75%, at least 80%, at least 85%, at least 90%, at least 93%, at least 95%, at least 97%, at least 99%, and even 100%) sequence identity to the polypeptide sequence of SEQ ID NO: 8. In some embodiments, the fadD gene will comprise at least 85% sequence identity to the polynucleotide sequence of SEQ ID NO: 7. In some embodiments, the ACS enzyme will comprise at least 85% sequence identity to the polypeptide sequence of SEQ ID NO: 8. In some embodiments, the fadD gene will comprise at least 97% sequence identity to the polynucleotide sequence of SEQ ID NO: 7. In some embodiments, the ACS enzyme will comprise at least 97% sequence identity to the polypeptide sequence of SEQ ID NO: 8. In some embodiments, the fadD gene will comprise the polynucleotide sequence of SEQ ID NO: 7. In some embodiments, the ACS enzyme will comprise the polypeptide sequence of SEQ ID NO: 8.

In some embodiments, fadD encodes an ACS variant enzyme having at least 1, at least 5, at least 10, at least 15 or more amino acid modifications, such as substitutions. Non-limiting examples include modifications to the gene encoding the ACS of SEQ ID NO: 8.

In some embodiments, homologous fadD genes will be used for the heterologous expression of an ACS enzyme to produce acyl-CoAs. These fadD genes include without limitation, fadD from *Acinetobacter* sp. NCBI ID YP_045024; fadD from *Haemophilus influenza* NCBI ID NP_438551; fadD from *Pseudomonas aeruginosa* NCBI ID_251989 and 251990; BH3101 from *Bacillus halodurans* NP_243969; yhfL from *Bacillus subtilis* NP_388908; and fadD from *Rhizobium etli* CFN NCBI ID_ 533919; fadD from *Marinobacter algicola* ZP_01892995; fadD from *Marinobacter aquaeolei* YP_958864; fadD from *Mycobacterium tuberculosis* NP_215722; fadD15 from *Mycobacterium tuberculosis* NP_216703; fadD19 from *Mycobacterium tuberculosis* YP_177983; fadD from *Rhodopseudomonas palustris* YP_00993712; fadD from *Pseudomonas fluorscens* PfO-1 YP_350081; fadD from *Pseudomonas putida* ACC77300; fadK from *E. coli* strain W ZP_07590374; putative fadK from *Salmonella typhimurium* LT2 NP_460316; and putative fadK from *Thermomonospora fusca* YP_290214.

3. FAR Enzymes and Polynucleotides

The engineered bacterial cells encompassed by the invention are modified to express a polynucleotide encoding a heterologous FAR. Polynucleotides encoding FAR enzymes are known in the art (See e.g., WO2011/008535; WO2011/019858; U.S. Ser. No. 13/171,138, US2010/02036; U.S. Pat. No. 7,332,311; U.S. Pat. No. 6,143,538 and Metz et al., 2000. Plant Physiol. 122:635-644).

In some embodiments the acyl-CoA is reduced to a fatty alcohol in a two-step process. An NAD(P)H dependent acyl-CoA reductase converts an acyl-CoA to a fatty aldehyde and then the fatty aldehyde is reduced to a fatty alcohol by a NAD(P)H dependent alcohol dehydrogenase. Enzymes involved in this two-step conversion include the enzymes Acr1 and YqhD. (See, Reiser and Somerville, J. Bacteriol. (1997) 179:2969; Ishige et al., Appl. Environ. Microbiol. (2000) 66:3481; Hofrander et al. (2011) FEBS Letters 585:3538-3543 and Kalscheuer et al., 2006, Appl. Environ. Microbiol. 72:1373).

Preferred fatty alcohol forming acyl-CoA reductases (FARs) useful in the present invention catalyze the direct reduction of acyl-CoA and/or acyl-ACP substrates to fatty alcohols wherein free fatty aldehydes are essentially not released as an intermediate. Essentially these FARs reduce acyl chains to fatty alcohols by one enzymatic step. Depending on the substrate chain length it is possible to have trace amounts of aldehydes produced and released. In the direct reduction process, FAR converts at least acyl-ACP substrates to a fatty alcohol end-product without the subsequent action of an alcohol dehydrogenase.

In some embodiments, the FAR is a prokaryotic enzyme. In some embodiments the FAR is derived from a species of *Marinobacter* including, but not limited to, *M. algicola, M. alkaliphilus, M. aquaeolei, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum, M. squalenivirans, and M. vinifirmus*, and equivalent and synonymous species thereof.

In certain embodiments, the FAR is derived from *M. algicola* strain DG893 and has an amino acid sequence that is at least about 70% identical, at least about 75%, at least about 80% identical, at least about 85% identical, at least about 90% identical, at least about 93% identical at least about 95% identical, at least about 97% identical, at least about 98% identical and/or at least about 99% identical to SEQ ID NO:2 and/or a functional fragment thereof. In another embodiment, the FAR enzyme has an amino acid sequence that is identical to SEQ ID NO:2. In certain embodiments, the FAR is a variant of the wild-type FAR of SEQ ID N0:2 for example a FAR having at least 90%, (91%, 92%, 93%, 94%, 95%, 96%, 97%, 98%, 99% and even 100%) sequence identity to SEQ ID NO: 4, SEQ ID NO: 6, SEQ ID NO: 37 or SEQ ID NO: 39. In some embodiments, the variant FAR is FAR-V1 comprising the amino acid sequence of SEQ ID NO: 4. In some embodiments, the variant FAR is FAR-V2 comprising the amino acids sequence of SEQ ID NO: 6. In some embodiments, the variant FAR is FAR-V3 comprising the amino acid sequence of SEQ ID NO: 37. In some embodiments the variant FAR is FAR-V4 comprising the amino acid sequence of SEQ ID NO: 39. In some embodiments, the FAR variants will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:2, SEQ ID NO: 4, SEQ ID NO: 6, SEQ ID NO: 37 or SEQ ID NO: 39.

SEQ ID NO: 1 - Polynucleotide sequence of a codon
optimized FAR from Marinobacter algicola DG893:
ATGGCTACTCAACAACAACAGAACGGTGCATCTGCATCCGGCGTCTTGGA

ACAACTTCGTGGAAAGCACGTTCTTATCACAGGTACTACCGGATTTTTGG

GCAAAGTGGTTCTGGAAAAGTTGATTCGTACTGTTCCGGATATTGGAGGT

ATTCATCTGCTGATTCGTGGCAATAAACGTCATCCAGCCGCTCGTGAACG

TTTCCTGAACGAAATTGCGTCCTCCTCCGTCTTCGAACGTTTGCGTCACG

ATGATAATGAAGCCTTCGAGACCTTCTTGGAAGAACGTGTTCACTGTATT

ACCGGTGAGGTTACTGAATCCCGTTTTGGTTTGACACCTGAACGTTTTCG

TGCTTTGGCCGGTCAGGTTGACGCTTTTATTAACAGCGCTGCAAGCGTGA

ACTTTCGTGAGGAATTGGATAAAGCCCTGAAAATCAACACCTTGTGTCTT

GAAAATGTTGCTGCTCTTGCAGAATTGAACTCCGCTATGGCGGTCATTCA

GGTTTCCACTTGTTACGTTAACGGTAAAAACTCCGGTCAAATTACCGAAT

CCGTCATTAAACCTGCTGGCGAATCCATTCCCCGTTCCACTGACGGTTAC

TACGAGATCGAAGAATTGGTCCATCTGTTGCAAGACAAGATTTCCGATGT

TAAAGCTCGTTACTCCGGCAAAGTTCTGGAGAAAAAATTGGTTGATTTGG

GTATTCGTGAGGCCAATAATTACGGATGGTCCGACACCTACACATTCACC

AAATGGTTGGGTGAACAACTGCTGATGAAGGCCTTGTCTGGTCGTTCTTT

GACTATTGTGCGTCCCTCTATTATTGAGTCCGCTTTGGAAGAACCTTCCC

CTGGTTGGATCGAAGGCGTTAAAGTTGCCGATGCCATTATCTTGGCTTAT

GCCCGTGAAAAAGTTAGCCTGTTCCCTGGAAAACGTTCCGGCATTATTGA

TGTTATTCCTGTCGATTTGGTTGCGAACTCCATCATCTTGTCTCTGGCTG

AGGCGTTGTCTGGTTCTGGTCAACGTCGTATTTATCAATGTTGCAGCGGT

GGTTCTAATCCAATCTCCCTGGGTAAGTTCATTGATTATTTGATGGCCGA

GGCTAAGACCAACTATGCTGCCTACGATCAACTGTTTTATCGTCGTCCTA

CTAAACCTTTCGTCGCCGTGAACCGTAAATTGTTTGACGTTGTTGTTGGT

GGTATGCGTGTTCCTCTTTCTATTGCCGGTAAAGCTATGCGTTTGGCTGG

TCAAAATCGTGAGTTGAAAGTGCTTAAGAACCTTGATACGACCCGTTCCC

TTGCAACCATTTTTGGCTTCTATACTGCTCCCGACTATATCTTCCGTAAC

GATAGCTTGATGGCCCTGGCTTCTCGTATGGGTGAATTGGATCGTGTTCT

TTTCCCAGTTGATGCTCGTCAAATTGATTGGCAGTTGTACTTGTGTAAAA

TTCATTTGGGTGGTCTGAACCGTTACGCTTTGAAGGAACGTAAACTGTAT

TCTTTGCGTGCTGCTGATACTCGTAAAAAAGCTGCCTAA

SEQ ID NO: 2 - FAR polypeptide sequence encoded by
the polynucleotide sequence of SEQ ID NO: 1:
MATQQQQNGASASGVLEQLRGKHVLITGTTGFLGKVVLEKLIRTVPDIGG

IHLLIRGNKRHPAARERFLNEIASSSVFERLRHDDNEAFETFLEERVHCI

TGEVTESRFGLTPERFRALAGQVDAFINSAASVNFREELDKALKINTLCL

ENVAALAELNSAMAVIQVSTCYVNGKNSGQITESVIKPAGESIPRSTDGY

YEIEELVHLLQDKISDVKARYSGKVLEKKLVDLGIREANNYGWSDTYTFT

KWLGEQLLMKALSGRSLTIVRPSIIESALEEPSPGWIEGVKVADAIILAY

AREKVSLFPGKRSGIIDVIPVDLVANSIILSLAEALSGSGQRRIYQCCSG

GSNPISLGKFIDYLMAEAKTNYAAYDQLFYRRPTKPFVAVNRKLFDVVVG

GMRVPLSIAGKAMRLAGQNRELKVLKNLDTTRSLATIFGFYTAPDYIFRN

DSLMALASRMGELDRVLFPVDARQIDWQLYLCKIHLGGLNRYALKERKLY

SLRAADTRKKAA

SEQ ID NO: 3 - Polynucleotide Sequence of the
nucleic acid encoding FAR-V1:
CCATGGCGACTCAACAACAGCAGAACGGTGCATCTGCATCCGGCGTCTTG

GAACAACTTCGTGGAAAGCACGTTCTTATCACAGGTACTACCGGATTTTT

GGGCAAAGTGGTTCTGGAAAAGTTGATTCGTACTGTTCCGGATATTGGAG

GTATTCATCTGCTGATTCGTGGCAATAAACGTCATCCAGCCGCTCGTGAA

CGTTTCCTGAACGAAATTGCGTCCTCCTCCGTCTTCGAACGTTTGCGTCA

CGATGATAATGAAGCCTTCGAGACCTTCTTGGAAGAACGTGTTCACTGTA

TTACCGGTGAGGTTACTGAATCCCGTTTTGGTTTGACACCTGAGCGTTTT

CGTGCTTTGGCCGGTCAGGTTGACGCTTTTATTAACAGCGCTGCAAGCGT

GAGTTTTCGTGAGCAATTGGATAAAGCCCTGAAAATCAACACCTTGTGTC

TTGAAAATGTTGCTGCTCTTGCAGAATTGAACTCCGCTATGGCGGTCATT

CAGGTTTCCACTTGTTACGTTAACGGTAAAAACTCCGGTCAAATTACCGA

ATCCGTCATTAAATCGGCTGGCGAATCCATTCCCCGTTCCACTGACGGTT

ACTACGAGATCGAAGAATTGGTCCATCTGTTGCAAGACAAGATTTCCGAT

GTTAAAGCTCGTTACTCCGGCAAAGTTCTGGAGAAAAAATTGGTTGATTT

GGGTATTCGTGAGGCCAATAATTACGGATGGTCCGACACCTACACATTCA

CCAAATGGTTGGGTGAACAACTGCTGATGAAGGCCTTGTCTGGTCGTTCT

TTGACTATTGTGCGTCCCTCTATTATTGAGTCCGCTTTGGAAGAACCTTC

CCCTGGTTGGATCGAAGGCGTTAAAGTTGCCGATGCCATTATCTTGGCTT

ATGCCCGTGAAAAAGTTAGCCTGTTCCCTGGAAAACGTTCCGGCATTATT

GATGTTATTCCTGTCGATTTGGTTGCGAACTCCATCATCTTGTCTCTGGC

TGAGGCGTTGTCTGGTTCTGGTCAACGTCGTATTTATCAATGTTGCAGCG

GTGGTTCTAATCCAATCTCCCTGGGTAAGTTCATTGATTATTTGATGGCC

GAGGCTAAGACCAACTATGCTGCCTACGATCAACTGTTTTATCGTCGTCC

TACTAAACCTTTCGTCGCCGTGAACCGTAAATTGTTTGACGTTGTTGTTG

GTGGTATGCGTGTTGTCCTTTCTATTGCCGGTAAAGCTATGCGTTTGGCT

GGTGTAAATCGTGAGTTGAAAGTGCTTAAGAACCTTGATACGACCCGTAA

ACTTGCAACCATTTTTGGCTTCTATACTGCTCCCGACTATATCTTCCGTA

ACGATAGCTTGATGGCCCTGGCTCAGCGTATGGGTGAATTGGATCGTGTT

CTTTTCCCAGTTGATGCTCGTCAAATTGATTGGCAGTTGTACTTGTGTAA

AATTCATTTGGGTGGTCTGAACCGTTACGCTTTGAAGGAACGTAAACTGT

ATTCTTCGCGTGCTGCTGATACTGACGATAAAACCGCCTAAGTCGAC

SEQ ID NO: 4 - FAR-V1 polypeptide sequence encoded
by the polynucleotide sequence of SEQ ID NO: 3:
MATQQQQNGASASGVLEQLRGKHVLITGTTGFLGKVVLEKLIRTVPDIGG

IHLLIRGNKRHPAARERFLNEIASSSVFERLRHDDNEAFETFLEERVHCI

TGEVTESRFGLTPERFRALAGQVDAFINSAASVSFREQLDKALKINTLCL

ENVAALAELNSAMAVIQVSTCYVNGKNSGQITESVIKSAGESIPRSTDGY

YEIEELVHLLQDKISDVKARYSGKVLEKKLVDLGIREANNYGWSDTYTFT
KWLGEQLLMKALSGRSLTIVRPSIIESALEEPSPGWIEGVKVADAIILAY
AREKVSLFPGKRSGIIDVIPVDLVANSIILSLAEALSGSGQRRIYQCCSG
GSNPISLGKFIDYLMAEAKTNYAAYDQLFYRRPTKPFVAVNRKLFDVVVG
GMRVVLSIAGKAMRLAGVNRELKVLKNLDTTRKLATIFGFYTAPDYIFRN
DSLMALAQRMGELDRVLFPVDARQIDWQLYLCKIHLGGLNRYALKERKLY
SSRAADTDDKTA

SEQ ID NO: 5 - Polynucleotide sequence of the
nucleic acid encoding FAR-V2:
ATGGCGACTCAACAACAGAACAACGGTGCATCTGCATCCGGCGTCTTGGA
AATTCTTCGTGGAAAGCACGTTCTTATCACAGGTACTACCGGATTTTTGG
GCAAAGTGGTTCTGGAAAAGTTGATTCGTACTGTTCCGGATATTGGAGGT
ATTCATCTGCTGATTCGTGGCAATAAACGTCATCCAGCCGCTGGCGAACG
TTTCCTGAACGAAATTGCGTCCTCCTCCGTCTTCGAACGTTTGCGTCACG
ATGATAATGAAGCCTTCGAGACCTTCTTGGAAGAACGTGTTCACTGTATT
ACCGGTGAGGTTACTGAATCCCGTTTTGGTTTGACACCTGAGCGTTTTCG
TGCTTTGGCCGGTCAGGTTGACGCTTTTATTCATAGCGCTGCAAGCGTGA
ACTTTCGTGAGCAATTGGATAAAGCCCTGAAAATCAACACCTTGTGTCTT
GAAAATGTTGCTGCTCTTGCAGAATTGAACTCCGCTATGGCGGTCATTCA
GGTTTCCACTTGTTACGTTAACGGTAAAACCTCCGGTCAAATTACCGAAT
CCGTCATTAAATCGGCTGGCGAATCCATTCCCCGTTCCACTGACGGTTAC
TACGAGATCGAAGAATTGGTCCATCTGTTGCAAGACAAGATTTCCGATGT
TAAAGCTCGTTACTCCGGCCGTGTTATGGGGAAAAAATTGGTTGATTTGG
GTATTCGTGAGGCCAATAATTACGGATGGTCCGACACCTACACATTCACC
AAATGGTTGGGTGAACAACTGCTGATGAAGGCCTTGTCTGGTCGTTCTTT
GACTATTGTGCGTCCCTCTATTATTGAGTCCGCTTTGGAAGAACCTTCCC
CTGGTTGGATCGAAGGCGTTAAAGTTGCCGATGCCATTATCTTGGCTTAT
GCCCGTGAAAAAGTTAGCCTGTTCCCTGGAAAACGTTCCGGCATTATTGA
TGTTATTCCTGTCGATTTGGTTGCGAACTCCATCATCTTGTCTCTGGCTG
AGGCGTTGTCTGGTTCTGGTCAACGTCGTATTTATCAATGTTGCAGCGGT
GGTTCTAATCCAATCTCCCTGGGTAAGTTCATTGATTATTTGAACGCCGA
GGCTAAGACCAACTATGCTGCCTACGATCAACTGTTTTATCGTCGTCCTA
CTAAACCTTTCGTCGCCGTGAACCGTAAATTGTTTGACGTTGTTGTTGGT
GTCATGCGTGTTGTCCTTTCTATTGCCGGTAAAGCTATGCGTTTGGCTGG
TGTAAATCGTGAGTTGAAAGTGCTTAAGAACCTTGATACGACCCGTAAAC
TTGCAACCATTTTTGGCTTCTATACTGCTCCCGACTATATCTTCCGTAAC
GATAGCTTGATGGCCCTGGCTCAGCGTATGGGTGAATTGGATCGTGTTCT
TTTCCCAGTTGATGCTCGTCAAATTGATTGGCAGTTGTACTTGTGTAAAA
TTCATTTGCGTGGTCTGAACCGTTACGCTTTGAAGGAACGTAAACTGTAT
TCTTCGCGTGCTGCTGATACTGACGATAAAACCGCCTAA SEQ ID NO: 6 - FAR-V2 polypeptide sequence encoded
by the polynucleotide sequence of SEQ ID NO: 5:
MATQQQNNGASASGVLEILRGKHVLITGTTGFLGKVVLEKLIRTVPDIGG IHLLIRGNKRHPAAGERFLNEIASSSVFERLRHDDNEAFETFLEERVHCI
TGEVTESRFGLTPERFRALAGQVDAFIHSAASVNFREQLDKALKINTLCL
ENVAALAELNSAMAVIQVSTCYVNGKTSGQITESVIKSAGESIPRSTDGY
YEIEELVHLLQDKISDVKARYSGRVMGKKLVDLGIREANNYGWSDTYTFT
KWLGEQLLMKALSGRSLTIVRPSIIESALEEPSPGWIEGVKVADAIILAY
AREKVSLFPGKRSGIIDVIPVDLVANSIILSLAEALSGSGQRRIYQCCSG
GSNPISLGKFIDYLNAEAKTNYAAYDQLFYRRPTKPFVAVNRKLFDVVVG
VMRVVLSIAGKAMRLAGVNRELKVLKNLDTTRKLATIFGFYTAPDYIFRN
DSLMALAQRMGELDRVLFPVDARQIDWQLYLCKIHLRGLNRYALKERKLY
SSRAADTDDKTA SEQ ID NO: 36 - Polynucleotide sequence encoding
the FAR-V3 amino acid sequence of SEQ ID NO: 37:
ATGGCGACTCAACAACAGAACAACGGTGCATCTGCATCCGGCGTCTTGGA
AATTCTTCGTGGAAAGCACGTTCTTATCACAGGTACTACCGGATTTTTGG
GCAAAGTGGTTCTGGAAAAGTTGATTCGTACTGTTCCGGATATTGGAGGT
ATTCATCTGCTGATTCGTGGCAATAAACGTCATCCAGCCGCTCGCGAACG
TTTCCTGAACGAAATTGCGTCCTCCTCCGTCTTCGAACGTTTGCGTCACG
ATGATAATGAAGCCTTCGAGACCTTCTTGGAAGAACGTGTTCACTGTATT
ACCGGTGAGATTACTGAATCCCGTTTTGGTTTGACACCTGAGCGTTTTCG
TGCTTTGGCCGGTCAGGTTGACGCTTTTATTCATAGCGCTGCAAGCGTGA
ACTTTCGTGAGCAATTGGATAAAGCCCTGAAAATCAACACCTTGTGTCTT
GAAAATGTTGCTGCTCTTGCAGAATTGAACTCCGCTATGGCGGTCATTCA
GGTTTCCACTTGTTACGTTAACGGTAAAACCTCCGGTCAAATTACCGAAT
CCGTCATTAAATCGGCTGGCGAATCCATTCCCCGTTCCACTGACGGTTAC
TACGAGATCGAAGAATTGGTCCATCTGTTGCAAGACAAGATTTCCGATGT
TAAAGCTCGTTACTCCGGCCGTGTTATGGGGAAAAAATTGGTTGATTTGG
GTATTCGTGAGGCCAATAATTACGGATGGTCCGACACCTACACATTCACC
AAATGGTTGGGTGAACAACTGCTGATGAAGGCCTTGTCTGGTCGTTCTTT
GACTATTGTGCGTCCCTCTATTATTGAGTCCGCTTTGGAAGAACCTTCCC
CTGGTTGGATCGAAGGCGTTAAAGTTGCCGATGCCATTATCTTGGCTTAT
GCCCGTGAAAAAGTTAGCCTGTTCCCTGGAAAACGTTCCGGCATTATTGA
TGTTATTCCTGTCGATTTGGTTGCGAACTCCATCATCTTGTCTCTGGCTG
AGGCGTTGTCTGGTTCTGGTCAACGTCGTATTTATCAATGTTGCAGCGGT
GGTTCTAATCCAATCTCCCTGGGTAAGTTCATTGATTATTTGAACGCCGA
GGCTAAGACCAACTATGCTGCCTACGATCAACTGTTTTATCGTCGTCCTA
CTAAACCTTTCGTCGCCGTGAACCGTAAATTGTTTGACGTTGTTGTTGGT
GTCATGCGTGTTGTCCTTTCTATTGCCCGCAAAGCTATGCGTTTGGCTGG
TGTAAATCGTGAGTTGAAAGTGCTTAAGAACCTTGATACGACCCGTAAAC
TTGCAACCATTTTTGGCTTCTATACTGCTCCCGACTATATCTTCCGTAAC
GATAGCTTGATGGCCCTGGCTCAGCGTATGGGTGAATTGGATCGTGTTCT
TTTCCCAGTTGATGCTCGTCAAATTGATTGGCAGTTGTACTTGTGTAAAA

```
TTCATTTGCGTGGTCTGAACCGTTACGCTTTGAAGGAACGTAAACTGTAT

TCTTCGCGTGCTGCTGATACTGACGATAAAACCGCCTAA

SEQ ID NO: 37 - Polypeptide sequence of FAR-V3:
MATQQQNNGASASGVLEILRGKHVLITGTTGFLGKVVLEKLIRTVPDIGG

IHLLIRGNKRHPAARERFLNEIASSSVFERLRHDDNEAFETFLEERVHCI

TGEITESRFGLTPERFRALAGQVDAFIHSAASVNFREQLDKALKINTLCL

ENVAALAELNSAMAVIQVSTCYVNGKTSGQITESVIKSAGESIPRSTDGY

YEIEELVHLLQDKISDVKARYSGRVMGKKLVDLGIREANNYGWSDTYTFT

KWLGEQLLMKALSGRSLTIVRPSIIESALEEPSPGWIEGVKVADAIILAY

AREKVSLFPGKRSGHDVIPVDLVANSHLSLAEALSGSGQRRIYQCCSGGS

NPISLGKFIDYLNAEAKTNYAAYDQLFYRRPTKPFVAVNRKLFDVVVGVM

RVVLSIARKAMRLAGVNRELKVLKNLDTTRKLATIFGFYTAPDYIFRNDS

LMALAQRMGELDRVLFPVDARQIDWQLYLCKIHLRGLNRYALKERKLYSS

RAADTDDKTA

SEQ ID NO: 38 - Polynucleotide sequence encoding
the FAR-V4 amino acid sequence of SEQ ID NO: 39:
ATGGCGACTTATCAACGTAACAACGGTGCATCTGCATCCGGCGTCTTGGA

AATTCTTCGTGGAAAGCACGTTCTTATCACAGGTACTACCGGATTTTTGG

GCAAAGTGGTTCTGGAAAAGTTGATTCGTACTGTTCCGGATATTGGAGGT

ATTCATCTGCTGATTCGTGGCAATAAACGTCATCAGGCCGCTCGCGAACG

TTTCCTGAACGAAATTGCGTCCTCCTCCGTCTTCGAACGTTTGCGTCACG

ATGATAATGAAGCCTTCGAGACCTTCTTGGAAGAACGTGTTCACTGTATT

ACCGGTGAGATTACTGAATCCCATTTTGGTTTGACACCTGAGCGTTTTCG

TGCTTTGGCCGGTCAGGTTGACGCTTTTATTCATAGCGCTGCAAGCGTGA

ACTTTCGTGAGCAATTGGATAAAGCCCTGAAAATCAACACCTTGTGTCTT

GAAAATGTTGCTGCACTTGCAGAATTGAACTCCGCTATGGCGGTCATTCA

GGTTTCCACTTGTTACGTTAACGGTAAAACCTCCGGTCAAATTACCGAAT

CCGTCATTAAATCGGCTGGCGAATCCATTCCCCGTTCCACTGACGGTTAC

TACGAGATCGAAGAATTGGTCCATCTGTTGCAAGACAAGATTTCCGATGT

TAAAGCTCGTTACTCCGGCCGTGTTATGGGGAAAAAATTGGTTGATTTGG

GTATTCGTGAGGCCAATAATTACGGATGGTCCGACACCTACACATTCACC

AAATGGTTGGGTGAACAACTGCTGATGAAGGCCTTGTCTGGTCGTTCTTT

GACTATTGTGCGTCCCTCTATTATTGAGTCCGCTTTGGAAGAACCTTCCC

CTGGTTGGATCGAAGGCGTTAAAGTTGCCGATGCCATTATCTTGGCTTAT

GCCCGTGAAAAAGTTAGCCTGTTCCCTGGAAAACGTTCCGGCATTCTGGA

TTTTATTCCTGTCGATTTGGTTGCGAACTCCATCATCTTGTCTCTGGCTG

AGGCGTTGTCTGGTTCTGGTCAACGTCGTATTTATCAATGTTGCAGCGGT

GGTTCTAATCCACTGTCCCTGGGTAAGTTCTTTGATTATTTGAACGCCGA

GGCTAAGACCAACTATGCTGCCTACGATCAACTGTTTTATCGTCGTCCTA

CTAAACCTTTCGTCGCCGTGAACCGTAAATTGTTTGACGTTGTTGTTGGT

GTCATGCGTGTTGTCCTTTCTATTGCCCATAAAGCTATGCGTTTGGCTGG

TGTAAATCGTGAGTTGAAAGTGCTTAAGAACCTTGATACGACCCGTAAAC

TTGCAACCATTTTTGGCTTCTATACTGCTCCCGACTATATCTTCCGTAAC

GATAGCTTGATGGCCCTGGCTCAGCGTATGGGTGAATTGGATCGTGTTCT

TTTCCCAGTTGATGCTCGTCAAATTGATTGGCAGTTGTACTTGTGTAAAA

TTCATTTGCGTGGTCTGAACCGTTACGCTTTGAAGGGCCGTAAACTGTAT

TCTTCGCGTGCTGCTGATCATGACGATGAAATTGCCTAA

SEQ ID NO: 39 - Polypeptide sequence of FAR-V4:
MATYQRNNGASASGVLEILRGKHVLITGTTGFLGKVVLEKLIRTVPDIGG

IHLLIRGNKRHQAARERFLNEIASSSVFERLRHDDNEAFETFLEERVHCI

TGEITESHFGLTPERFRALAGQVDAFIHSAASVNFREQLDKALKINTLCL

ENVAALAELNSAMAVIQVSTCYVNGKTSGQITESVIKSAGESIPRSTDGY

YEIEELVHLLQDKISDVKARYSGRVMGKKLVDLGIREANNYGWSDTYTFT

KWLGEQLLMKALSGRSLTIVRPSIIESALEEPSPGWIEGVKVADAIILAY

AREKVSLFPGKRSGILDFIPVDLVANSIILSLAEALSGSGQRRIYQCCSG

GSNPLSLGKFFDYLNAEAKTNYAAYDQLFYRRPTKPFVAVNRKLFDVVVG

VMRVVLSIAHKAMRLAGVNRELKVLKNLDTTRKLATIFGFYTAPDYIFRN

DSLMALAQRMGELDRVLFPVDARQIDWQLYLCKIHLRGLNRYALKGRKLY

SSRAADHDDEIA
```

In certain embodiments, the FAR is derived from *Marinobacter aquaeolei* and has an amino acid sequence that is at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ID NO: 5 as disclosed in WO 2012/006114 and/or a functional fragment thereof. In another specific embodiment, the FAR enzyme has an amino acid sequence that is identical to SEQ ID NO: 5. In certain embodiments, the FAR is a variant of the wild-type FAR of SEQ ID NO:5 that has at least 1, at least 2, at least 3, at least 4, at least 5, at least 6, at least 7, at least 8, at least 9, at least 10, at least 12, at least 14, at least 16, at least 18, at least 20, or more amino acid alterations (e.g., substitutions, deletions and/or insertions) relative to SEQ ID NO:5. In certain embodiments, the FAR is encoded by a polynucleotide sequence having at least 85% (at least 90%, 91%, 92%, 93%, 94%, 95%, 96%, 97%, 98%, 99% sequence identity to SEQ ID NO:4 as disclosed in WO 2012/006114.

In certain embodiments, the FAR is obtained from a marine bacterium selected from the group of *Neptuniibacter caesariensis* strain MED92 (also referred to as *Neptunibacterin* some publications), *Reinekea* sp. strain MED297, *Marinomonas* sp. strain MED121, unnamed gammaproteobacterium strain HTCC2207, and *Marinobacter* sp. strain ELB 17, as well as equivalents and synonymous species thereof. In certain embodiments, the FAR is obtained from the genus *Oceanobacter*. In some embodiments, the FAR is obtained from the *Oceanobacter* species strain RED65 (e.g. NCBI accession number ZP_01305629) and has an amino acid sequence that is at least about 70% identical, at least about 75% identical, at least about 80% identical, at least about 85% identical, at least about 90% identical, at least about 93% identical, at least about 95% identical, at least about 97% identical, at least about 98% identical and/or at least about 99% identical to SEQ ID NOs:6 and/or 8 as disclosed in WO 2011/008535.

In various embodiments, the FAR is encoded by a polynucleotide selected from the group of FAR_Hch (*Hahella chejuensis* KCTC 2396 GenBank YP_436183); FAR_Mac (from marine *Actinobacterium* strain PHSC20C1); FAR_JVC (JCVI_ORF_1096697648832, GenBank Accession No. EDD40059.1); FAR_Fer (JCVLS-CAF_1101670217388); FAR_Key (JCVLS-CAF_1097205236585; FAR_Gal (JCVLS-CAF_1101670289386); *Vitis vinifera* FAR (GenBank Accession No. CAO22305.1 or CAO67776.1); *Desulfatibacillum alkenivorans* FAR (GenBank Accession No. NZ_ABII01000018.1); *Stigmatella aurantiaca* FAR (NZ_AAMD01000005.1); *Phytophthora ramorum* FAR (GenBank Accession No.: AAQX01001105.1); GenBank Accession no. AAD38039.1; gi|5020215|gb|AAD38039.1|AF149917_1 acyl CoA reductase [*Simmondsia chinensis*]; GenBank Accession no. BAC79425.1; gi|33146307|dbj|BAC79425.1|fatty-acyl reductase [*Bombyx mori*]; GenBank Accession no. DQ446732.1 or NM_115529.1; gi|91806527|gb|DQ446732.1|*Arabidopsis thaliana* clone pENTR221-At3g44560; gi|18410556|ref|NM_115529.1|; and (GenBank Accession no. EU817405.1; gi|210063138|gb|EU817405.1|*Ostrinia scapulalis*.

As indicated herein, "heterologous FAR" encompasses wild-type FARs, variants and functional fragments thereof. In various embodiments, a functional fragment of a full-length wild-type FAR or a variant FAR comprises at least about 70%, at least about 75%, at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises about 75%, about 80%, about 85%, at about 90%, about 91%, about 92%, about 93%, about 94%, about 95%, about 96%, about 97%, about 98%, or about 99% of the amino acid sequence of a full-length FAR polypeptide (such as a FAR comprising at least 95% sequence identity to SEQ ID NO: 2, SEQ ID NO: 4, SEQ ID NO: 6, SEQ ID NO: 37 or SEQ ID NO: 39.

In another aspect, the present invention provides polynucleotides encoding FAR enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FAR polypeptide encompassed by the invention is coded for by a polynucleotide sequence that has been codon optimized. In particular embodiments, the polynucleotides that encode the FAR enzymes described herein are codon-optimized for expression in a host bacterial cell. Indeed, it is intended that the polynucleotides of the present invention be produced using any suitable methods and components as known in the art.

In some embodiments, a FAR enzyme is encoded by a polynucleotide sequence that has at least about 70%, at least about 75%, at least about 80%, at least about 85%, at least about 90%, at least about 93%, at least about 95%, at least about 96%, at least about 97%, or at least about 99% sequence identity to SEQ ID NO:1, SEQ ID NO:3, SEQ ID NO: 5, SEQ ID NO: 36 or SEQ ID NO:38 and further hybridizes with SEQ ID NO:1, SEQ ID NO:3, SEQ ID NO: 5, SEQ ID NO: 36 and/or SEQ ID NO: 38 under medium, medium-high, high or very high stringency conditions.

In some embodiments, the preferred substrates for the heterologous FAR are fatty acyl-ACP substrates comprising carbon chain lengths of C10 to C18. In certain embodiments, the fatty acyl-ACP substrates comprise carbon chain lengths of C12 to C16, and in other embodiments, the fatty acyl-ACP substrates comprise carbon chain lengths of C12 to C14. In certain embodiments, the substrate comprises a majority of saturated hydrocarbons. In certain embodiments, the substrate pool for the heterologous FAR comprises over about 70% (e.g., about 75%, about 80%, about 85%, about 88%, about 90%, about 92%, about 94%, about 95%, about 96%, about 97%, about 98%, and about 99%) C10 to C18 fatty acyl-ACP substrates; over about 70% (e.g., about 75%, about 80%, about 85%, about 88%, about 90%, about 92%, about 94%, about 95%, about 96%, about 97%, about 98%, and about 99%) C10 to C16 fatty acyl-ACP substrates and also over about 70% (e.g., about 75%, about 80%, about 85%, about 88%, about 90%, about 92%, about 94%, about 95%, about 96%, about 97%, about 98%, and about 99%) C12 to C16 fatty acyl-ACP substrates. In certain embodiments, the substrate pool for the heterologous FAR comprises over about 70% (e.g., about 75%, about 80%, about 85%, about 88%, about 90%, about 92%, about 94%, about 95%, about 96%, about 97%, about 98%, and about 99%) C10 to C18 fatty acyl-CoA substrates; over about 70% (e.g., about 75%, about 80%, about 85%, about 88%, about 90%, about 92%, about 94%, about 95%, about 96%, about 97%, about 98%, and about 99%) C10 to C16 fatty acyl-CoA substrates; and also over about 70% (e.g., about 75%, about 80%, about 85%, about 88%, about 90%, about 92%, about 94%, about 95%, about 96%, about 97%, about 98%, and about 99%) C12 to C16 fatty acyl-CoA substrates.

4. DNA Constructs, Vectors and Transformation

In some embodiments, polynucleotides encoding any of the enzymes as described herein (e.g., TE, FadD, or FAR) for expression in the recombinant host cells are operably linked to a promoter, and optionally, to other control sequences.

Suitable promoters include, but are not limited to constitutive promoters, regulated promoters, and inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art. See e.g., Nevoigt et al. (2006) *Appl. Environ. Microbiol.* 72:5266-5273, the disclosure of which is herein incorporated by reference in its entirety.

In certain embodiments, the DNA constructs, vectors and polynucleotides are suitable for expression of a heterologous FadD, TE or FAR enzyme in bacteria. For bacterial host cells, suitable promoters for directing transcription of the nucleic acid constructs of the present disclosure, include, but are not limited to the promoters obtained or derived the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (Villa-Kamaroff et al., *Proc. Natl Acad. Sci. USA* 75: 3727-3731 (1978)), as well as the tac promoter (DeBoer et al., *Proc. Natl Acad. Sci. USA* 80: 21-25 (1993)). Additional promoters include trp promoter, phage lambda PL, T7 promoter, promoters found at PromEC (margalit.huji.ac.il/promec/index.html) and the like. Particularly useful promoters include the Trc promoter (Brosius J. et al., (1985) J. Biol. Chem. 260: 3539-3541). Additional promoters suitable for use in the present disclosure are described in Terpe H., 2006, Appl. Microbiol. Biotechnol. 72:211-222 and in Sambrook et al (2001) *Molecular Cloning: A Laboratory Manual*, 3$^{rd}$ ed., Cold Spring Harbor Laboratory Press, New York.

In various embodiments, an expression vector optionally contains a ribosome binding site (RBS) for translation initiation, and a transcription terminator, such as the transcriptional terminators $T_1$ and $T_2$ derived from the rrnB operon from *E. coli* (See e.g., Orosz et al., (1991) Eur. J. Biochem. 201: 653-659). The vector also optionally includes appropriate sequences for amplifying expression, e.g., translational enhancers.

In various embodiments, the polynucleotides useful for expressing the heterologous enzymes in recombinant host cells are operably linked to other control sequences, including but not limited to, a transcription terminator sequence, a signal sequence that when translated directs the expressed polypeptide into the secretory pathway of the recombinant host cell, and/or a polyadenylation sequence (eukaryotes). The choice of appropriate control sequences for use in the polynucleotide constructs of the present disclosure is within the skill in the art and in various embodiments is dependent on the recombinant host cell used and the desired method of recovering the fatty alcohol compositions produced. Indeed, it is not intended that the present invention be limited to any particular control sequence(s).

A recombinant expression vector according to the invention can be any suitable vector, e.g., a plasmid or a virus, which can be manipulated by recombinant DNA techniques to facilitate expression of at least one heterologous enzyme in the recombinant host cell. In certain embodiments, the expression vector is integrated into the chromosome of the recombinant host cell and comprises one or more heterologous genes operably linked to one or more control sequences useful for production of at least one heterologous enzyme. In other embodiments, the expression vector is an extra chromosomal replicative DNA molecule, e.g., a linear or closed circular plasmid, that is found either in low copy number (e.g., from about 1 to about 10 copies per genome equivalent) or in high copy number (e.g., more than about 10 copies per genome equivalent). In various embodiments, the expression vector includes a selectable marker, such as a gene that confers antibiotic resistance (e.g., ampicillin, kanamycin, chloramphenicol or tetracycline resistance) to the recombinant host organism that comprises the vector.

Expression vectors which, in certain embodiments, are useful for expressing enzymes as disclosed herein (for example FadD, TE and FAR) are commercially available, e.g., from Sigma-Aldrich Chemicals, St. Louis Mo. and Stratagene, LaJolla Calif. In some embodiments, examples of suitable expression vectors are plasmids which are derived from pBR322 (Gibco BRL), pUC (Gibco BRL), pREP4, pCEP4 (Invitrogen) or pPoly (Lathe et al., 1987, Gene 57:193-201). In some embodiments, the expression vector encoding the FAR enzyme and the expression vector encoding a second enzyme such as TE or FadD are on separate vectors. In some other embodiments, the heterologous FAR enzyme and the second enzyme are encoded on the same expression vector, and expression of each enzyme is independently regulated by a different promoter. In some further embodiments, the heterologous FAR enzyme and the second enzyme are encoded on the same expression vector, and expression of each enzyme is regulated by the same promoter.

In certain embodiments, the present disclosure provides a plasmid for expression of heterologous genes in *E. coli*. Expression vector pCK110900, which comprises a P15A origin of replication "ori" (P15A ori), lac a CAP binding site, a lac promoter, a T7 ribosomal binding site (T7g10 RBS) and a chloramphenicol resistance gene (camR) is an exemplary vector that finds use in the present invention. This expression vector is depicted in FIG. 3 of U.S. Patent Publication No. 2006/0195947, which is incorporated herein by reference in its entirety. Other suitable plasmid vectors include, but are not limited to derivatives of pCL1920 and pCL1921 (Lerner and Inouye, 1990; NAR 18:4631). These vectors contain the pSC101 on and confer resistance to spectinomycin (GenBank:AB236930). In some embodiments, the vector is an expression vector derived from pCL1920 including the Trc promoter and the lacIq gene from *E. coli*. pLS8349 (SEQ ID NO: 15).

```
SEQ ID NO: 15 - Polynucleotide sequence of
pLS8379:
GGCATCCGCTTACAGACAAGCTGTGACCGTCTCCGGGAGCTGCATGTGTC

AGAGGTTTTCACCGTCATCACCGAAACGCGCGAGGCAGCAGATCAATTCG

CGCGCGAAGGCGAAGCGGCATGCATTTACGTTGACACCATCGAATGGTGC

AAAACCTTTCGCGGTATGGCATGATAGCGCCCGGAAGAGAGTCAATTCAG

GGTGGTGAATGTGAAACCAGTAACGTTATACGATGTCGCAGAGTATGCCG

GTGTCTCTTATCAGACCGTTTCCCGCGTGGTGAACCAGGCCAGCCACGTT

TCTGCGAAAACGCGGGAAAAAGTGGAAGCGGCGATGGCGGAGCTGAATTA

CATTCCCAACCGCGTGGCACAACAACTGGCGGGCAAACAGTCGTTGCTGA

TTGGCGTTGCCACCTCCAGTCTGGCCCTGCACGCGCCGTCGCAAATTGTC

GCGGCGATTAAATCTCGCGCCGATCAACTGGGTGCCAGCGTGGTGGTGTC

GATGGTAGAACGAAGCGGCGTCGAAGCCTGTAAAGCGGCGGTGCACAATC

TTCTCGCGCAACGCGTCAGTGGGCTGATCATTAACTATCCGCTGGATGAC

CAGGATGCCATTGCTGTGGAAGCTGCCTGCACTAATGTTCCGGCGTTATT

TCTTGATGTCTCTGACCAGACACCCATCAACAGTATTATTTTCTCCCATG

AAGACGGTACGCGACTGGGCGTGGAGCATCTGGTCGCATTGGGTCACCAG

CAAATCGCGCTGTTAGCGGGCCCATTAAGTTCTGTCTCGGCGCGTCTGCG

TCTGGCTGGCTGGCATAAATATCTCACTCGCAATCAAATTCAGCCGATAG

CGGAACGGGAAGGCGACTGGAGTGCCATGTCCGGTTTTCAACAAACCATG

CAAATGCTGAATGAGGGCATCGTTCCCACTGCGATGCTGGTTGCCAACGA

TCAGATGGCGCTGGGCGCAATGCGCGCCATTACCGAGTCCGGGCTGCGCG

TTGGTGCGGATATCTCGGTAGTGGGATACGACGATACCGAAGACAGCTCA

TGTTATATCCCGCCGTTAACCACCATCAAACAGGATTTTCGCCTGCTGGG

GCAAACCAGCGTGGACCGCTTGCTGCAACTCTCTCAGGGCCAGGCGGTGA

AGGGCAATCAGCTGTTGCCCGTCTCACTGGTGAAAAGAAAAACCACCCTG

GCGCCCAATACGCAAACCGCCTCTCCCCGCGCGTTGGCCGATTCATTAAT

GCAGCTGGCACGACAGGTTTCCCGACTGGAAAGCGGGCAGTGAGCGCAAC

GCAATTAATGTAAGTTAGCGCGAATTGATCTGGTTTGACAGCTTATCATC
```

```
GACTGCACGGTGCACCAATGCTTCTGGCGTCAGGCAGCCATCGGAAGCTG
TGGTATGGCTGTGCAGGTCGTAAATCACTGCATAATTCGTGTCGCTCAAG
GCGCACTCCCGTTCTGGATAATGTTTTTTGCGCCGACATCATAACGGTTC
TGGCAAATATTCTGAAATGAGCTGTTGACAATTAATCATCCGGCTCGTAT
AATGTGTGGAATTGTGAGCGGATAACAATTTCACACAGGAAACAGCGCCG
CTGAGAAAAGCGAAGCGGCACTGCTCTTTAACAATTTATCAGACAATCT
GTGTGGGCACTCGACCGGAATTATCGATTAACTTTATTATTAAAAATTAA
AGAGGTATATATTAATGTATCGATTAAATAAGGAGGAATAAACCATGGAT
CCGAGCTCGAGATCTGCAGCTGGTACCATATGGGAATTCGAAGCTTTCTA
GAACAAAAACTCATCTCAGAAGAGGATCTGAATAGCGCCGTCGACCATCA
TCATCATCATCATTGAGTTTAAACGGTCTCCAGCTTGGCTGTTTTGGCGG
ATGAGAGAAGATTTTCAGCCTGATACAGATTAAATCAGAACGCAGAAGCG
GTCTGATAAAACAGAATTTGCCTGGCGGCAGTAGCGCGGTGGTCCCACCT
GACCCCATGCCGAACTCAGAAGTGAAACGCCGTAGCGCCGATGGTAGTGT
GGGGTCTCCCCATGCGAGAGTAGGGAACTGCCAGGCATCAAATAAAACGA
AAGGCTCAGTCGAAAGACTGGGCCTTTCGTTTTATCTGTTGTTTGTCGGT
GAACGCTCTCCTGAGGCGCCTGATGCGGTATTTTCTCCTTACGCATCTGT
GCGGTATTTCACACCGCATATGGTGCACTCTCAGTACAATCTGCTCTGAT
GCCGCATAGTTAAGCCAGCCCCGACACCCGCCAACACCCGCTGACGAGCT
TAGTAAAGCCCTCGCTAGATTTTAATGCGGATGTTGCGATTACTTCGCCA
ACTATTGCGATAACAAGAAAAAGCCAGCCTTTCATGATATATCTCCCAAT
TTGTGTAGGGCTTATTATGCACGCTTAAAAATAATAAAAGCAGACTTGAC
CTGATAGTTTGGCTGTGAGCAATTATGTGCTTAGTGCATCTAACGCTTGA
GTTAAGCCGCGCCGCGAAGCGGCGTCGGCTTGAACGAATTGTTAGACATT
ATTTGCCGACTACCTTGGTGATCTCGCCTTTCACGTAGTGGACAAATTCT
TCCAACTGATCTGCGCGCGAGGCCAAGCGATCTTCTTCTTGTCCAAGATA
AGCCTGTCTAGCTTCAAGTATGACGGGCTGATACTGGGCCGGCAGGCGCT
CCATTGCCCAGTCGGCAGCGACATCCTTCGGCGCGATTTTGCCGGTTACT
GCGCTGTACCAAATGCGGGACAACGTAAGCACTACATTTCGCTCATCGCC
AGCCCAGTCGGGCGGCGAGTTCCATAGCGTTAAGGTTTCATTTAGCGCCT
CAAATAGATCCTGTTCAGGAACCGGATCAAAGAGTTCCTCCGCCGCTGGA
CCTACCAAGGCAACGCTATGTTCTCTTGCTTTTGTCAGCAAGATAGCCAG
ATCAATGTCGATCGTGGCTGGCTCGAAGATACCTGCAAGAATGTCATTGC
GCTGCCATTCTCCAAATTGCAGTTCGCGCTTAGCTGGATAACGCCACGGA
ATGATGTCGTCGTGCACAACAATGGTGACTTCTACAGCGCGGAGAATCTC
GCTCTCTCCAGGGGAAGCCGAAGTTTCCAAAAGGTCGTTGATCAAAGCTC
GCCGCGTTGTTTCATCAAGCCTTACGGTCACCGTAACCAGCAAATCAATA
TCACTGTGTGGCTTCAGGCCGCCATCCACTGCGGAGCCGTACAAATGTAC
GGCCAGCAACGTCGGTTCGAGATGGCGCTCGATGACGCCAACTACCTCTG
ATAGTTGAGTCGATACTTCGGCGATCACCGCTTCCCTCATGATGTTTAAC
```

```
TTTGTTTTAGGGCGACTGCCCTGCTGCGTAACATCGTTGCTGCTCCATAA
CATCAAACATCGACCCACGGCGTAACGCGCTTGCTGCTTGGATGCCCGAG
GCATAGACTGTACCCCAAAAAAACAGTCATAACAAGCCATGAAAACCGCC
ACTGCGCCGTTACCACCGCTGCGTTCGGTCAAGGTTCTGGACCAGTTGCG
TGAGCGCATACGCTACTTGCATTACAGCTTACGAACCGAACAGGCTTATG
TCCACTGGGTTCGTGCCTTCATCCGTTTCCACGGTGTGCGTCACCCGGCA
ACCTTGGGCAGCAGCGAAGTCGAGGCATTTCTGTCCTGGCTGGCGAACGA
GCGCAAGGTTTCGGTCTCCACGCATCGTCAGGCATTGGCGGCCTTGCTGT
TCTTCTACGGCAAGGTGCTGTGCACGGATCTGCCCTGGCTTCAGGAGATC
GGAAGACCTCGGCCGTCGCGGCGCTTGCCGGTGGTGCTGACCCCGGATGA
AGTGGTTCGCATCCTCGGTTTTCTGGAAGGCGAGCATCGTTTGTTCGCCC
AGCTTCTGTATGGAACGGGCATGCGGATCAGTGAGGGTTTGCAACTGCGG
GTCAAGGATCTGGATTTCGATCACGGCACGATCATCGTGCGGGAGGGCAA
GGGCTCCAAGGATCGGGCCTTGATGTTACCCGAGAGCTTGGCACCCAGCC
TGCGCGAGCAGGGGAATTAATTCCCACGGGTTTTGCTGCCCGCAAACGGG
CTGTTCTGGTGTTGCTAGTTTGTTATCAGAATCGCAGATCCGGCTTCAGC
CGGTTTGCCGGCTGAAAGCGCTATTTCTTCCAGAATTGCCATGATTTTT
CCCCACGGGAGGCGTCACTGGCTCCCGTGTTGTCGGCAGCTTTGATTCGA
TAAGCAGCATCGCCTGTTTCAGGCTGTCTATGTGTGACTGTTGAGCTGTA
ACAAGTTGTCTCAGGTGTTCAATTTCATGTTCTAGTTGCTTTGTTTTACT
GGTTTCACCTGTTCTATTAGGTGTTACATGCTGTTCATCTGTTACATTGT
CGATCTGTTCATGGTGAACAGCTTTGAATGCACCAAAAACTCGTAAAAGC
TCTGATGTATCTATCTTTTTTACACCGTTTTCATCTGTGCATATGGACAG
TTTTCCCTTTGATATGTAACGGTGAACAGTTGTTCTACTTTTGTTTGTTA
GTCTTGATGCTTCACTGATAGATACAAGAGCCATAAGAACCTCAGATCCT
TCCGTATTTAGCCAGTATGTTCTCTAGTGTGGTTCGTTGTTTTTGCGTGA
GCCATGAGAACGAACCATTGAGATCATACTTACTTTGCATGTCACTCAAA
AATTTTGCCTCAAAACTGGTGAGCTGAATTTTTGCAGTTAAAGCATCGTG
TAGTGTTTTTCTTAGTCCGTTATGTAGGTAGGAATCTGATGTAATGGTTG
TTGGTATTTTGTCACCATTCATTTTTATCTGGTTGTTCTCAAGTTCGGTT
ACGAGATCCATTTGTCTATCTAGTTCAACTTGGAAAATCAACGTATCAGT
CGGGCGGCCTCGCTTATCAACCACCAATTTCATATTGCTGTAAGTGTTTA
AATCTTTACTTATTGGTTTCAAAACCCATTGGTTAAGCCTTTTAAACTCA
TGGTAGTTATTTTCAAGCATTAACATGAACTTAAATTCATCAAGGCTAAT
CTCTATATTTGCCTTGTGAGTTTTCTTTTGTGTTAGTTCTTTTAATAACC
ACTCATAAATCCTCATAGAGTATTTGTTTTCAAAAGACTTAACATGTTCC
AGATTATATTTTATGAATTTTTTTAACTGGAAAAGATAAGGCAATATCTC
TTCACTAAAACTAATTCTAATTTTTCGCTTGAGAACTTGGCATAGTTTG
TCCACTGGAAAATCTCAAAGCCTTTAACCAAAGGATTCCTGATTTCCACA
GTTCTCGTCATCAGCTCTCTGGTTGCTTTAGCTAATACACCATAAGCATT
TTCCCTACTGATGTTCATCATCTGAGCGTATTGGTTATAAGTGAACGATA
```

-continued

```
CCGTCCGTTCTTTCCTTGTAGGGTTTTCAATCGTGGGGTTGAGTAGTGCC

ACACAGCATAAAATTAGCTTGGTTTCATGCTCCGTTAAGTCATAGCGACT

AATCGCTAGTTCATTTGCTTTGAAAACAACTAATTCAGACATACATCTCA

ATTGGTCTAGGTGATTTTAATCACTATACCAATTGAGATGGGCTAGTCAA

TGATAATTACTAGTCCTTTTCCTTTGAGTTGTGGGTATCTGTAAATTCTG

CTAGACCTTTGCTGGAAAACTTGTAAATTCTGCTAGACCCTCTGTAAATT

CCGCTAGACCTTTGTGTGTTTTTTTTGTTTATATTCAAGTGGTTATAATT

TATAGAATAAAGAAAGAATAAAAAAAGATAAAAAGAATAGATCCCAGCCC

TGTGTATAACTCACTACTTTAGTCAGTTCCGCAGTATTACAAAAGGATGT

CGCAAACGCTGTTTGCTCCTCTACAAAACAGACCTTAAAACCCTAAAGGC

TTAAG
```

Methods, reagents and tools for transforming host cells described herein, such as bacteria, yeast (including oleaginous yeast) and filamentous fungi are known in the art. General methods, reagents and tools for transforming, e.g., bacteria can be found, for example, in Sambrook et al (2001) *Molecular Cloning: A Laboratory Manual*, 3$^{rd}$ ed., Cold Spring Harbor Laboratory Press, New York. In some embodiments, introduction of the DNA construct or vector of the present invention into a host cell is accomplished by calcium phosphate transfection, DEAE-dextran mediated transfection, electroporation, or other common techniques (See Davis et al., 1986, *Basic Methods in Molecular Biology*, which is incorporated herein by reference). In one embodiment, a preferred method used to transform *E. coli* strains is electroporation and reference is made to Dower et al., (1988) NAR 16: 6127-6145. Indeed, any suitable method for transforming host cells finds use in the present invention. It is not intended that the present invention be limited to any particular method for introducing nucleic acids such as constructs into host cells.

In certain embodiments, the present invention provides a recombinant bacterial microorganism transformed with a gene encoding a heterologous TE comprising at least 70%, (at least 75%, at least 80%, at least 85%, at least 90%, at least 93%, at least 95%, at least 97%, at least 99%, and even 100%) sequence identity to the polypeptide sequence of SEQ ID NO: 10 or SEQ ID NO: 35, a gene encoding a heterologous ACS comprising at least 70%, (at least 75%, at least 80%, at least 85%, at least 90%, at least 93%, at least 95%, at least 97%, at least 99%, and even 100%) sequence identity to the polypeptide sequence of SEQ ID NO: 8 and a gene encoding a heterologous FAR comprising at least 85% (at least 88%, at least 90%, at least 91%, at least 92%, at least 93%, at least 94%, at least 95%, at least 96%, at least 97%, at least 98%, at least 99% and even 100%) sequence identity to the polypeptide of SEQ ID NO: 2, SEQ ID NO: 4, SEQ ID NO: 6, SEQ ID NO: 37 or SEQ ID NO: 39. In some specific embodiments the recombinant bacterial microorganism produces a fatty alcohol composition comprising fatty alcohols having carbon chain lengths of at least 80% C12, C14 and C16 fatty alcohols when said recombinant microorganism is cultured under suitable culture conditions for production of the fatty alcohols.

5. Methods for Gene Inactivation

In some embodiments, endogenous genes of the engineered microorganism of the present invention have been inactivated for example they have been genetically modified to at least partially delete a gene encoding the endogenous enzyme (e.g., FadE or FadR). Typically, these modifications of the gene reduce or eliminate the total amount of endogenous enzyme produced by the host cell. In some embodiments, complete or near-complete deletion of the gene sequence is contemplated. However, a deletion mutation need not completely remove the entire gene sequence encoding the enzyme, in order to reduce the amount of endogenous enzyme produced by the engineered cell. For example, in some embodiments, there is a partial deletion that removes one or more nucleotides encoding a portion of an enzyme (e.g., FadE) that plays a role in endogenous enzyme activity by the host cell (See, U.S. Pat. No. 8,110, 670).

A deletion in a gene encoding an enzyme (e.g., FadE and/or FadR) in accordance with the embodiments provided herein includes a deletion of one or more nucleotides in the gene encoding the target enzyme (e.g., FadE and/or FadR). In some embodiments, there is a deletion of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100%, of the gene (e.g. a gene encoding for example FadE and/or FadR), wherein the amount of enzyme produced by the cell is reduced.

Thus, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the enzyme activity produced by the cell, relative to the enzyme activity of a corresponding enzyme produced by an unmodified organism grown or cultured under essentially the same culture conditions and including the gene coding for the corresponding enzyme which had not be inactivated or deleted. In some embodiments, deletion is of a fadE gene or fadR gene.

Deletion of a gene of interest can be detected and confirmed by any of a variety of methods known in the art for detection of gene deletions, including the methods provided herein. For example, gene deletion can be confirmed using PCR amplification of the modified genomic region. It will be appreciated that additional suitable techniques for confirming deletion can be used and are well known, including but not limited to Southern blot techniques, DNA sequencing of the modified genomic region, and screening for positive or negative markers incorporated during recombination events.

Some additional methods for complete and/or partial deletion of a gene are well-known. The genetically modified cells described herein can be generated using any of a variety of deletion methods known in the art that result in the complete inactivation or at least a reduction in the amount of at least one endogenous gene expressed by the cells.

There are numerous approaches to create genetic modifications in bacteria (See e.g., Court et al., (2002) Annual Rev. Genet 36:361-388; and Datsenko and Wanner (2000) PNAS 97:6640-6645).

In certain embodiments the inactivation is of a fadR polynucleotide sequence encoding a FadR enzyme. For example, in one embodiment, the polynucleotide sequence encoding a FadR enzyme is set forth herein as SEQ ID NO:11, and the encoded amino acid sequence is set forth as SEQ ID NO:12.

SEQ ID NO: 11
ATGGTCATTAAGGCGCAAAGCCCGGCGGGTTTCGCGGAAGAGTACATTAT

TGAAAGTATCTGGAATAACCGCTTCCCTCCCGGGACTATTTTGCCCGCAG

AACGTGAACTTTCAGAATTAATTGGCGTAAGCGTACTACGTTACGTGAAG

TGTTACAGCGTCTGGCACGAGATGGCTGGTTGACCATTCAACATGGCAAG

CCGACGAAGGTGAATAATTTCTGGGAAACTTCCGGTTTAAATATCCTTGA

AACACTGGCGCGACTGGATCACGAAAGTGTGCCGCAGCTTATTGATAATT

TGCTGTCGGTGCGTACCAATATTTCCACTATTTTTATTCGCACCGCGTTT

CGTCAGCATCCCGATAAAGCGCAGGAAGTGCTGGCTACCGCTAATGAAGT

GGCCGATCACGCCGATGCCTTTGCCGAGCTGGATTACAACATATTCCGCG

GCCTGGCGTTTGCTTCCGGCAACCCGATTTACGGTCTGATTCTTAACGGG

ATGAAAGGGCTGTATACGCGTATTGGTCGTCACTATTTCGCCAATCCGGA

AGCGCGCAGTCTGGCGCTGGGCTTCTACCACAAACTGTCGGCGTTGTGCA

GTGAAGGCGCGCACGATCAGTGTACGAAACAGTGCGTCGCTATGGGCATG

AGAGTGGCGAGATTTGGCACCGGATGCAGAAAAATCTGCCGGGTGATTTA

GCCATTCAGGGGCGATAA

SEQ ID NO: 12
MVIKAQSPAGFAEEYIIESIWNNRFPPGTILPAERELSELIGVTRTTLRE

VLQRLARDGWLTIQHGKPTKNNFWETSGLNILETLARLDHESVPQLIDNL

LSVRTNISTIFIRTAFRQHPDKAQEVLATANEVADHADAFAELDYNIFRG

LAFASGNPIYGLILNGMKGLYTRIGRHYFANPEARSLALGFYHKLSALCS

EGAHDQVYETVRRYGHESGEIVVHRMQKNLPGDLAIQGR.

In some embodiments, the FadR is encoded by a nucleic acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:11. In some embodiments, the FadR is encoded by a nucleic acid sequence that can selectively hybridize to SEQ ID NO:11 under moderately stringent or highly stringent conditions, as described hereinabove. In some embodiments, the FadR enzyme has an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:12.

In certain embodiments the inactivation is of a fadE polynucleotide sequence encoding a FadE enzyme. For example, in one embodiment, the polynucleotide sequence encoding a FadE enzyme is set forth herein as SEQ ID NO:13, and the encoded amino acid sequence is set forth as SEQ ID NO:14.

SEQ ID NO: 13
ATGATGATTTTGAGTATTCTCGCTACGGTTGTCCTGCTCGGCGCGTTGTT

CTATCACCGCGTGAGCTTATTTATCAGCAGTCTGATTTTGCTCGCCTGGA

CAGCCGCCCTCGGCGTTGCTGGTCTGTGGTCGGCGTGGGTACTGGTGCCT

CTGGCCATTATCCTCGTGCCATTTAACTTTGCGCCTATGCGTAAGTCGAT

GATTTCCGCGCCGGTATTTCGCGGTTTCCGTAAGGTGATGCCGCCGATGT

CGCGCACTGAGAAAGAAGCGATTGATGCGGGCACCACCTGGTGGGAGGGC

GACTTGTTCCAGGGCAAGCCGGACTGGAAAAAGCTGCATAACTATCCGCA

GCCGCGCCTGACCGCCGAAGAGCAAGCGTTTCTCGACGGCCCGGTAGAAG

AAGCCTGCCGGATGGCGAATGATTTCCAGATCACCCATGAGCTGGCGGAT

CTGCCGCCGGAGTTGTGGGCGTACCTTAAAGAGCATCGTTTCTTCGCGAT

GATCATCAAAAAAGAGTACGGCGGGCTGGAGTTCTCGGCTTATGCCCAGT

CTCGCGTGCTGCAAAAACTCTCCGGCGTGAGCGGGATCCTGGCGATTACC

GTCGGCGTGCCAAACTCATTAGGCCCGGGCGAACTGTTGCAACATTACGG

CACTGACGAGCAGAAAGATCACTATCTGCCGCGTCTGGCGCGTGGTCAGG

AGATCCCCTGCTTTGCACTGACCAGCCCGGAAGCGGGTTCCGATGCGGGC

GCGATTCCGGACACCGGGATTGTCTGCATGGGCGAATGGCAGGGCCAGCA

GGTGCTGGGGATGCGTCTGACCTGGAACAAACGCTACATTACGCTGGCAC

CGATTGCGACCGTGCTTGGGCTGGCGTTTAAACTCTCCGACCCGGAAAAA

TTACTCGGCGGTGCAGAAGATTTAGGCATTACCTGTGCGCTGATCCCAAC

CACCACGCCGGGCGTGGAAATTGGTCGTCGCCACTTCCCGCTGAACGTAC

CGTTCCAGAACGGACCGACGCGCGGTAAAGATGTCTTCGTGCCGATCGAT

TACATCATCGGCGGGCCGAAAATGGCCGGGCAAGGCTGGCGGATGCTGGT

GGAGTGCCTCTCGGTAGGCCGCGGCATCACCCTGCCTTCCAACTCAACCG

GCGGCGTGAAATCGGTAGCGCTGGCAACCGGCGCGTATGCTCACATTCGC

CGTCAGTTCAAAATCTCTATTGGTAAGATGGAAGGGATTGAAGAGCCGCT

GGCGCGTATTGCCGGTAATGCCTACGTGATGGATGCTGCGGCATCGCTGA

TTACCTACGGCATTATGCTCGGCGAAAAACCTGCCGTGCTGTCGGCTATC

GTTAAGTATCACTGTACCCACCGCGGGCAGCAGTCGATTATTGATGCGAT

GGATATTACCGGCGGTAAAGGCATTATGCTCGGGCAAAGCAACTTCCTGG

CGCGTGCTTACCAGGGCGCACCGATTGCCATCACCGTTGAAGGGGCTAAC

ATTCTGACCCGCAGCATGATGATCTTCGGACAAGGAGCGATTCGTTGCCA

TCCGTACGTGCTGGAAGAGATGGAAGCGGCGAAGAACAATGACGTCAACG

CGTTCGATAAACTGTTGTTCAAACATATCGGTCACGTCGGTAGCAACAAA

GTTCGCAGCTTCTGGCTGGGCCTGACGCGCGGTTTAACCAGCAGCACGCC

AACCGGCGATGCCACTAAACGCTACTATCAGCACCTGAACCGCCTGAGCG

CCAACCTCGCCCTGCTTTCTGATGTCTCGATGGCAGTGCTGGGCGGCAGC

CTGAAACGTCGCGAGCGCATCTCGGCCCGTCTGGGGGATATTTTAAGCCA

GCTCTACCTCGCCTCTGCCGTGCTGAAGCGTTATGACGACGAAGGCCGTA

ATGAAGCCGACCTGCCGCTGGTGCACTGGGGCGTACAAGATGCGCTGTAT

CAGGCTGAACAGGCGATGGATGATTTACTGCAAAACTTCCCGAACCGCGT

GGTTGCCGGGCTGCTGAATGTGGTGATCTTCCCGACCGGACGTCATTATC

TGGCACCTTCTGACAAGCTGGATCATAAAGTGGCGAAGATTTTACAAGTG

```
-continued
CCGAACGCCACCCGTTCCCGCATTGGTCGCGGTCAGTACCTGACGCCGAG

CGAGCATAATCCGGTTGGCTTGCTGGAAGAGGCGCTGGTGGATGTGATTG

CCGCCGACCCAATTCATCAGCGGATCTGTAAAGAGCTGGGTAAAAACCTG

CCGTTTACCCGTCTGGATGAACTGGCGCACAACGCGCTGGTGAAGGGGCT

GATTGATAAAGATGAAGCCGCTATTCTGGTGAAAGCTGAAGAAAGCCGTC

TGCGCAGTATTAACGTTGATGACTTTGATCCGGAAGAGCTGGCGACGAAG

CCGGTAAAGTTGCCGGAGAAAGTGCGGAAAGTTGAAGCCGCGTAA

SEQ ID NO: 14
MMILSILATVVLLGALFYHRVSLFISSLILLAWTAALGVAGLWSAWVLVP

LAIILVPFNFAPMRKSMISAPVFRGFRKVMPPMSRTEKEAIDAGTTWWEG

DLFQGKPDWKKLHNYPQPRLTAEEQAFLDGPVEEACRMANDFQITHELAD

LPPELWAYLKEHRFFAMIIKKEYGGLEFSAYAQSRVLQKLSGVSGILAIT

VGVPNSLGPGELLQHYGTDEQKDHYLPRLARGQEIPCFALTSPEAGSDAG

AIPDTGIVCMGEWQGQQVLGMRLTWNKRYITLAPIATVLGLAFKLSDPEK

LLGGAEDLGITCALIPTTTPGVEIGRRHFPLNVPFQNGPTRGKDVFVPID

YIIGGPKMAGQGWRMLVECLSVGRGITLPSNSTGGVKSVALATGAYAHIR

RQFKISIGKMEGIEEPLARIAGNAYVMDAAASLITYGIMLGEKPAVLSAI

VKYHCTHRGQQSIIDAMDITGGKGIMLGQSNFLARAYQGAPIAITVEGAN

ILTRSMMIFGQGAIRCHPYVLEEMEAAKNNDVNAFDKLLFKHIGHVGSNK

VRSFWLGLTRGLTSSTPTGDATKRYYQHLNRLSANLALLSDVSMAVLGGS

LKRRERISARLGDILSQLYLASAVLKRYDDEGRNEADLPLVHWGVQDALY

QAEQAMDDLLQNFPNRVVAGLLNVVIFPTGRHYLAPSDKLDHKVAKILQV

PNATRSRIGRGQYLTPSEHNPVGLLEEALVDVIAADPIHQRICKELGKNL

PFTRLDELAHNALVKGLIDKDEAAILVKAEESRLRSINVDDFDPEELATK

PVKLPEKVRKVEAA
```

In some embodiments, the FadE is encoded by a nucleic acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:13. In some embodiments, the FadE is encoded by a nucleic acid sequence that can selectively hybridize to SEQ ID NO:13 under moderately stringent or highly stringent conditions, as described hereinabove. In some embodiments, the FadE has an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:14. FadE sequences can be identified by any of a variety of methods known in the art. For example, a sequence alignment can be conducted against a database, for example against the NCBI database, and sequences with the lowest HMM E-value can be selected.

In certain embodiments, an engineered cell of the invention (e.g., E. coli) comprises a gene encoding a heterologous TE comprising at least 70%, (at least 75%, 80%, 85%, 90%, 93%, 95%, 97%, 99%, and even 100%) sequence identity to the polypeptide sequence of SEQ ID NO: 10 or SEQ ID NO: 35 or a functional fragment thereof, a gene encoding a heterologous ACS comprising at least 70%, (at least 75%, 80%, 85%, 90%, 93%, 95%, 97%, 99%, and even 100%) sequence identity to the polypeptide sequence of SEQ ID NO: 8 or a functional fragment thereof; a gene encoding a heterologous FAR comprising at least 85% (at least 88%, 90%, 91%, 92%, 93%, 94%, 95%, 96%, 97%, 98% 99% and even 100%) to the polypeptide of SEQ ID NO: 2, SEQ ID NO: 4, SEQ ID NO: 6, SEQ ID NO: 37 or SEQ ID NO: 39 or a functional fragment thereof and optionally an inactivated gene encoding a FadE enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14 and/or an inactivated gene encoding a FadR enzyme comprising about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:12.

In certain embodiments, an engineered cell of the invention (e.g., an E. coli) comprises a gene encoding a heterologous TE comprising at least 85%, sequence identity to the polypeptide sequence of SEQ ID NO: 10 or SEQ ID NO: 35 or a functional fragment thereof, a gene encoding a heterologous ACS comprising at least 85% sequence identity to the polypeptide sequence of SEQ ID NO: 8 or a functional fragment thereof; a gene encoding a heterologous FAR comprising at least 90%, sequence identify to the polypeptide of SEQ ID NO: 2, SEQ ID NO: 4, SEQ ID NO: 6, SEQ ID NO: 37 or SEQ ID NO: 39 or a functional fragment thereof and optionally an inactivated gene encoding a FadE enzyme having at least about 85%, sequence identity to SEQ ID NO:14 and/or an inactivated gene encoding a FadR enzyme comprising about 85% sequence identity to SEQ ID NO:12.

In certain embodiments, an engineered cell of the invention (e.g., E. coli) comprises a gene encoding a heterologous TE comprising at least 95% sequence identity to the polypeptide sequence of SEQ ID NO: 10, SEQ ID NO: 35 or a functional fragment thereof, a gene encoding a heterologous ACS comprising at least 95% sequence identity to the polypeptide sequence of SEQ ID NO: 8 or a functional fragment thereof; a gene encoding a heterologous FAR comprising at least 90%, sequence identity to the polypeptide of SEQ ID NO: 2, SEQ ID NO: 4, SEQ ID NO: 6, SEQ ID NO: 37 or SEQ ID NO: 39 or a functional fragment thereof and optionally an inactivated gene encoding a FadE enzyme having at least about 90%, sequence identity to SEQ ID NO:14 and/or an inactivated gene encoding a FadR enzyme comprising about 90% sequence identity to SEQ ID NO:12.

In certain embodiments, an engineered cell of the invention (e.g., E. coli) comprises a gene encoding a heterologous TE comprising at least 95% sequence identity to the polypeptide sequence of SEQ ID NO: 10, SEQ ID NO: 35 or a functional fragment thereof, a gene encoding a heterologous ACS comprising at least 95% sequence identity to the polypeptide sequence of SEQ ID NO: 8 or a functional fragment thereof; a gene encoding a heterologous FAR comprising at least 95%, sequence identity to the polypeptide of SEQ ID NO: 37 or SEQ ID NO: 39 or a functional fragment thereof and optionally an inactivated gene encoding a FadE enzyme having at least about 90%, sequence identity to SEQ ID NO:14 and/or an inactivated gene encoding a FadR enzyme comprising about 90% sequence identity to SEQ ID NO:12.

6. Host Cells

In some embodiments, the recombinant bacterial microorganism according to the invention is a Gram-positive, Gram negative or Gram-variable bacterial cell. In certain embodiments, host cells include, but are not limited to, species of a genus selected from the group consisting of *Agrobacterium, Arthrobacter, Bacillus, Clostridium, Corynebacterium, Escherichia, Erwinia, Geobacillus, Klebsiella, Lactobacillus, Mycobacterium, Pantoea, Rhodococcus, Rhotobacter, Streptomyces* and *Zymomonas*. In certain embodiments, the recombinant host cell is an industrial bacterial strain.

Numerous bacterial industrial strains are known and suitable for use in the methods disclosed herein. In some embodiments, the bacterial host cell is a species of the genus *Bacillus*, e.g., *B. thuringiensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans, B. subtilis, B. pumilus,* and *B. amyloliquefaciens*. In some embodiments, the bacterial host cell is a species of the genus *Erwinia*, e.g., *E. uredovora, E. carotovora, E. ananas, E. herbicola, E. punctata* and *E. terreus*. In other embodiments the bacterial host cell is a species of the genus *Pantoea*, e.g., *P. citrea* or *P. agglomerans*. In still other embodiments, the bacterial host cell is a species of the genus *Streptomyces*, e.g., *S. ambofaciens, S. achromogenes, S. avennitilis, S. coelicolor, S. aureofaciens, S. aureus, S. fungicidicus, S. griseus* or *S. lividans*. In further embodiments, the bacterial host cell is a species of the genus *Zymomonas*, e.g., *Z. mobilis* or *Z. lipolytica*. In further embodiments, the bacterial host cell is a species of the genus *Rhodococcus*, e.g. *R. opacus*.

In some embodiments, the bacterial host cell is a species of the genus *Escherichia*, e.g., *E. coli*. In various embodiments, the engineered *E. coli* bacterial strains useful in the processes described herein are derived from strain W3110, strain MG1655, strain B766 (*E. coli* W) and strain BW25113. In some further embodiments, the W3110 strain finds use in the present invention; the genome of this strain has been fully sequenced and annotated See e.g., Hayashi et al., (2005) Mol. Syst. Biol. 2:2006.0007). For industrial applications, phage-resistant strains are particularly useful. In this sense, deletion of the fhuA gene (also known as tonA) confers resistance to phages T1, T5 and phi80 (Link et al., 1997, J. Bact. 179: 6228-8237). Another useful strain is *E. coli* W (Archer et al., 2011, BMC Genomics, 12:9.doi: 10.1186/1471-2164-12-9). Also reference is made to Elben et al. (2005) J. of Food Protection 68(2):282-291.

Other examples of useful *E. coli* strains include, but are not limited to, *E. coli* strains found in the *E. coli* Stock Center from Yale University (http://cgsc.biology.yale.edu/index.php); the Keio Collection, available from the National BioResource Project at NBRP *E. coli*, Microbial Genetics Laboratory, National Institute of Genetics 1111 Yata, Mishima, Shizuoka, 411-8540 Japan (www at shigen.ni-g.ac.jp/ecoli/strain/top/top.jsp); or strains deposited at the American Type Culture Collection (ATCC).

In some embodiments the host cell is an *E. coli* cell that has been transformed with a polynucleotide sequence encoding a TE, an ACS and a FAR as described herein. The polynucleotides encoding each of these enzymes may be located on the same vector or they may be located on different vectors. In some embodiments, the recombinant *E. coli* comprises a encoding a heterologous TE comprising at least 70%, (at least 75%, 80%, 85%, 90%, 93%, 95%, 97%, 99%, and even 100%) sequence identity to the polypeptide sequence of SEQ ID NO: 10, SEQ ID NO: 35 or a functional fragment thereof, a gene encoding a heterologous ACS comprising at least 70%, (at least 75%, 80%, 85%, 90%, 93%, 95%, 97%, 99%, and even 100%) sequence identity to the polypeptide sequence of SEQ ID NO: 8 or a functional fragment thereof; a gene encoding a heterologous FAR comprising at least 85% (at least 88%, 90%, 91%, 92%, 93%, 94%, 95%, 96%, 97%, 98% 99% and even 100%) to the polypeptide of SEQ ID NO: 2, SEQ ID NO: 4, SEQ ID NO: 6, SEQ ID NO: 37 or SEQ ID NO: 39 or a functional fragment thereof and optionally an inactivated gene encoding a FadE enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14 and/or an inactivated gene encoding a FadR enzyme comprising about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:12.

In some embodiments the host cell is an *E. coli* cell that has been transformed with a polynucleotide sequence encoding a heterologous TE comprising at least 85% sequence identity to the polypeptide sequence of SEQ ID NO: 10, SEQ ID NO: 35 or a functional fragment thereof, a gene encoding a heterologous ACS comprising at least 85% sequence identity to the polypeptide sequence of SEQ ID NO: 8 or a functional fragment thereof; a gene encoding a heterologous FAR comprising at least 90%, sequence identify to the polypeptide of SEQ ID NO: 2, SEQ ID NO: 4, SEQ ID NO: 6, SEQ ID NO: 37 or SEQ ID NO: 39 or a functional fragment thereof and optionally an inactivated gene encoding a FadE enzyme having at least about 85%, sequence identity to SEQ ID NO:14 and/or an inactivated gene encoding a FadR enzyme comprising about 85%, sequence identity to SEQ ID NO:12.

In some embodiments the host cell is an *E. coli* cell that has been transformed with a polynucleotide sequence encoding a heterologous TE comprising at least 90%, sequence identity to the polypeptide sequence of SEQ ID NO: 10 or a variant or functional fragment thereof, a gene encoding a heterologous ACS comprising at least 85% sequence identity to the polypeptide sequence of SEQ ID NO: 8 or a variant or functional fragment thereof; a gene encoding a heterologous FAR comprising at least 90%, sequence identify to the polypeptide of SEQ ID NO: 2, SEQ ID NO: 4, SEQ ID NO: 6, SEQ ID NO: 37 or SEQ ID NO: 39 or a functional fragment thereof and optionally an inactivated gene encoding a FadE enzyme having at least about 90%, sequence identity to SEQ ID NO:14 and/or an inactivated gene encoding a FadR enzyme comprising about 90%, sequence identity to SEQ ID NO:12.

In some of the embodiments described above, the recombinant bacteria cells (for example E. coli) encompassed by the invention are cultured under suitable conditions for the production of a fatty alcohols. In some cases the fatty alcohol composition will comprise at least 60% (at least 65%, 70%, 75%, and 80%) of any one of C12, C14, C16 fatty alcohols or combinations thereof.

7. Fermentation/Culturing

Any suitable means for culturing the recombinant host cells finds use in the present invention. Indeed, any suitable fermentation protocol finds use in the production of the fatty alcohols provided herein. In some embodiments, fermentation of the recombinant host cells as described hereinabove for example comprises fermenting bacterial host cells such as E. coli comprising: a heterologous polynucleotide encoding a TE enzyme, a heterologous polynucleotide encoding an ACS enzyme and a heterologous polynucleotide encoding a FAR and optionally further comprising an inactivated fadE and/or an inactivated fadR gene, under suitable conditions and for a time sufficient for production of fatty alcohols, as desired. In some embodiments, the recombinant bacterial cell will also include the overexpression of one or more fatty acid biosynthetic genes, such as fabA, fabB, and/or fabZ.

Conditions for the culture and production of cells, including bacterial, fungal and yeast cells, are readily available and well-known in the art. The engineered host cells can be cultured in conventional nutrient media modified as appropriate. Culture conditions, such as temperature, pH and the like, are those previously used with the host cell selected for expression, and will be apparent to those skilled in the art.

Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue and supplement* (1997) also from Sigma-Aldrich, Inc (St Louis, Mo.) ("Sigma-PCCS"), all of which are incorporated herein by reference. Reference is also made to the Manual of Industrial Microbiology and Biotechnology. A. Demain and J. Davies Eds. ASM Press. 1999.

In some embodiments, the recombinant cells encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out a temperature within the range of from about 10° C. to about 60° C., from about 15° C. to about 50° C., from about 20° C. to about 45° C., from about 25° C. to about 45° C., from about 30° C. to about 45° C. or from about 25° C. to about 40° C. Indeed, it is intended that any suitable fermentation temperature will be used in the present invention.

In some other embodiments, the fermentation is carried out for a period of time within the range of from about 8 hours to 240 hours, from about 8 hours to about 168 hours, from about 16 hours to about 144 hours, from about 16 hours to about 120 hours, or from about 24 hours to about 72 hours. Indeed, it is intended that any suitable fermentation time will find use in the present invention.

In some other embodiments, the fermentation will be carried out at a pH in the range of about 4 to about 8, in the range of about 4.5 to about 7.5, in the range of about 5 to about 7, or in the range of about 5.5 to about 6.5. Indeed, it is intended that any suitable pH range will find use in the present invention.

In some specific embodiments, the invention is directed to a recombinant bacterial microbial culture comprising a composition of fatty alcohols wherein said fatty alcohol composition comprises fatty alcohols having a carbon chain length of at least 60%, (at least 65%, 70%, 75%, 80%) of C12, C14 and C16 fatty alcohols, the culture comprising a recombinant bacterial microorganism comprising (a) a gene encoding a heterologous thioesterase ("TE"); (b) a gene encoding a heterologous fatty alcohol forming acyl-CoA reductase ("FAR") and (c) an over-expressed acyl-CoA synthetase ("ACS").

Carbon sources useful in the fermentation medium (e.g., broth) in which the recombinant microorganisms are grown are those that can be assimilated by the recombinant host strain. Such carbon sources are available in many forms and include renewable carbon sources, including but not limited to cellulosic and starch feedstock substrates obtained therefrom. Such examples include for example fermentable sugars such as monosaccharides, disaccharides, and short chain oligosaccharides (e.g., glucose, fructose, xylose, galactose, arabinose, maltose, mannose, and sucrose, fructo-oligosaccharide, galacto-oligosaccharide as well as numerous other sugars; it is not intended that the present invention be limited to any particular fermentable sugar). Other carbon sources include, but are not limited to saturated and unsaturated fatty acids, alcohols, glycerol, lactose, succinate, ketones, amino acids, acetate, gases (e.g., $CO_2$), and mixtures thereof.

In some embodiments, the assimilable carbon source is from cellulosic and/or starch feedstock derived from but not limited to, wood, wood pulp, paper pulp, grain (e.g., corn grain), corn stover, corn fiber, rice, paper and pulp processing waste, woody or herbaceous plants and residue, fruit or vegetable pulp, distillers grain, grasses, rice hulls, wheat straw, cotton, hemp, flax, sisal, corn cobs, sugar cane bagasse, sugar beets, sorghum, barely, barely straw, switch grass, wood chips, municipal solid wastes, aquatic crops, and mixtures thereof.

In some embodiments, the cellulosic feedstock useful as an assimilable carbon source has been derived from a biomass substrate that has been pretreated. The term "biomass" is broadly used herein to encompasses any living or dead biological material that contains a polysaccharide substrate, including but not limited to cellulose, starch, other forms of long-chain carbohydrate polymers, and mixtures of such sources. Examples of biomass include, but are not limited to, wood, wood pulp, paper pulp, corn fiber, corn grain, corn cobs, sugar cane, sugar beet, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp (e.g., sugar beet)), or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass may also comprise transgenic plants that express ligninase and/or cellulase enzymes (See e.g., US 2008/0104724 A1).

In some specific embodiments the invention is directed to a method of producing a fatty alcohol composition comprising culturing a recombinant bacterial microorganism comprising (a) a gene encoding a heterologous thioesterase ("TE"); (b) a gene encoding a heterologous fatty alcohol forming acyl-CoA reductase ("FAR") and (c) an over-expressed acyl-CoA synthetase ("ACS") in the presence of fermentable sugars obtained from a cellulosic feedstock under suitable culture conditions to produce a fatty alcohol composition wherein the microorganism is cultured at a temperature in the range of 20° C. to 45° C.; a pH in the range of pH 5 to pH 7; and for a time in the range of from 16 hours to 144 hours.

In some embodiments, cellulosic biomass substrate is "pretreated," using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. In some embodiments, the substrate is slurried prior to pretreatment. The following references described various means of pretreatment. Steam explosion performing acid pretreatment of biomass substrates is described in U.S. Pat. No. 4,461,648. Continuous pretreatment using a slurry is described U.S. Pat. No. 7,754,457. Methods of alkali pretreatment is such as Ammonia Freeze Explosion, Ammonia Fiber Explosion or Ammonia Fiber Expansion ("AFEX") are described in U.S. Pat. Nos. 5,171,592; 5,037,663; 4,600,590; 6,106,888; 4,356,196; 5,939,544; 6,176,176; 5,037,663 and 5,171,592. Alternative methods to AFEX utilizing a dilute ammonia pretreatments are described in WO2009/045651 and US 2007/0031953. Chemical pretreatments with organic solvents are disclosed in U.S. Pat. No. 4,556,430. Other pretreatments methods are disclosed in U.S. Pat. No. 7,465,791, and Weil et al. (1997) Appl. Biochem. Biotechnol., 68(1-2): 21-40 [1997].

8. Production of Fatty Alcohols

In certain embodiments of the invention, at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the fatty alcohols produced by the methods described herein are secreted into the culture medium by the recombinant host cells.

In various embodiments, the fatty alcohol compositions produced by the methods described herein comprise both saturated and unsaturated fatty alcohols. In certain embodiments, the unsaturated fatty alcohols are monounsaturated fatty alcohols. In some embodiments, the fatty alcohol compositions comprise both saturated and unsaturated fatty alcohols, and the amount of unsaturated fatty alcohols compared to saturated fatty alcohols in the total fatty alcohol composition is less than about 40%, less than about 35%, less than about 30%, less than about 20%, less than about 15%, less than about 10%, less than about 5%, or less than about 1% of the fatty alcohols present in the composition.

In some embodiments, the percentage of saturated fatty alcohols in the fatty alcohol compositions produced by the engineered bacterial cells encompassed by the invention is greater than about 50%, greater than about 55%, greater than about 60%, greater than about 65%, greater than about 70%, greater than about 75%, greater than about 80%, greater than about 85%, greater than about 90%, greater than about 95%, or greater than about 97%.

In some embodiments, the fatty alcohol compositions produced by the methods described herein comprise one or more fatty alcohols selected from 1-decanol (C10:0), 1-dodecanol (C12:0), 1-tetradecanol (C14:0), 1-hexadecanol (C16:0), and 1-octadecanol (C18:0).

In some typical embodiments, C10 to C18 fatty alcohols comprise at least about 90%, at least about 95%, at least about 96%, at least about 97%, at least about 98%, or at least about 99% by weight of the total fatty alcohols produced by the recombinant host cells of the invention. In some embodiments, C12 to C16 fatty alcohols comprise at least about 85%, at least about 90%, at least about 92%, at least about 93%, at least about 94%, at least about 95%, at least about 96%, at least about 97%, or at least about 98% by weight of the total fatty alcohols produced by the recombinant host cells of the invention. In certain embodiments, C14 to C16 fatty alcohols comprise at least about 80%, at least about 85%, at least about 90%, at least about 92%, at least about 95%, at least about 97%, or at least about 99% by weight of the total fatty alcohols produced by the recombinant cells of the invention. In some embodiments, C12 to C14 fatty alcohols comprise at least about 85%, at least about 90%, at least about 92%, at least about 93%, at least about 94%, at least about 95%, at least about 96%, at least about 97%, or at least about 98% by weight of the total fatty alcohols produced by the recombinant host cells of the invention. It is understood that a reference to a "Cx fatty alcohol" (e.g., C12) includes both saturated and unsaturated fatty alcohols having "x" carbon atoms.

In some typical embodiments, C10:0 to C18:0 fatty alcohols comprise at least about 95%, at least about 96%, at least about 97%, at least about 98%, or at least about 99% by weight of the total fatty alcohols produced by the recombinant cells of the invention. In some embodiments, C12:0 to C16:0 fatty alcohols comprise at least about 80%, at least about 85%, at least about 90%, at least about 92%, at least about 93%, at least about 94%, at least about 95%, or at least about 98% by weight of the total fatty alcohols produced by the recombinant host cells of the invention. In certain embodiments, C14:0 to C16:0 fatty alcohols comprise at least about 80%, at least about 85%, at least about 90%, at least about 92%, at least about 95%, at least about 97%, or at least about 99% by weight of the total fatty alcohols produced by the recombinant host cells of the invention. In certain embodiments, C12:0 to C14:0 fatty alcohols comprise at least about 80%, at least about 85%, at least about 90%, at least about 92%, at least about 95%, at least about 97%, or at least about 99% by weight of the total fatty alcohols produced by the recombinant host cells of the invention. The proportions of saturated and unsaturated fatty alcohols produced by the strains may be calculated after quantifying all the fatty alcohol species using any suitable method known in the art (e.g., GC-FID as described in US 2011/0000125SA1). The saturated fraction represents the sum of all C12:0-OH; C14:0-OH; C16:0-OH and C18:0-OH. While the unsaturated fraction is composed of the sum of C12:1-OH: C14:1-OH: C16:1-OH and C18:1-OH.

In some embodiments, the fatty alcohol compositions produced by the recombinant cells comprise a % of saturated fatty alcohols that is greater than about 55%; greater than about 60%; greater than about 65%; greater than about 70%; greater than about 75%; greater than about 80%; greater than about 85%; greater than about 90%; greater than about 95%; or greater than about 97%. In some additional embodiments, the fatty alcohol compositions further comprise at least about 85%, at least about 88%, at least about 90%, at least about 91%, at least about 92%, at least about 93%, at least about 94%, at least about 95%, at least about 96%, at least about 97%, or at least about 98% C12 to C16 fatty alcohols; wherein at least 50%, at least 60%, at least 65%, at least 70%, at least 75%, at least 80%, at least 90%, at least 95% of the C12 to C16 fatty alcohols are saturated.

In certain embodiments, the fatty alcohol composition produced by the recombinant cells such as *E. coli* cells comprise at least 20% (at least 25%, at least 30%, at least 35%, at least 40%, at least 45%, at least 50% or more) of C12 fatty alcohols in the total fatty alcohol composition. In some embodiments, the fatty alcohol composition produced by the recombinant cells such as *E. coli* cells comprise at least 10%, at least 15%, at least 20%, at least 25%, at least 30%, at least 35%, at least 40%, at least 45%, at least 50% or more of C12 fatty alcohols in the total fatty alcohol composition as compared to a corresponding engineered recombinant cell grown under essentially the same culture conditions.

In certain embodiments, the fatty alcohol composition produced by the recombinant cells such as *E. coli* cells comprise at least 20% (at least 25%, at least 30%, at least 35%, at least 40%, at least 45%, at least 50% or more) of C14 fatty alcohols in the total fatty alcohol composition. In some embodiments, the fatty alcohol composition produced by the recombinant cells such as *E. coli* cells comprise at least 10%, at least 15%, at least 20%, at least 25%, at least 30%, at least 35%, at least 40%, at least 45%, at least 50% or more of C14 fatty alcohols in the total fatty alcohol composition as compared to a corresponding engineered recombinant cell grown under essentially the same culture conditions.

In one non-limiting example the cultured engineered bacterial cells comprising (a) a gene encoding a heterologous thioesterase ("TE") comprising at least 90% (at least 93%, at least 95%, at least 96%, at least 97%, at least 98%, at least 99% and even 100%) sequence identity to SEQ ID NO: 35; (b) a gene encoding a heterologous FAR comprising at least 95% (at least 96%, at least 97%, at least 98%, at least 99% and even 100%) sequence identity to SEQ ID NO: 37 or SEQ ID NO: 39 and (c) an over-expressed acyl-CoA synthetase ("ACS") comprising at least 95% (at least 96%, at least 97%, at least 98%, at least 99% and even 100%) sequence identity to SEQ ID NO: 8; is compared to a corresponding engineered recombinant bacterial microorganism which includes the gene encoding the heterologous FAR comprising at least 95% (at least 96%, at least 97%, at least 98%, at least 99% and even 100%) sequence identity to SEQ ID NO: 37 or SEQ ID NO: 39 but does not comprise the gene encoding the heterologous thioesterase ("TE") comprising at least 90% (at least 93%, at least 95%, at least 96%, at least 97%, at least 98%, at least 99% and even 100%) sequence identity to SEQ ID NO: 35 nor the over-expressed acyl-CoA synthetase ("ACS") comprising at least 95% (at least 96%, at least 97% at least 98%, at least 99% and even 100%) sequence identity to SEQ ID NO: 8, wherein the cultured engineered bacterial cells are *E. coli* and said cells produce a fatty alcohol composition comprising at least 20% of C12 fatty alcohols. In all cases, the cultured engineered bacterial cells and the cultured corresponding cells which are being compared to the engineered bacterial cells of the invention will have the same FAR sequence. By way of example and clarification but not limitation, the cultured engineered bacterial cells of the invention and the corresponding bacterial cells in one subset example will both include the same heterologous FAR sequence which is one that comprises at least 98% sequence identity to SEQ ID NO: 39.

In another non-limiting example cultured engineered bacterial cells comprising (a) a gene encoding a heterologous thioesterase ("TE") comprising at least 95% sequence identity to SEQ ID NO: 35; (b) a gene encoding a heterologous FAR comprising at least 95% sequence identity to SEQ ID NO: 37 or SEQ ID NO: 39 and (c) an over-expressed acyl-CoA synthetase ("ACS") comprising at least 95% sequence identity to SEQ ID NO: 8; is compared to a corresponding engineered recombinant bacterial microorganism which includes the gene encoding the heterologous FAR comprising at least 95% sequence identity to SEQ ID NO: 37 or SEQ ID NO: 39 but does not comprise the gene encoding the heterologous thioesterase ("TE") comprising at least 95% sequence identity to SEQ ID NO: 35 nor the over-expressed acyl-CoA synthetase ("ACS") comprising at least 95% sequence identity to SEQ ID NO: 8 wherein the cultured engineered bacterial cells are *E. coli* and said cells produce a fatty alcohol composition comprising at least 20% of C12 fatty alcohols.

In another non-limiting example cultured engineered *E. coli* cells comprising (a) a gene encoding a heterologous thioesterase ("TE") comprising at least 95% (at least 96%, at least 97%, at least 98%, at least 99% and even 100% sequence identity) to SEQ ID NO: 35; (b) a gene encoding a heterologous FAR comprising at least 97% (at least 98%, at least 99% and even 100%) sequence identity to SEQ ID NO: 39 and (c) an over-expressed acyl-CoA synthetase ("ACS") comprising at least 95% sequence identity to SEQ ID NO: 8; is compared to a corresponding engineered recombinant bacterial microorganism which includes the gene encoding the heterologous FAR comprising at least 97% (at least 98%, at least 99% and even 100%) sequence identity to SEQ ID NO: 39 but does not comprise the gene encoding the heterologous thioesterase ("TE") comprising at least 95% (at least 96%, at least 97%, at least 98%, at least 99% and even 100% sequence identity) sequence identity to SEQ ID NO: 35 nor the over-expressed acyl-CoA synthetase ("ACS") comprising at least 95% sequence identity to SEQ ID NO: 8 wherein the cultured engineered cells of the invention a fatty alcohol composition comprising at least 50% of C12 fatty alcohols.

In some of the embodiments described above, the cultured engineered bacteria cells will produce a fatty alcohol composition comprising at least 60% (at least 65%, 70%, 75%, and 80%) of a combination of C12, C14, and C16 fatty alcohols.

In certain embodiments, the amount of fatty alcohols produced by the recombinant bacterial cells according to the methods described herein comprise saturated and/or unsaturated C8 to C18 alcohols in a range of about 10 mg/L to about 150 g/L of aqueous nutrient medium, such as in a range of about 10 mg/L to about 125 g/L, about 10 mg/L to about 100 g/L, about 10 mg/L to about 75 g/L, about 10 mg/L to about 50 g/L, about 10 mg/L to about 25 g/L, about 10 mg/L to about 5 g/L or in a range of about 10 mg/L to about 2 g/L of medium, using routine modification of culturing conditions. In some embodiments, the amount of fatty alcohols produced by the methods described herein is at least about 0.5 g/L, at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, or at least about 10 g/L of medium. In various embodiments, the amount of fatty alcohols produced by the methods described herein is at least about 20 g/L, at least about 30 g/L, at least about 40 g/L, or at least about 50 g/L of medium. In some embodiments, a recombinant bacteria (e.g., *E. coli*) encompassed by the invention produces C12 to C16 fatty alcohols in an amount of at least about 1.0 g/L, at least about 5.0 g/L, at least about 10 g/L, at least about 15 g/L, at least about 20 g/L, at least about 25 g/L, or at least about 30 g/L of medium. In some embodiments, a recombinant bacteria (e.g., *E. coli*) encompassed by the invention produces C12 to C14 fatty alcohols in an amount of at least about 1.0 g/L, at least about 5.0 g/L, at least about 10 g/L, at least about 15 g/L, at least about 20 g/L, at least about 25 g/L, or at least about 30 g/L of medium. One method to extract and quantify fatty alcohols is provided in US Patent Application 2011/0000125. However, it is not intended that the present invention be limited to any particular method(s) for extracting and/or quantifying the fatty alcohols produced using the present invention, as any suitable methods find use.

In some embodiments, the amount of fatty alcohols produced by the methods described herein are in at least about 100 mg/g, at least 500 mg/g, at least 1 g/g, at least 2 g/g, at least 5 g/g/ at least 6 g/g, at least 7 g/g, at least 8 g/g/ at least 9 g/g/ at least 10 g/g/ at least 12 g/g at least 15 g/g of dry cell weight. In some embodiments the amount of fatty alcohols produced by the methods described herein are in the range of about 100 mg/g to about 15 g/g of dry cell weight and also in the range of about 100 mg/g to about 10 g/g of dry cell weight. In other embodiments, the amount of fatty alcohols produced by the methods described herein is in the range of about 1 g/g to about 12 g/g; about 1 g/g to about 10 g/g; about 1 g/g/ to about 5 g/g of dry cell weight, and about 5 g/g to about 10 g/g of dry cell weight.

In certain embodiments, the amount of fatty alcohols produced by the methods described herein is in the range of about 10% to about 20% of dry cell weight, about 20% to about 30% of dry cell weight, about 30% to about 40% of dry cell weight, about 40% to about 50% of dry cell weight, about 50% to about 60% of dry cell weight, about 60% to about 70% of dry cell weight, or about 70% to about 80% of dry cell weight.

In some embodiments, the fatty alcohol compositions produced by the engineered cells and methods described herein may also comprise fatty acid-derived components. Fatty acid derivative compounds include compounds such as but not limited to esters (e.g. acetyl, methyl or ethyl esters and waxes) and fatty acids.

In various embodiments, fatty alcohol compositions produced by the recombinant bacterial cells encompassed by the invention are further recovered or isolated. Recovery or isolation of the produced fatty alcohols refers to substantially separating the fatty alcohols from other components of the culture medium or fermentation process. Recovery or isolation may be accomplished by solvent extraction of the aqueous nutrient medium with a suitable water immiscible solvent. Extraction may occur simultaneously with fatty alcohol production and in some embodiments, extraction is continuous. Phase separation followed by solvent removal provides the fatty alcohol which may then be further purified and fractionated using methods and equipment known in the art. In some other aspects of the invention, the secreted fatty alcohols coalesce to form a water immiscible phase that can be directly separated from the aqueous nutrient medium either during the fermentation process or after its completion.

In certain embodiments, fatty alcohols are isolated by separating the host cells from the aqueous nutrient medium, for example by centrifugation, resuspension and extraction of the fatty alcohols from the recombinant host cells using an organic solvent or solvent mixture. Suitable protocols for recovering fatty alcohols from recombinant host cells and/or culture medium are known to the skilled artisan. In some embodiments, fatty alcohols may be recovered by first lysing the cells to release the fatty alcohols and then extracting the fatty alcohol from the lysate using conventional means. Reference is also made to Yeast Protocols Handbook, (2009) Clontech Laboratories, Inc. A Takara Bio Company, Mt. View Calif. 94043; PNAS 2003 Vol. 100, 16:9156-9161; and Doan et al., (2009) J. Plant Physiol. 166: 787-796 which discloses methods to isolate and measure fatty alcohols produced in *E. coli* using FARs from *Arabidopsis*. Indeed, it is intended that any suitable method will find use in the present invention and it is not intended that the present invention be limited to any particular method(s) for separating host cells from the nutrient medium.

9. Compositions

In yet another aspect, the present invention relates to the use of the engineered organisms as described herein for the production of various compositions, including but not limited to, fuel compositions (e.g., biodiesels and petrodiesels), cleaning compositions including detergent compositions (e.g., laundry detergents in liquid gel, spray, and powder form, hard surface cleaners, dishwashing detergents, and the like); industrial compositions (e.g., lubricants, solvents, and industrial cleaners); and personal care compositions (e.g., soaps, cosmetics, shampoos, gels, etc.).

Detergent Compositions

In some embodiments, the fatty alcohol compositions described herein, and compounds derived therefrom, can be used as components of detergent compositions. Detergent compositions comprising fatty alcohols and fatty alcohol derivatives produced by the methods of the present invention include compositions used in cleaning applications, including, but not limited to, laundry detergents, handwashing agents, dishwashing detergents, rinse-aid detergents, household detergents, and household cleaners, in liquid, gel, granular, powder, or tablet form. In some embodiments, the fatty alcohols produced by the methods described above are used directly in detergent compositions. In some embodiments, the fatty alcohols and fatty alcohol derivatives are reacted with a sulfonic acid group to produce sulfate derivatives that can be used as components of detergent compositions. Detergent compositions that can be generated using the fatty alcohols and fatty alcohol derivatives produced by the methods of the present invention include, but are not limited to, hair shampoos, rinses, and conditioners for humans and other animals, carpet shampoos, hard surface cleaners, light-duty household cleaners, light-duty household detergents, heavy-duty household cleaners, and heavy-duty household detergents. Detergent compositions generally include, in addition to fatty alcohols and derivative thereof, one or more builders (e.g., sodium carbonate, complexation agents, soap, and zeolites), enzymes (e.g., proteases, lipases, cellulases, and/or amylases); carboxymethyl cellulose, optical brighteners, fabric softeners, colourants and perfumes (e.g., cyclohexyl salicylate). Indeed, it is not intended that the present invention be limited to any particular detergent, detergent formulation, nor detergent use.

In some embodiments, sulfate derivatives (e.g., C12-C15) derived from fatty alcohols are used in products such as hair shampoos, carpet shampoos, light-duty household cleaners, and light-duty household detergents. In some embodiments, sulfate derivatives (e.g., C16-C18) derived from fatty alcohols are used in products such as hair shampoos and conditioners. In some embodiments, sulfate derivatives (e.g., C16-C18) derived from fatty alcohols are used in products such as heavy-duty household cleaners and heavy-duty household detergents. Indeed, it is not intended that the present invention be limited to any particular detergent, detergent formulation, nor detergent use.

Personal Care Compositions

In some embodiments, fatty alcohol compositions as described herein, and compounds derived therefrom, are used as components in personal care compositions. In some embodiments, the fatty alcohols produced by the methods described above are used directly in personal care compositions. Personal care compositions containing fatty alcohols or fatty alcohol derivatives produced by the methods of the present invention include compositions used for application to the body (e.g., for application to the skin, hair, nails, or oral cavity) for the purposes of grooming, cleaning, beautifying, or caring for the body, including but not limited to lotions, balms, creams, gels, serums, cleansers, toners, masks, sunscreens, soaps, shampoos, conditioners, body washes, styling aids, and cosmetic compositions (e.g., makeup in liquid, cream, solid, anhydrous, or pencil form). In some embodiments, the fatty alcohols or fatty alcohol derivatives can be reacted with a sulfonic acid group to produce sulfate derivatives that can be used as components of said compositions. In some embodiments, sulfate derivatives (e.g., C12 to 14) derived from the fatty alcohol compositions produced by the methods described herein are used in products such as toothpastes. Indeed, it is not intended that the present invention be limited to any particular formulation, nor use.

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. Indeed, it is not intended that the present invention be limited to any particular formulation, nor use.

Other Compositions

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. In some embodiments, sulfate derivatives (e.g., C12 to C14) derived from the fatty alcohol compositions produced by the methods described herein are used in products such as toothpastes.

In some instances, fatty alcohols (especially cetyl alcohol, stearyl alcohol and myristyl alcohol) may be used as food additives (e.g., adjuvants and production aids).

Alkane and/or Alkene Compositions

In some embodiments, fatty alcohols produced according to the methods described herein can be reduced to yield alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein.

Any suitable method known in the art can be used to reduce the fatty alcohols. In some embodiments, reduction of fatty alcohols is carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See Li et al., 2007,

*Modern Organic Synthesis in the Laboratory*, p. 81-83. In another embodiment, alkanes are produced by hydrogenation of fatty alcohols.

The alkanes can be isolated from the reaction mixture (which may contain unreduced fatty alcohols) to yield a composition comprising substantially all alkanes. Alternatively, the alkanes and un-reduced fatty alcohols can be isolated from the reaction mixture to yield a composition comprising alkanes and fatty alcohols. In some embodiments, the fatty alcohol compositions comprise at least about 10%, at least about 20%, at least about 30%, at least about 40%, at least about 50%, at least about 60%, at least about 70%, at least about 80%, at least about 85%, at least about 90%, at least about 92%, at least about 95%, at least about 96%, at least about 97%, at least about 98%, or at least about 99% alkanes by weight of the composition after reduction. In some embodiments, the alkane is octane, decane, dodecane, tetradecane, hexadecane, octadecane, icosane, docosane, tetracosane, or mixtures thereof.

Ester Compositions

In other embodiments, fatty alcohols are reacted with a carboxylic acid to form acid esters. Esterification reactions of fatty alcohols are well-known in the art. In certain embodiments, the transesterification reaction is carried out in the presence of a strong catalyst, e.g., a strong alkaline such as sodium hydroxide. In other embodiments, the esterification reaction is carried out enzymatically, using an enzyme that catalyzes the conversion of fatty alcohols to acid esters, such as lipoprotein lipase. See, e.g., Tsujita et al., 1999, "Fatty Acid Alcohol Ester-Synthesizing Activity of Lipoprotein Lipase" J. Biochem. 126:1074-1079.

10. Examples

The following examples are offered to illustrate, but not to limit, the claimed invention.

The present invention is described in further detail in the following Examples, which are not in any way intended to limit the scope of the invention as claimed. In the experimental disclosure below, the following abbreviations apply: ppm (parts per million); M (molar); mM (millimolar); uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) (hour(s)); U (units); LB (Luria-Bertani); MW (molecular weight); rpm (rotations per minute); ° C. (degrees Centigrade); wt % (weight percent); w.r.t. (with regard to); Δ (deletion); DNA (deoxyribonucleic acid); PCR (polymerase chain reaction); RNA (ribonucleic acid); gDNA (genomic DNA); cDNA (complementary DNA); Sigma (Sigma Aldrich, St. Louis, Mo.); Qiagen (Qiagen, Inc., Valencia, Calif.); Invitrogen (Invitrogen, Corp., Carlsbad, Calif.); and Promega (Promega, Corp., Madison, Wis.).

Example 1: Construction of Plasmid pLS8379

To overproduce the FAR enzyme having SEQ ID NO:2 in *E. coli*, a low copy vector carrying the strong Trc promoter was constructed. A DNA fragment containing the lacIq gene, the Trc promoter, and the multiple cloning sites present in pTrcHis2-B (Invitrogen, Carlsbad, Calif.) was PCR amplified using the following primers:

1920TrcM-F
(SEQ ID NO: 17)
5'-GACCTTAAAACCCTAAAGGCTTAAGGGCATCCGCTTACAGACA
and

1920TrcM-R
(SEQ ID NO: 18)
5'-GGAGAAAATACCGCATCAGGCGCCTCAGGAGAGCGTTCACCGAC.

The PCR reaction was carried out using the enzyme Phusion (New England BioLabs, Ipswich, Mass.) with an initial denaturation step at 98° C. for 30 sec, followed by 25 cycles of the steps: 98° C. for 10 sec; 65° C. for 15 sec and 72° C. for 15 sec. This was followed by a final elongation step at 72° C. for 5 min.

The primers used for this PCR reaction carry regions of homology to plasmid pCL1920. Because of this, the PCR product described above can be used as a megaprimer to amplify a defined region of pCL1920 (Lerner and Inouye (1990) NAR 18: 4631) which contains the pSC101 origin of replication and confers resistance to Spectinomycin (GenBank: AB236930). This PCR reaction was carried out using the Pfu Ultra enzyme (Agilent Technologies, Santa Clara, Calif.) with an initial denaturation step at 95° C. for 2 min, followed by 16 cycles of the steps: 95° C. for 30 sec; 55° C. for 30 sec and 68° C. for 7 min. This was followed by a final elongation step at 68° C. for 7 min. The outcome of the second PCR reaction was sequence-verified and the resulting plasmid was named pLS8379 (SEQ ID NO: 15).

Example 2: Construction of pCL5019 Comprising a Polynucleotide Encoding the FAR Variant A synthetic gene (SEQ ID NO: 3) encoding the FAR polypeptide having SEQ ID NO: 4 was ligated as NcoI-SalI fragments to pLS8379 and digested with the same restriction enzymes. Ligation reactions were incubated overnight at 16° C. and transformed into *E. coli* DH10B-T1 electrocompetent cells (Invitrogen, Carlsbad, Calif.) following the manufacturer's protocols. Cells were plated on LB agar plates containing 100 micrograms/ml of Spectinomycin. Plates were incubated overnight at 37° C. Obtained clones were sequence verified.

Example 3: Construction of pCDX11

To obtain a tightly regulated gene expression vector, the $P_{TRC}$ promoter present in pLS8379 was replaced with a synthetic DNA fragment containing a $P_{TRC}$ variant where a symmetrical Lac operator [Sadler et al., 1983, PNAS. 80: 6785-6789] was introduced upstream of the −35 region of $P_{TRC}$. This promoter was synthesized as an EcoRV-NcoI DNA fragment (GeneScript, Piscataway, N.J.) (SEQ ID NO: 19) and used to replace the EcoRV-NcoI region from pLS8379 previously cut with the same restriction enzymes. A ligation reaction containing the two DNA fragments was incubated overnight at 16° C. and then transformed into *E. coli* Top10 electrocompetent cells (Invitrogen, Carlsbad, Calif.) following the manufacturer's protocols. Cells were plated on LB agar plates containing 100 micrograms/ml of Spectinomycin. Plates were then incubated overnight at 37° C. Obtained clones were sequence verified.

```
                                            SEQ ID NO: 19
GATATCTCGGTAGTGGGATACGACGATACCGAAGACAGCTCATGTTATAT

CCCGCCGTTAACCACCATCAAACAGGATTTTCGCCTGCTGGGGCAAACCA

GCGTGGACCGCTTGCTGCAACTCTCTCAGGGCCAGGCGGTGAAGGGCAAT

CAGCTGTTGCCCGTCTCACTGGTGAAAAGAAAAACCACCCTGGCGCCCAA

TACGCAAACCGCCTCTCCCCGCGCGTTGGCCGATTCATTAATGCAGCTGG

CACGACAGGTTTCCCGACTGGAAAGCGGGCAGTAATAATTTAAATTGGTT

TGACAGCTTATCATCGACTGCACGGTGCACCAATGCTTCTGGCGTCAGGC

AGCCATCGGAAGCTGTGGTATGGCTGTGCAGGTCGTAAATCACTGCATAA

TTCGTGTCGCTCAAGGCGCACTCCCGTTCTGGATAATGTTTTTTGCGCCG

ACATAATTGTGAGCGCTCACAATTTCTGAAATGAGCTGTTGACAATTAAT

CATCCGGCTCGTATAATGTGTGGAATTGTGAGCGGATAACAATTTCACAC

AGGAAACAGCGCCGCTGAGAAAAAGCGAAGCGGCACTGCTCTTTAACAAT

TTATCAGACAATCTGTGTGGGCACTCGACCGGAATTATCGATTAACTTTA

TTATTAAAAATTAAAGGAGGAATAAACCATGG
```

Example 4: Construction of pCK900-FadD Plasmid

The plasmid pCK900-FadD which comprises a fadD polynucleotide encoding a FadD enzyme having the amino acid sequence of SEQ ID NO: 8. The native *E. coli* fadD gene (SEQ ID NO: 7) was PCR amplified using the following primers containing SfiI restriction enzyme site:

```
fadD F5-fwd
                                            (SEQ ID NO: 20)
5'ACAATCTAGAGGCCAGCCTGGCCATAAGGAGATATACATATGAAGAAG GTTTGGCTTAACCGTTATCCCGCGG,
and fadD F3-fwd
                                            (SEQ ID NO: 21)
3'ATCATGGTGATGGTGGCCAGTTTGGCCTCATTAGGCTTTATTGTC CA

CTTTGCCGCGCGCTTCG.
```

The PCR product was digested with SfiI restriction enzyme (New England Biolab) and inserted into linearized pCK900i-bla plasmid (SEQ ID NO: 62) with SfiI restriction enzyme.

```
SEQ ID NO: 62_Polynucleotide sequence of
pCK900i-bla.
TCGAGTTAATTAAGGCAGTGAGCGCAACGCAATTAATGTGAGTTAGCTCA

CTCATTAGGCACCCCAGGCTTTACACTTTATGCTTCCGGCTCGTATGTTG

TGTGGAATTGTGAGCGGATAACAATTTCACACAGGAAACAGCTATGACCA

TGATTACGGATTCACTGGCCGTCGTTTTACAATCTAGAGGCCAGCCTGGC

CATAAGGAGATATACATATGAGTATTCAACATTTCCGTGTCGCCCTTATT

CCCTTTTTTGCGGCATTTTGCCTTCCTGTTTTTGCTCACCCAGAAACGCT

GGTGAAAGTAAAAGATGCTGAAGATCAGTTGGGTGCACGAGTGGGTTACA

TCGAACTGGATCTCAACAGCGGTAAGATCCTTGAGAGTTTTCGCCCCGAA

GAGCGTTTTCCAATGATGAGCACTTTTAAAGTTCTGCTATGTGGCGCGGT

ATTATCCCGTGTTGACGCCGGGCAAGAGCAACTCGGTCGCCGCATACACT

ATTCTCAGAATGACTTGGTTGAGTACTCACCAGTCACAGAAAAGCATCTT

ACGGATGGCATGACAGTAAGAGAATTATGCAGTGCTGCCATAACCATGAG

TGATAACACTGCGGCCAACTTACTTCTGACAACGATCGGAGGACCGAAGG

AGCTAACCGTTTTTTTGCACACCATGGGGGATCATGTAACTCGCCTTGAT

CGTTGGGAACCGGAGCTGAATGAAGCCATACCAAACGACGAGCGTGACAC

CACGATGCCTACAGCAATGGCAACAACGTTGCGCAAACTATTAACTGGCG

AACTACTTACTCTAGCTTCCCGGCAACAATTAATAGACTGGATGGAGGCG

GATAAAGTTGCAGGACCACTTCTGCGCTCGGCCCTTCCGGCTGGCTGGTT

TATTGCTGATAAATCTGGAGCCGGTGAGCGTGGGTCTCGCGGTATCATTG

CAGCACTGGGGCCAGATGGTAAGCCCTCCCGTATCGTAGTTATCTACACG

ACGGGGAGTCAGGCAACTATGGATGAACGAAATAGACAGATCGCTGAGAT

AGGTGCCTCACTGATTAAGCATTGGGGCCAAACTGGCCACCATCACCATC

ACCATTAGGGAAGAGCAGATGGGCAAGCTTGACCTGTGAAGTGAAAAATG

GCGCACATTGTGCGACATTTTTTTTGAATTCTACGTAAAAAGCAGCCGA

TACATCGGCTGCTTTTTTTTTGNNNGAGGTTCCAACTTGTGGTATAATGA

AATAAGATCACTCCGGAGCGTATTTTTTGAGTTATCGAGATTTTCAGGAG

CTAAGGAGGAACTAAAATGGAGAAAAAAATCACTGGATATACCACCGTTG

ATATATCCCAATGGCATCGTAAAGAACATTTTGAGGCATTTCAGTCAGTT

GCTCAATGTACCTATAACCAGACCGTTCAGCTGGATATTACGGCCTTTTT

AAAGACCGTAAAGAAAAATAAGCACAAGTTTTATCCGGCCTTTATTCACA

TTCTTGCCCGCCTGATGAATGCTCATCCGGAGTTCCGTATGGCAATGAAA

GACGGTGAGCTGGTGATATGGGATAGTGTTCACCCTTGTTACACCGTTTT

CCATGAGCAAACTGAAACGTTTTCATCGCTCTGGAGTGAATACCACGACG

ATTTCCGGCAGTTTCTACACATATATTCGCAAGATGTGGCGTGTTACGGT

GAAAACCTGGCCTATTTCCCTAAAGGGTTTATTGAGAATATGTTTTTCGT

CTCAGCCAATCCCTGGGTGAGTTTCACCAGTTTTGATTTAAACGTGGCCA

ATATGGACAACTTCTTCGCCCCCGTTTTCACCATGGGCAAATATTATACG

CAAGGCGACAAGGTGCTGATGCCGCTGGCGATTCAGGTTCATCATGCCGT

CTGTGATGGCTTCCATGTCGGCAGAATGCTTAATGAATTACAACAGTACT

GCGATGAGTGGCAGGGCGGGGCGTAACTGCAGGAGCTCAAACAGCAGCCT

GTATTCAGGCTGCTTTTTTCGTTTTGGTCTGCGCGTAATCTCTTGCTCTG

AAAACGAAAAAACCGCCTTGCAGGGCGGTTTTTCGAAGGTTCTCTGAGCT

ACCAACTCTTTGAACCGAGGTAACTGGCTTGGAGGAGCGCAGTCACCAAA

ACTTGTCCTTTCAGTTTAGCCTTAACCGGCGCATGACTTCAAGACTAACT

CCTCTAAATCAATTACCAGTGGCTGCTGCCAGTGGTGCTTTTGCATGTCT

TTCCGGGTTGGACTCAAGACGATAGTTACCGGATAAGGCGCAGCGGTCGG

ACTGAACGGGGGGTTCGTGCATACAGTCCAGCTTGGAGCGAACTGCCTAC

CCGGAACTGAGTGTCAGGCGTGGAATGAGACAAACGCGGCCATAACAGCG

GAATGACACCGGTAAACCGAAAGGCAGGAACAGGAGAGCGCACGAGGGAG

CCGCCAGGGGAAACGCCTGGTATCTTTATAGTCCTGTCGGGTTTCGCCA

-continued

```
CCACTGATTTGAGCGTCAGATTTCGTGATGCTTGTCAGGGGGCGGAGCC

TATGGAAAAACGGCTTTGCCGCGGCCCTCTCACTTCCCTGTTAAGTATCT

TCCTGGCATCTTCCAGGAAATCTCCGCCCCGTTCGTAAGCCATTTCCGCT

CGCCGCAGTCGAACGACCGAGCGTAGCGAGTCAGTGAGCGAGGAAGCGGA

ATATATCCTGTATCACATATTCTGCTGACGCACCGGTGCAGCCTTTTTTC

TCCTGCCACATGAAGCACTTCACTGACACCCTCATCAGTGAACCACCGCT

GGTAGCGGTGGTTTTTTTAGGCCTATGGCCTTTTTTTTTNTGNNAAACC

TTTCGCGGTATGGNATNANAGCGCCCGGAAGAGAGTCAATTAAGAGGGTG

GTGAATGTGAAACCAGTAACGTTATACGATGTCGCAGAGTATGCCGGTGT

CTCTTATCAGACCGTTTCCCGCGTGGTGAACCAGGCCAGCCACGTTTCTG

CGAAAACGCGGGAAAAGTGGAAGCGGCGATGGCGGAGCTGAATTACATT

CCCAACCGCGTGGCACAACAACTGGCGGGCAAACAGTCGTTGCTGATTGG

CGTTGCCACCTCCAGTCTGGCCCTGCACGCGCCGTCGCAAATTGTCGCGG

CGATTAAATCTCGCGCCGATCAACTGGGTGCCAGCGTGGTGGTGTCGATG

GTAGAACGAAGCGGCGTCGAAGCCTGTAAAGCGGCGGTGCACAATCTTCT

CGCGCAACGCGTCAGTGGGCTGATCATTAACTATCCGCTGGATGACCAGG

ATGCCATTGCTGTGGAAGCTGCCTGCACTAATGTTCCGGCGTTATTTCTT

GATGTCTCTGACCAGACACCCATCAACAGTATTATTTTCTCCCATGAAGA

CGGTACGCGACTGGGCGTGGAGCATCTGGTCGCATTGGGTCACCAGCAAA

TCGCGCTGTTAGCGGGCCCATTAAGTTCTGTCTCGGCGCGTCTGCGTCTG

GCTGGCTGGCATAAATATCTCACTCGCAATCAAATTCAGCCGATAGCGGA

ACGGGAAGGCGACTGGAGTGCCATGTCCGGTTTTCAACAAACCATGCAAA

TGCTGAATGAGGGCATCGTTCCCACTGCGATGCTGGTTGCCAACGATCAG

ATGGCGCTGGGCGCAATGCGCGCCATTACCGAGTCCGGGCTGCGCGTTGG

TGCGGACATCTCGGTAGTGGGATACGACGATACCGAAGACAGCTCATGTT

ATATCCCGCCGTTAACCACCATCAAACAGGATTTTCGCCTGCTGGGGCAA

ACCAGCGTGGACCGCTTGCTGCAACTCTCTCAGGGCCAGGCGGTGAAGGG

CAATCAGCTGTTGCCCGTCTCACTGGTGAAAAGAAAAACCACCCTGGCGC

CCAATACGCAAACCGCCTCTCCCCGCGCGTTGGCCGATTCATTAATGCAG

CTGGCACGACAGGTTTCCCGACTGGAAAGCGGGCAGTGAGCGGTACCCGA

TAAAAGCGGCTTCCTGACAGGAGGCCGTTTTGTTTC
```

Ligation reactions were incubated overnight at 16° C. and then transformed into *E. coli* DH10B-T1 electrocompetent cells (Invitrogen, Carlsbad, Calif.) following the manufacturer's instructions. Cells were plated on LB agar plates containing 30 ug/ml of chloramphoenicol and 1% glucose. Plates were incubated overnight at 37° C. Obtained clones were sequence verified.

Example 5: Construction of pCDX11-7076 Plasmid

The plasmid pCDX11-7076 comprising the FAR-V2 polynucleotide of SEQ ID NO:5 encoding the FAR-V2 enzyme having the amino acid sequence of SEQ ID NO:6 was constructed as described below. A DNA fragment containing the FAR-V2 gene was PCR amplified using the following primers:

```
7076_NcoI_F
                                           (SEQ ID NO: 22)
5'-TAAACCATGGCGACTCAACAACAGAACA,
and 7076_SalI_R
                                           (SEQ ID NO: 23)
5'-CTATGTCGACTTAGGCGGTTTTATCGTCAGTATCA.
```

The restriction enzyme sites NcoI and SalI were incorporated into 7076_NcoI_F and 7076_SalI_R respectively, allowing ligation into pCDX11 (See, example 3) digested with NcoI and SalI. Ligation reactions were incubated overnight at 16° C. and then transformed into *E. coli* TOP10 chemically competent cells (Invitrogen, Carlsbad, Calif.) using standard techniques. Cells were plated on LB agar plates containing 100 ug/ml of Spectinomycin and incubated overnight at 37° C. Obtained clones were sequence verified. The cycling conditions and reactions were applied according to the manufacturers' instructions, unless otherwise specified.

Example 6: Construction of pCDX11-7076-BTE-FadD Plasmid

The plasmid pCDX11-7076-BTE-FadD comprising a polynucleotide (SEQ ID NO: 34) encoding an acyl-ACP thioesterase (BTE) from *Umbellularia californica* having the amino acid sequence of SEQ ID NO: 35 and a polynucleotide (SEQ ID NO: 7) encoding a FadD enzyme having the amino acid sequence of SEQ ID NO: 8 was constructed by cloning these two polynucleotides into pCDX11-7076 that was shown in example 5.

The polynucleotide encoding DNA sequence of BTE (SEQ ID NO:34) was synthesized by GenScript (Piscataway, N.J.) and the synthesized gene was PCR amplified using the following primers:

```
BTE2_SalI_F
                                           (SEQ ID NO: 24)
5'-TGATACTGACGATAAAACCGCCTAAGTCGACAAGGAGGAATAAAC
CATGACAATGATTACGCCGAGCT,
and BTE_R
                                           (SEQ ID NO: 25)
5'-TTATACCCGCGGCTCGGCCGG.
```

The native *E. coli* fadD gene (SEQ ID NO: 7) was PCR amplified from pCK900-FadD (shown in example 4) plasmid using the following primers:

```
7076_fadD_F
                                           (SEQ ID NO: 26)
5'-CCGGCCGAGCCGCGGGTATAAAAGGAGATATACA
TATGAAGAAGGTTTGGCTTAACCG,
and fadD_BglII_R
                                           (SEQ ID NO: 27)
5'-CCGAGTAAGTTCTAGATCTTCATTAGGCTTTATTG TCCACTTTGC.
```

These two PCR amplified fragments were combined using SOE PCR (splicing by overlap extension PCR) standard protocol (See, Warrens et al., 1997 Gene 186(1):29) and gel purified using NucleoSpin Extract II kit (Clontech Laboratories Inc. Mountain View, Calif.) and then 250 ng of the purified PCR product was inserted into 150 ng of linearized pCDX11-7076 plasmid with SalI and BglII restriction enzymes using the CloneEZ Kit (GenScript, Piscataway, N.J.) according to manufacturer's instructions. The CloneEZ reaction mixture was transformed into chemically competent E. coli TOP10 (Invitrogen, CA) cells using standard molecular biology methods. The transformed cells were plated on LB agar plates containing 100 µg/ml of spectinomycin. Plates were incubated overnight at 37° C. Clones were sequence-verified and the plasmid was named pCDX117076-BTE-FadD.

Example 7: Construction of pCDX11-5019 Plasmid

The plasmid pCDX11-5019 comprising the FAR-V1 polynucleotide of SEQ ID NO:3 encoding the FAR-V1 enzyme having the amino acid sequence of SEQ ID NO:4 was constructed as described below. A DNA fragment containing the FAR-V1 gene was PCR amplified using the following primers:

```
5019_NcoI_F
                                      (SEQ ID NO: 28)
5'-tgtggaattgtgagcggata
and 5019_SalI_R
                                      (SEQ ID NO: 29)
5'-CGCTTCTGCGTTCTGATTT.
```

The restriction enzyme sites NcoI and SalI were incorporated into 5019_NcoI_F and 5019_SalI_R respectively, allowing ligation into pCDX11 (See, example 3) digested with NcoI and SalI. Ligation reactions were incubated overnight at 16° C. and then transformed into E. coli TOP10 chemically competent cells (Invitrogen, Carlsbad, Calif.) using standard techniques. Cells were plated on LB agar plates containing 100 ug/ml of Spectinomycin and incubated overnight at 37° C. Obtained clones were sequence verified. The cycling conditions and reactions were applied according to the manufacturers' instructions, unless otherwise specified.

Example 8: Construction of pCDX11-5019-BTE-FadD Plasmid

The plasmid pCDX11-5019-BTE-FadD comprising a polynucleotide (SEQ ID NO: 34) encoding an acyl-ACP thioesterase (BTE) from Umbellularia californica having the amino acid sequence of SEQ ID NO: 35 and a polynucleotide (SEQ ID NO: 7) encoding a FadD enzyme having the amino acid sequence of SEQ ID NO: 8 was constructed by cloning these two polynucleotides into pCDX11-5019 that was shown in Example 7.

The polynucleotide encoding DNA sequence of BTE (SEQ ID NO:34) was synthesized by GenScript (Piscataway, N.J.) and the synthesized gene was PCR amplified using the following primers:

```
BTE_SalI_F
                                      (SEQ ID NO: 30)
5' TGATACTGACGATAAAACCGCCTAAGTCGACAAGGAGGAATAAACCA
TGACCTTAGAGTGGAAACCAAAAC,
and BTE_R
                                      (SEQ ID NO: 31)
5'-TTATACCCGCGGCTCGGCCGG.
```

The native E. coli fadD gene (SEQ ID NO: 7) was PCR amplified from pCK900-FadD (shown in example 4) plasmid using the following primers:

```
5019_fadD_F
                                      (SEQ ID NO: 32)
5'-CCGGCCGAGCCGCGGGTATAAAAGGAGATATACATATGAAGAAGGTT
TGGCTTAACCG
and fadD_BglII_R
                                      (SEQ ID NO: 33)
5'-CCGAGTAAGTTCTAGATCTTCATTAGGCTTTATTGTCCACTTTGC.
```

These two PCR amplified fragments were combined using SOE PCR (splicing by overlap extension PCR) standard protocol (See, Warrens et al., 1997 Gene 186(1):29) and gel purified using NucleoSpin Extract II kit (Clontech Laboratories Inc. Mountain View, Calif.) and then 250 ng of the purified PCR product was inserted into 150 ng of linearized pCDX11-5019 plasmid with SalI and BglII restriction enzymes using the CloneEZ Kit (GenScript, Piscataway, N.J.) according to manufacturer's instructions. The CloneEZ reaction mixture was transformed into chemically competent E. coli TOP10 (Invitrogen, CA) cells using standard molecular biology methods. The transformed cells were plated on LB agar plates containing 100 µg/ml of spectinomycin. Plates were incubated overnight at 37° C. Clones were sequence-verified and the plasmid was named pCDX11-5019-BTE-FadD.

Example 9: Generating W3110 ΔfhuA Strain Harboring pCDX117076-BTE-FadD Plasmid or pCDX115019-BTE-FadD Plasmid Electrocompetent cells of E. coli W3110 ΔfhuA were prepared as follows. The culture was grown in LB media to an $OD_{600}$ of ~0.6 and concentrated 100-fold by centrifugation. The cells were washed three times with ice-cold sterile water, and then washed once with ice-cold 10% glycerol. The plasmid pCDX11-7076-BTE-FadD (see examples 6 and 7) was introduced into the electrocompetent E. coli W3110 ΔfhuA using standard molecular biology methods (Dower et al., 1988 NAR 16:6127-6145).

Example 10: Fatty Alcohol Production

Recombinant E. coli host strains comprising a plasmid including heterologous genes as specified were grown in M9 medium supplemented with 1% glucose, 2 g/L yeast extract and the specified antibiotic selection, for approximately 16-18 hours (overnight) at 30° C., 200 rpm. A 5% inoculum was used to initiate fresh M9 media, 5% glucose and 2 g/L yeast extract containing the specified antibiotic. The culture was incubated in a shaker for 2.5 hours at 30° C. and at 250 rpm to an $OD_{600}$ of about 0.6 to about 0.8. The expression of the heterologous FAR was then induced with isopropyl-β-D-thiogalactoside (IPTG) (1 mM final concentration). Incubation was continued for about 48 hours under the same conditions. Fatty acid species including fatty alcohols were extracted using 1 mL of methyl isobutyl ketone (MIBK) into 500 µl of cell culture, sealed tightly and shaken for ≥2.5 h. The extract was centrifuged and analyzed directly by GC-FID. A 1 µL sample was analyzed by GC-FID with the split ratio 1:10 using the following conditions: GC-6890N from Agilent Technologies equipped with FID detector and HP-5 column (length 30 m, I.D. 0.32 mm, film 0.25 µm). GC method: start at 100° C., increase the temperature with a rate of 25° C./min to 246° C. and hold for 1.96 min. Total run time was 7.8 min Under the above GC conditions, the approximate retention times (min) of produced fatty alcohols and acids were as follows: 1.81, C10:0-OH; 2.47, C12:0-OH; 5.08, C14:0-OH; 5.40, C14:0-OOH; 5.74, C16:1-OH; 5.93, C16:0-OH; 6.11, C16:0-OOMe (internal standard); 6.16, C16:1-OOH; 6.29, C16:0-OOH; 6.80, C18:1-OH; 6.90, C18:0-OH; and 7.3, C18:0- and C18:1-OOH. The results of fatty alcohol production under these conditions are depicted in Table 1. Identification of individual fatty alcohols was determined by comparison to commercial standards (Sigma Chemical Company, 6050 Spruce St. Louis, Mo. 63103).

Strain W3110K was transformed with plasmid pSIM5 (Datta et al., supra). Homologous recombination-proficient electrocompetent cells were prepared as described by Datta et al., (supra), and were transformed with 500 ng of the kanamycin cassette. Cells were recovered at 32° C. for three hours, plated on LB agar plates containing 20 ug/ml of kanamycin, and incubated 24 hours at 32° C. A single colony was streaked onto a fresh LB agar plate with 30 ug/ml chloramphenicol (to maintain the pSIM5 plasmid) and a

TABLE 1

Fatty alcohol production when glucose is the carbon source.

| Strain | % saturation | % C12—OH | % C14 | % C16 | % C18 |
|---|---|---|---|---|---|
| W3110 ΔfhuA strain harboring pCDX115019 | 62.6 ± 0.2 | 0.8 ± 0.2 | 42.2 ± 0.3 | 52.3 ± 0.3 | 4.6 ± 0.05 |
| W3110 ΔfhuA strain harboring pCDX115019-BTE-FadD | 61 ± 0.05 | 29 ± 0.2 | 29.1 ± 0.3 | 38.4 ± 0.2 | 3.3 ± 0.1 |
| W3110 ΔfhuA strain harboring pCDX117076 | 61.8 ± 0.6 | 8.9 ± 0.1 | 56.7 ± 0.2 | 32.8 ± 0.1 | 1.7 ± 0.03 |
| W3110 ΔfhuA strain harboring pCDX117076-BTE-FadD | 63 ± 0.3 | 30 ± 0.6 | 39.8 ± 0.3 | 28.5 ± 0.2 | 1.5 ± 0.02 |

% as measured by calculating the individual fatty alcohols as part of the sum of all fatty alcohol measured.
% C10 and % C12—OOH were not detectable.

Example 11: Construction of W3110K Δ4 Strain

Experiments conducted to construct the *E. coli* strain W3110K-Δ4 which is also suitable for large-scale fermentation processes are described below. Four deletions were made to the *E. coli* W3110K (CGSC): ΔfhuA; ΔldhA; ΔadhE and genes involved in colanic acid biosynthesis Δwza-wcaM. Each of the four deletions was carried out in a two-step process using lambda-RED technology known in the art (See, Datta et al., Gene 379:109-115 (2006)). In the first step, the gene(s) of interest was replaced with a dsDNA cassette encoding a kanamycin resistance marker (Km). In the second step, the Km marker was seamlessly removed from the genome using a ssDNA oligo using methods known in the art (See, Datta et al., supra). To exemplify this process, the deletion of the fhuA gene is described below.

For the deletion of fhuA, a dsDNA kanamycin resistance cassette was first PCR amplified from plasmid pKD13 (CGSC) using the following primers:

fhuA-deletion_F:
(SEQ ID NO: 40)
5' ACGTTATCATTCACTTTACATCAGAGATATACCAATGGCGATTCCGG
GGATCCGTCGACC-3' fhuA-deletion_R:
(SEQ ID NO: 41)
5' AGAGAAATTAGAAACGGAAGGTTGCGGTTGCAACGACCTGTGTAGGC
TGGAGCTGCTTCG-3'

The PCR reaction was carried out using the enzyme PHUSION® DNA polymerase (New England BioLabs) with an initial denaturation step at 98° C. for 30 sec, followed by 30 cycles of the steps: 98° C. for 5 sec; 63° C. for 20 sec and 72° C. for 40 sec. This was followed by a final elongation step at 72° C. for 5 min. After the PCR reaction, the PCR product was purified through a PCR purification column (Qiagen) and eluted with water.

purified colony confirmed to have the fhuA gene replaced with the kanamycin cassette was named W3110K-ΔfhuA::Km.

The kanamycin marker was removed from the cells using homologous recombination with a ssDNA oligonucleotide. Homologous recombination proficient electrocompetent cells were prepared from strain W3110K-ΔfhuA::Km with the pSIM5 plasmid as described above and the cells were transformed with 500 ng of the oligonucleotide (fhuA(2-10)_del_oligo) shown below. In this sequence, the "*" indicates the presence of phosphorothioate bonds. This oligonucleotide contains four bases that were modified during synthesis of the oligonucleotide by the manufacturer (GenScript). It is known that these modifications make the oligonucleotide resistant to certain cellular nucleases.

fhuA(2-10)_del_oligo:
(SEQ ID NO: 42)
5'-A*G*A*G*AAATTAGAAACGGAAGGTTGCGGTTGCAACGACCTGCGC
CATTGGTATATCTCTGATGTAAAGTGAATGATAACGT-3'

Cells were recovered at 32° C. for five hours and dilutions were plated on LB agar plates and incubated 24 hours at 32° C. Petri plates with cell dilutions resulting in about 500 colonies/dish were replica plated onto fresh LB (Difco) and LA (Difco) plus kanamycin plates. A kanamycin sensitive colony was struck onto a fresh LA (Difco) plate with 30 micrograms/ml chloramphenicol (to maintain the pSIM5 plasmid) and a purified colony confirmed to have the correct, seamless deletion of the Km cassette, was named W3110K-ΔfhuA.

The subsequent deletions of the ldhA and adhE genes and all the genes of the region wza to wcaM were performed as described above for the fhuA gene. The primers for amplifying the dsDNA cassette from pKD13 and the oligos used for the seamless deletion of the markers, are shown below for each of the ldhA and adhE genes and the wza-wcaM genes:

ldhA-deletion_F:
(SEQ ID NO: 43)
5' AGCTTAAATGTGATTCAACATCACTGGAGAAAGTCTTATGATTCCGG
GGATCCGTCGACC-3';

ldhA-deletion_R:
(SEQ ID NO: 44)
5' ATGCAGGGGAGCGGCAAGATTAAACCAGTTCGTTCGGGCATGTAGGC
TGGAGCTGCTTCG-3';

ldhA(1-6)_del_oligo:
(SEQ ID NO: 45)
5' A*G*C*T*TAAATGTGATTCAACATCACTGGAGAAAGTCTTATGTGC
CCGAACGAACTGGTTTAATCTTGCCGCTCCCCTGCAT-3'
(* = phosphorothioate bonds);

adhE-deletion_F:
(SEQ ID NO: 46)
5' ATTTACTAAAAAAGTTTAACATTATCAGGAGAGCATTATGATTCCGG
GGATCCGTCGACC-3';

adhE-deletion_R:
(SEQ ID NO: 47)
5' TGCCAGACAGCGCTACTGATTAAGCGGATTTTTTCGCTTTTGTAGGC
TGGAGCTGCTTCG-3';

adhE(1-6)_del_oligo:
(SEQ ID NO: 48)
5' A*T*T*T*ACTAAAAAAGTTTAACATTATCAGGAGAGCATTATGAAA
GCGAAAAAATCCGCTTAATCAGTAGCGCTGTCTGGCA-3'
(* = phosphorothioate bonds);

wza-deletion_F:
(SEQ ID NO: 49)
5' AGGATAATTACTCTGCCAAAGTGATAAATAAACAATGATGATTCCGG
GGATCCGTCGACC-3';

wcaM-deletion_R:
(SEQ ID NO: 50)
5' GCAATCTAAAGTTAATCTTCTCCACATTAACAATATGGTGTGTAGGC
TGGAGCTGCTTCG-3';
and wza-wcaM(2-18)_del_oligo:
(SEQ ID NO: 51)
5' G*C*A*A*TCTAAAGTTAATCTTCTCCACATTAACAATATGGTGCAT
CATTGTTTATTTATCACTTTGGCAGAGTAATTATCCT-3',
(* = phosphorothioate bonds).

The final strain was confirmed by DNA sequencing to have seamless deletions of all four loci and was named "W3110K-Δ4" (W3110K-ΔfhuA-ΔldhA-ΔadhE-ΔwzawcaM).

Example 12: Construction of pCDX11-8087-MCS Plasmid

The plasmid pCDX11-8087-MCS comprising a polynucleotide (SEQ ID NO:36) encoding FAR-V3 (SEQ ID: 37) was constructed as follows: A DNA fragment containing the FAR-V3 gene was PCR amplified using the primers:

8087_NcoI_F:
(SEQ ID NO: 52)
5' TAAACCATGGCGACTCAACAACAGAACA
and

8087_SalI_R:
(SEQ ID NO: 53)
5' CTATGTCGACTTAGGCGGTTTTATCGTCAGTATCA.

The PCR reaction was carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. This was followed by a final extension step at 72° C. for 5 min. After PCR, the resulting DNA fragment was purified by gel-extraction using a Zymoclean Gel DNA Recovery Kit. As the restriction enzyme sites NcoI and SalI were incorporated into the primers 8087_NcoI_F and 8087_SalI_R respectively, this allowed the ligation of this PCR product into pCDX11 digested with NcoI and SalI restriction enzymes accordingly the manufacturer conditions (New England BioLabs, Ipswich, Mass.). Ligation reactions were incubated overnight at 16° C. and then transformed into E. coli TOP10 chemically competent cells (Invitrogen, Carlsbad, Calif.) using standard techniques. Cells were plated on LB agar plates containing 100 ug/ml of Spectinomycin and incubated overnight at 37° C. Obtained clones were sequence verified. A clone with the correct sequence was designated pCDX11-8087-MCS.

Example 13: Construction of pCDX11-8087-BTE-fadD

To produce fatty alcohols from acyl-CoA intermediates instead of acyl-ACP intermediates using FAR-V3 variant, a plasmid overexpressing FAR-V3, the California Bay tree thioesterase (BTE) and the E. coli acyl-CoA synthase gene (FadD) was constructed as follows. The polynucleotide encoding variant FAR-V3 (SEQ ID NO: 36) was PCR amplified using pCDX118087-MCS described in Example 11 above, using the following primers:

5' cloning site + RBS1:FAR 8087-
(SEQ ID NO: 54)
5'ccggaattatcgattaactttattattaaaaattaaaggaggaataaa
ccatggcgactcaacaacagaac,
and FAR 8087:RBS-ptrc-
(SEQ ID NO: 55)
3'taaggtcatggtttattcctccttgtcgacttaggcggttttatcgtc
agtatc.

The polynucleotide encoding the BTE thioesterase (SEQ ID NO: 35) was synthesized by GenScript (Piscataway, N.J.), and the synthesized gene was amplified by PCR using the following primers:

RBS-ptrc:CaBayTES1-
(SEQ ID NO: 56)
5'ACCGCCTAAGTCGACAAGGAGGAATAAACCATGACCTTAGAGTGGAA
ACCAAAA
and CaBayTES1:RBS-pCK
(SEQ ID NO: 57)
3'GCCAAACCTTCTTCATATGTATATCTCCTTTTATACCCGCGGCTCGG.

The native E. coli fadD gene (SEQ ID NO:7) was PCR amplified from E. coli genomic DNA using the following primers:

RBS-pCK:fadD-
(SEQ ID NO: 58)
5'CGAGCCGCGGGTATAAAAGGAGATATACATATGAAGAAGGTTTGGC
TTAACCG
and fadD:3'cloning site-
(SEQ ID NO: 59)
3'TTAAGAAGCTTCCGAGTAAGTTCTAGATCTTCATTAGGCTTTATTG
TCCACTTTG.

PCR amplifications were performed with Herculase II (Agilent Technologies, Santa Clara, Calif.) following manufacturer's protocol with at 60° C. annealing temp. These three PCR amplified fragments were combined using SOE PCR (splicing by overlap extension PCR) standard protocol (see, Warrens et al., 1997 Gene 186(1):29) using primers 5' cloning site+RBS1:FAR 8087 5' and fadD:3' cloning site 3' mentioned above. The final PCR product was inserted into linearized pCDX11 plasmid with ClaI and BglII restriction enzymes from Fermentas (Thermo Scientific, Glen Burnie, Md.), ligated overnight at 16° C. with T4 DNA ligase per manufacturer's protocol (NEB, Ipswich, Mass.), and transformed into electrocompetent W3110 ΔfhuA using standard molecular biology methods (Dower et al., 1988 NAR 16:6127-6145). Cells were plated on LB agar plates containing 100 ug/ml of spectinomycin and plates were incubated overnight at 37° C. Clones were sequence-verified and the plasmid named pCDX118087-BTE-fadD.

Example 14: Construction of pCDX11-13013-BTE-fadD

Plasmid pCDX11-13013-BTE-fadD was constructed by replacing FAR-V3 present in plasmid pCDX11-8087-BTE-fadD described in example 13, with a polynucleotide sequence (SEQ ID NO: 38) encoding FAR-V4 (SEQ ID NO: 39) as described below.

The FAR-V4 was PCR amplified with the following oligos:

pCDX11-FAR_F:
(SEQ ID NO: 60)
5'-ACAATCTGTGTGGGCACTCG-3';

13013-TES_R:
(SEQ ID NO: 61)
5'-TCATGGTTTATTCCTCCTTGTCGACTTAGGCAATTTCATCGTCATGA
TCA-3'.

The PCR reaction was carried out using the enzyme Herculase II Fusion DNA polymerase (Agilent Technologies, Inc., Santa Clara, Calif.) with an initial denaturation step at 94° C. for 2 min, followed by 25 cycles of the steps: 94° C. for 30 sec; 56° C. for 30 sec and 72° C. for 2 min. The denaturation step was followed by a final elongation step at 72° C. for 3 min. The resulting PCR product was cleaned with ExoSAP-IT (Affymetrix, Santa Clara, Calif.) and the remaining template was digested with DpnI (Promega, Madison, Wis.).

Five microliters of cleaned PCR product was added to 10 ng of plasmid pCDX11-8087-CaBayTES1-fadD. The mixture was PCR amplified using the enzyme Phusion DNA polymerase (New England BioLabs, Ipswich, Mass.) with an initial denaturation step at 98° C. for 30 sec, followed by 40 cycles of the steps: 98° C. for 10 sec; 72 for 3 min. The denaturation step was followed by a final elongation step at 72° C. for 5 min. After the PCR reaction, the product was digested with DpnI (Promega, Madison, Wis.). This reaction was transformed into E. coli DH10B electrocompetent cells (Invitrogen, Carlsbad, Calif.) following the manufacturer's protocols. Cells were plated on LB agar plates containing 50 micrograms/ml of carbenicillin and incubated for 24 hours at 30° C. Plasmid from an obtained clone was sequence verified and named pCDX11-13013-BTE-fadD.

Example 15: C12 Fatty Alcohol Production

FAR-V3 and FAR-V4 were selected for their higher specificity to produce C12-OH at high titer. To evaluate their performance in the presence of a C12-specific thioesterase, plasmids pCDX11-8087-BTE-fadD and pCDX11-13013-BTE-fadD described in Examples 13 and 14, were transferred to E. coli strain W3110K-Δ4 described in Example 11 and evaluated under the conditions described in Example 10.

TABLE 2

C12—OH Fatty Alcohol Production

| Strain W3110K Δ4 | Total Fatty Alcohol g/L | C12—OH Fatty Alcohol g/L | % C12—OH of Total Fatty Alcohols |
|---|---|---|---|
| harboring pCDX11-8087-BTE-FadD | 2.3 | 0.53 | 23 |
| harboring pCDX11-13013-BTE-FadD | 2.1 | 1.2 | 57 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention.

SEQUENCE LISTING

<160> NUMBER OF SEQ ID NOS: 62

<210> SEQ ID NO 1
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 1

```
atggctactc aacaacaaca gaacggtgca tctgcatccg gcgtcttgga acaacttcgt      60
ggaaagcacg ttcttatcac aggtactacc ggattttttgg gcaaagtggt tctggaaaag     120
ttgattcgta ctgttccgga tattggaggt attcatctgc tgattcgtgg caataaacgt     180
catccagccg ctcgtgaacg tttcctgaac gaaattgcgt cctcctccgt cttcgaacgt     240
```

```
ttgcgtcacg atgataatga agccttcgag accttcttgg aagaacgtgt tcactgtatt    300
accggtgagg ttactgaatc ccgttttggt ttgacacctg aacgttttcg tgctttggcc    360
ggtcaggttg acgcttttat taacagcgct gcaagcgtga actttcgtga ggaattggat    420
aaagccctga aaatcaacac cttgtgtctt gaaaatgttg ctgctcttgc agaattgaac    480
tccgctatgg cggtcattca ggtttccact tgttacgtta acggtaaaaa ctccggtcaa    540
attaccgaat ccgtcattaa acctgctggc gaatccattc cccgttccac tgacggttac    600
tacgagatcg aagaattggt ccatctgttg caagacaaga tttccgatgt taaagctcgt    660
tactccggca agttctgga gaaaaaattg gttgatttgg gtattcgtga ggccaataat    720
tacggatggt ccgacaccta cattcacc aaatggttgg gtgaacaact gctgatgaag    780
gccttgtctg gtcgttcttt gactattgtg cgtccctcta ttattgagtc cgctttggaa    840
gaaccttccc ctggttggat cgaaggcgtt aaagttgccg atgccattat cttggcttat    900
gcccgtgaaa aagttagcct gttccctgga aacgttccg gcattattga tgttattcct    960
gtcgatttgg ttgcgaactc catcatcttg tctctggctg aggcgttgtc tggttctggt    1020
caacgtcgta tttatcaatg ttgcagcggt ggttctaatc caatctccct gggtaagttc    1080
attgattatt tgatggccga ggctaagacc aactatgctg cctacgatca actgttttat    1140
cgtcgtccta ctaaacctt cgtcgccgtg aaccgtaaat tgtttgacgt tgttgttggt    1200
ggtatgcgtg ttcctctttc tattgccggt aaagctatgc gtttggctgg tcaaaatcgt    1260
gagttgaaag tgcttaagaa ccttgatacg acccgttccc ttgcaaccat ttttggcttc    1320
tatactgctc ccgactatat cttccgtaac gatagcttga tggccctggc ttctcgtatg    1380
ggtgaattgg atcgtgttct tttcccagtt gatgctcgtc aaattgattg gcagttgtac    1440
ttgtgtaaaa ttcatttggg tggtctgaac cgttacgctt tgaaggaacg taaactgtat    1500
tctttgcgtg ctgctgatac tcgtaaaaaa gctgcctaa                         1539

<210> SEQ ID NO 2
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 2

Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
```

```
            130                 135                 140
Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 3
<211> LENGTH: 1547
<212> TYPE: DNA
<213> ORGANISM: Artificial Sequence
<220> FEATURE:
<223> OTHER INFORMATION: Synthetic polynucleotide
```

-continued

```
<400> SEQUENCE: 3
ccatggcgac tcaacaacag cagaacggtg catctgcatc cggcgtcttg gaacaacttc     60
gtggaaagca cgttcttatc acaggtacta ccggattttt gggcaaagtg gttctggaaa    120
agttgattcg tactgttccg gatattggag gtattcatct gctgattcgt ggcaataaac    180
gtcatccagc cgctcgtgaa cgtttcctga cgaaattgc gtcctcctcc gtcttcgaac     240
gtttgcgtca cgatgataat gaagccttcg agaccttctt ggaagaacgt gttcactgta    300
ttaccggtga ggttactgaa tcccgttttg gtttgacacc tgagcgtttt cgtgctttgg    360
ccggtcaggt tgacgctttt attaacagcg ctgcaagcgt gagttttcgt gagcaattgg    420
ataaagccct gaaaatcaac accttgtgtc ttgaaaatgt tgctgctctt gcagaattga    480
actccgctat ggcggtcatt caggtttcca cttgttacgt taacggtaaa aactccggtc    540
aaattaccga atccgtcatt aaatcggctg gcgaatccat tccccgttcc actgacggtt    600
actacgagat cgaagaattg gtccatctgt tgcaagacaa gatttccgat gttaaagctc    660
gttactccgg caaagttctg gagaaaaaat tggttgattt gggtattcgt gaggccaata    720
attacggatg gtccgacacc tacacattca ccaaatggtt gggtgaacaa ctgctgatga    780
aggccttgtc tggtcgttct ttgactattg tgcgtccctc tattattgag tccgctttgg    840
aagaaccttc ccctggttgg atcgaaggcg ttaaagttgc cgatgccatt atcttggctt    900
atgcccgtga aaaagttagc ctgttccctg gaaaacgttc cggcattatt gatgttattc    960
ctgtcgattt ggttgcgaac tccatcatct tgtctctggc tgaggcgttg tctggttctg   1020
gtcaacgtcg tatttatcaa tgttgcagcg gtggttctaa tccaatctcc ctgggtaagt   1080
tcattgatta tttgatggcc gaggctaaga ccaactatgc tgcctacgat caactgtttt   1140
atcgtcgtcc tactaaacct ttcgtcgccc tgaaccgtaa attgtttgac gttgttgttg   1200
gtggtatgcg tgttgtcctt tctattgccg gtaaagctat gcgtttggct ggtgtaaatc   1260
gtgagttgaa agtgcttaag aaccttgata cgacccgtaa acttgcaacc attttttggct  1320 tctatactgc tcccgactat atcttccgta acgatagctt gatggccctg gctcagcgta   1380
tgggtgaatt ggatcgtgtt cttttcccag ttgatgctcg tcaaattgat tggcagttgt   1440
acttgtgtaa aattcatttg ggtggtctga accgttacgc tttgaaggaa cgtaaactgt   1500
attcttcgcg tgctgctgat actgacgata aaaccgccta agtcgac                 1547
```

<210> SEQ ID NO 4
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 4

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80
```

```
Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Ser Phe Arg Glu Gln Leu Asp Lys Ala Leu Lys
130                 135                 140

Ile Asn Thr Leu Cys Leu Glu Asn Val Ala Leu Ala Glu Leu Asn
145                 150                 155                 160

Ser Ala Met Ala Val Ile Gln Val Ser Thr Cys Tyr Val Asn Gly Lys
            165                 170                 175

Asn Ser Gly Gln Ile Thr Glu Ser Val Ile Lys Ser Ala Gly Glu Ser
        180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
            245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
            325                 330                 335

Ser Gly Ser Gly Gln Arg Arg Ile Tyr Gln Cys Cys Ser Gly Gly Ser
        340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Val Leu Ser Ile Ala Gly Lys Ala Met Arg Leu Ala
            405                 410                 415

Gly Val Asn Arg Glu Leu Lys Val Leu Lys Asn Leu Asp Thr Thr Arg
        420                 425                 430

Lys Leu Ala Thr Ile Phe Gly Phe Tyr Thr Ala Pro Asp Tyr Ile Phe
    435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
            485                 490                 495

Arg Lys Leu Tyr Ser Ser Arg Ala Ala Asp Thr Asp Asp Lys Thr Ala
```

<210> SEQ ID NO 5
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 5

```
atggcgactc aacaacagaa caacggtgca tctgcatccg gcgtcttgga aattcttcgt      60
ggaaagcacg ttcttatcac aggtactacc ggatttttgg gcaaagtggt tctggaaaag     120
ttgattcgta ctgttccgga tattggaggt attcatctgc tgattcgtgg caataaacgt     180
catccagccg ctggcgaacg tttcctgaac gaaattgcgt cctcctccgt cttcgaacgt     240
tgcgtcacg atgataatga agccttcgag accttcttgg aagaacgtgt tcactgtatt      300
accggtgagg ttactgaatc ccgttttggt ttgacacctg agcgttttcg tgctttggcc     360
ggtcaggttg acgcttttat tcatagcgct gcaagcgtga actttcgtga gcaattggat     420
aaagccctga aaatcaacac cttgtgtctt gaaaatgttg ctgctcttgc agaattgaac     480
tccgctatgg cggtcattca ggtttccact tgttacgtta acggtaaaac ctccggtcaa     540
attaccgaat ccgtcattaa atcggctggc gaatccattc ccgttccac tgacggttac      600
tacgagatca agaattggt ccatctgttg caagacaaga tttccgatgt aaagctcgt      660
tactccggcc gtgttatggg gaaaaaattg gttgatttgg gtattcgtga ggccaataat     720
tacggatggt ccgacaccta cacattcacc aaatggttgg gtgaacaact gctgatgaag     780
gccttgtctg gtcgttcttt gactattgtg cgtccctcta ttattgagtc cgctttggaa     840
gaaccttccc ctggttggat cgaaggcgtt aaagttgccg atgccattat cttggcttat     900
gcccgtgaaa aagttagcct gttccctgga aaacgttccg gcattattga tgttattcct     960
gtcgatttgg ttgcgaactc catcatcttg tctctggctg aggcgttgtc tggttctggt    1020
caacgtcgta tttatcaatg ttgcagcggt ggttctaatc caatctccct gggtaagttc    1080
attgattatt tgaacgccga ggctaagacc aactatgctg cctacgatca actgttttat    1140
cgtcgtccta ctaaaccttt cgtcgccgtg aaccgtaaat tgtttgacgt tgttgttggt    1200
gtcatgcgtt tgtccttttc tattgccggt aaagctatgc gtttggctgg tgtaaatcgt    1260
gagttgaaag tgcttaagaa ccttgatacg acccgtaaac ttgcaaccat ttttggcttc    1320
tatactgctc ccgactatat cttccgtaac gatagcttga tggccctggc tcagcgtatg    1380
ggtgaattgg atcgtgttct ttcccagtt gatgctcgtc aaattgattg gcagttgtac    1440
ttgtgtaaaa ttcatttgcg tggtctgaac cgttacgctt tgaaggaacg taaactgtat    1500
tcttcgcgtg ctgctgatac tgacgataaa accgcctaa                           1539
```

<210> SEQ ID NO 6
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 6

```
Met Ala Thr Gln Gln Gln Asn Asn Gly Ala Ser Ala Ser Gly Val Leu
1               5                   10                  15
Glu Ile Leu Arg Gly Lys His Val Leu Ile Thr Gly Thr Thr Gly Phe
            20                  25                  30
```

```
Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Gly Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
                100                 105                 110

Pro Glu Arg Phe Arg Ala Leu Ala Gly Gln Val Asp Ala Phe Ile His
                115                 120                 125

Ser Ala Ala Ser Val Asn Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Thr Ser Gly Gln Ile Thr Glu Ser Val Ile Lys Ser Ala Gly Glu Ser
                180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Arg
210                 215                 220

Val Met Gly Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Asn Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Val Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445
```

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Arg Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510

<210> SEQ ID NO 7
<211> LENGTH: 1686
<212> TYPE: DNA
<213> ORGANISM: Escherichia coli

<400> SEQUENCE: 7

| | |
|---|---|
| atgaagaagg tttggcttaa ccgttatccc gcggacgttc cgacggagat caaccctgac | 60 |
| cgttatcaat ctctggtaga tatgtttgag cagtcggtcg cgcgctacgc cgatcaacct | 120 |
| gcgtttgtga atatggggga ggtaatgacc ttccgcaagc tggaagaacg cagtcgcgcg | 180 |
| tttgccgctt atttgcaaca agggttgggg ctgaagaaag cgatcgcgt tgcgttgatg | 240 |
| atgcctaatt tattgcaata tccggtggcg ctgtttggca ttttgcgtgc cgggatgatc | 300 |
| gtcgtaaacg ttaacccgtt gtataccccg cgtgagcttg agcatcagct aacgatagc | 360 |
| ggcgcatcgg cgattgttat cgtgtctaac tttgctcaca cactggaaaa agtggttgat | 420 |
| aaaaccgccg ttcagcacgt aattctgacc cgtatgggcg atcagctatc tacggcaaaa | 480 |
| ggcacggtag tcaatttcgt tgttaaatac atcaagcgtt tggtgccgaa ataccatctg | 540 |
| ccagatgcca tttcatttcg tagcgcactg cataacggct accggatgca gtacgtcaaa | 600 |
| cccgaactgg tgccggaaga tttagctttt ctgcaataca ccggcggcac cactggtgtg | 660 |
| gcgaaaggcg cgatgctgac tcaccgcaat atgctggcga acctggaaca ggttaacgcg | 720 |
| acctatggtc cgctgttgca tccgggcaaa gagctggtgg tgacggcgct gccgctgtat | 780 |
| cacattttg ccctgaccat taactgcctg ctgtttatcg aactgggtgg gcagaacctg | 840 |
| cttatcacta cccgcgcgga tattccaggg ttggtaaaag agttagcgaa atatccgttt | 900 |
| accgctatca cgggcgttaa caccttgttc aatgcgttgc tgaacaataa agagttccag | 960 |
| cagctggatt tctccagtct gcatctttcc gcaggcggtg ggatgccagt gcagcaagtg | 1020 |
| gtggcagagc gttgggtgaa actgaccgga cagtatctgc tggaaggcta tggccttacc | 1080 |
| gagtgtgcgc cgctggtcag cgttaaccca tatgatattg attatcatag tggtagcatc | 1140 |
| ggtttgccgg tgccgtcgac ggaagccaaa ctggtggatg atgatgataa tgaagtacca | 1200 |
| ccaggtcaac cgggtgagct ttgtgtcaaa ggaccgcagg tgatgctggg ttactggcag | 1260 |
| cgtcccgatg ctaccgatga aatcatcaaa atggctggt tacacaccgg cgacatcgcg | 1320 |
| gtaatggatg aagaaggatt cctgcgcatt gtcgatcgta aaaagacat gattctggtt | 1380 |
| tccggttta acgtctatcc caacgagatt gaagatgtcg tcatgcagca tcctggcgta | 1440 |
| caggaagtcg cggctgttgg cgtaccttcc ggctccagtg gtgaagcggt gaaatcttc | 1500 |
| gtagtgaaaa aagatccatc gcttaccgaa gagtcactgg tgactttttg ccgccgtcag | 1560 |
| ctcacgggat acaaagtacc gaagctggtg gagtttcgtg atgagttacc gaaatctaac | 1620 |
| gtcggaaaaa ttttgcgacg agaattacgt gacgaagcgc gcggcaaagt ggacaataaa | 1680 |
| gcctaa | 1686 |

```
<210> SEQ ID NO 8
<211> LENGTH: 561
<212> TYPE: PRT
<213> ORGANISM: Escherichia coli

<400> SEQUENCE: 8

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
    370                 375                 380
```

```
Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
            405                 410                 415

Gly Tyr Trp Gln Arg Pro Asp Ala Thr Asp Glu Ile Ile Lys Asn Gly
        420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                485                 490                 495

Val Lys Ile Phe Val Val Lys Lys Asp Pro Ser Leu Thr Glu Glu Ser
            500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
    530                 535                 540

Leu Arg Arg Glu Leu Arg Asp Glu Ala Arg Gly Lys Val Asp Asn Lys
545                 550                 555                 560

Ala

<210> SEQ ID NO 9
<211> LENGTH: 981
<212> TYPE: DNA
<213> ORGANISM: Artificial Sequence
<220> FEATURE:
<223> OTHER INFORMATION: Synthetic polynucleotide

<400> SEQUENCE: 9
atgacaatga ttacgccgag ctctgaactc acccttacga aagggaataa aagctggtca      60
tcgacagctg tagctgccgc tttagagtgg aaaccaaaac cgaaattacc tcagcttctt     120
gacgaccact tcggcctgca tggtttagta ttccgcagaa cgtttgccat aagaagctac     180
gaagtaggac cagatcgttc tacctctata cttgctgtga tgaatcatat gcaggaagcc     240
acgttaaatc acgcaaagag cgtcgggatc cttggggacg gattcggcac acattggaa      300 atgagtaagc gggacctgat gtgggttgtt cgtcgtaccc acgtagcggt cgaacggtat     360
ccaacatggg gcgatactgt tgaagtggag tgctggattg gcgcttccgg aaacaacgga     420
atgcgcagag attttctggt gcgggactgt aaaactgggg aaatcttaac gcgctgtacc     480
tccctgtccg ttctgatgaa cacgcgtacc cggagattaa gtacgattcc ggacgaagtc     540
cgtggtgaaa tcggtcccgc ttttattgac aacgtggcgg taaagacga cgagatcaaa      600 aagttgcaga aattgaacga ttccacagca gattacatac agggcggtct tacgccccgt     660
tggaacgact ggatgtgaa tcagcacgta ataaccttaa atatgtggc gtgggtgttc       720 gagaccgttc ccgactctat ttttgaaagt caccacattt ccagctttac gctggagtac     780
agacgcgagt gtacgcgcga ttccgtttta cgttccctca ccacggtgtc tggcggatct     840
tccgaagctg ggttagtgtg tgatcacttg ctgcaacttg aaggcggaag tgaagttctt     900
cgggcccgca cggaatggcg tcccaaactg accgattcct tccgcggaat atcagtaatt     960
ccggccgagc cgcgggtata a                                                981
```

```
<210> SEQ ID NO 10
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 10
```

Met Thr Met Ile Thr Pro Ser Ser Glu Leu Thr Leu Thr Lys Gly Asn
1               5                   10                  15

Lys Ser Trp Ser Ser Thr Ala Val Ala Ala Leu Glu Trp Lys Pro
            20                  25                  30

Lys Pro Lys Leu Pro Gln Leu Leu Asp Asp His Phe Gly Leu His Gly
        35                  40                  45

Leu Val Phe Arg Arg Thr Phe Ala Ile Arg Ser Tyr Glu Val Gly Pro
    50                  55                  60

Asp Arg Ser Thr Ser Ile Leu Ala Val Met Asn His Met Gln Glu Ala
65                  70                  75                  80

Thr Leu Asn His Ala Lys Ser Val Gly Ile Leu Gly Asp Gly Phe Gly
                85                  90                  95

Thr Thr Leu Glu Met Ser Lys Arg Asp Leu Met Trp Val Val Arg Arg
            100                 105                 110

Thr His Val Ala Val Glu Arg Tyr Pro Thr Trp Gly Asp Thr Val Glu
        115                 120                 125

Val Glu Cys Trp Ile Gly Ala Ser Gly Asn Asn Gly Met Arg Arg Asp
130                 135                 140

Phe Leu Val Arg Asp Cys Lys Thr Gly Glu Ile Leu Thr Arg Cys Thr
145                 150                 155                 160

Ser Leu Ser Val Leu Met Asn Thr Arg Thr Arg Arg Leu Ser Thr Ile
                165                 170                 175

Pro Asp Glu Val Arg Gly Glu Ile Gly Pro Ala Phe Ile Asp Asn Val
            180                 185                 190

Ala Val Lys Asp Asp Glu Ile Lys Lys Leu Gln Lys Leu Asn Asp Ser
        195                 200                 205

Thr Ala Asp Tyr Ile Gln Gly Gly Leu Thr Pro Arg Trp Asn Asp Leu
    210                 215                 220

Asp Val Asn Gln His Val Asn Asn Leu Lys Tyr Val Ala Trp Val Phe
225                 230                 235                 240

Glu Thr Val Pro Asp Ser Ile Phe Glu Ser His His Ile Ser Ser Phe
                245                 250                 255

Thr Leu Glu Tyr Arg Arg Glu Cys Thr Arg Asp Ser Val Leu Arg Ser
            260                 265                 270

Leu Thr Thr Val Ser Gly Gly Ser Ser Glu Ala Gly Leu Val Cys Asp
        275                 280                 285

His Leu Leu Gln Leu Glu Gly Gly Ser Glu Val Leu Arg Ala Arg Thr
    290                 295                 300

Glu Trp Arg Pro Lys Leu Thr Asp Ser Phe Arg Gly Ile Ser Val Ile
305                 310                 315                 320

Pro Ala Glu Pro Arg Val
                325

```
<210> SEQ ID NO 11
<211> LENGTH: 718
<212> TYPE: DNA
<213> ORGANISM: Escherichia coli
```

<400> SEQUENCE: 11

```
atggtcatta aggcgcaaag cccggcgggt ttcgcggaag agtacattat tgaaagtatc      60
tggaataacc gcttccctcc cgggactatt tgcccgcag aacgtgaact ttcagaatta     120
attggcgtaa gcgtactacg ttacgtgaag tgttacagcg tctggcacga gatggctggt     180
tgaccattca acatggcaag ccgacgaagg tgaataattt ctgggaaact tccggtttaa     240
atatccttga acactggcg cgactggatc acgaaagtgt gccgcagctt attgataatt     300
tgctgtcggt gcgtaccaat atttccacta tttttattcg caccgcgttt cgtcagcatc     360
ccgataaagc gcaggaagtg ctggctaccg ctaatgaagt ggccgatcac gccgatgcct     420
ttgccgagct ggattacaac atattccgcg gcctggcgtt tgcttccggc aacccgattt     480
acggtctgat tcttaacggg atgaaagggc tgtatacgcg tattggtcgt cactatttcg     540
ccaatccgga agcgcgcagt ctggcgctgg gcttctacca caaactgtcg gcgttgtgca     600
gtgaaggcgc gcacgatcag tgtacgaaac agtgcgtcgc tatgggcatg agagtggcga     660
gatttggcac cggatgcaga aaatctgcc gggtgattta gccattcagg ggcgataa      718
```

<210> SEQ ID NO 12
<211> LENGTH: 238
<212> TYPE: PRT
<213> ORGANISM: Escherichia coli

<400> SEQUENCE: 12

```
Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Asn Asn Phe Trp Glu Thr Ser Gly Leu Asn
65                  70                  75                  80

Ile Leu Glu Thr Leu Ala Arg Leu Asp His Glu Ser Val Pro Gln Leu
                85                  90                  95

Ile Asp Asn Leu Leu Ser Val Arg Thr Asn Ile Ser Thr Ile Phe Ile
            100                 105                 110

Arg Thr Ala Phe Arg Gln His Pro Asp Lys Ala Gln Glu Val Leu Ala
        115                 120                 125

Thr Ala Asn Glu Val Ala Asp His Ala Asp Ala Phe Ala Glu Leu Asp
    130                 135                 140

Tyr Asn Ile Phe Arg Gly Leu Ala Phe Ala Ser Gly Asn Pro Ile Tyr
145                 150                 155                 160

Gly Leu Ile Leu Asn Gly Met Lys Gly Leu Tyr Thr Arg Ile Gly Arg
                165                 170                 175

His Tyr Phe Ala Asn Pro Glu Ala Arg Ser Leu Ala Leu Gly Phe Tyr
            180                 185                 190

His Lys Leu Ser Ala Leu Cys Ser Glu Gly Ala His Asp Gln Val Tyr
        195                 200                 205

Glu Thr Val Arg Arg Tyr Gly His Glu Ser Gly Glu Ile Trp His Arg
    210                 215                 220

Met Gln Lys Asn Leu Pro Gly Asp Leu Ala Ile Gln Gly Arg
225                 230                 235
```

<210> SEQ ID NO 13
<211> LENGTH: 2445
<212> TYPE: DNA
<213> ORGANISM: Escherichia coli

<400> SEQUENCE: 13

| | |
|---|---|
| atgatgattt tgagtattct cgctacggtt gtcctgctcg gcgcgttgtt ctatcaccgc | 60 |
| gtgagcttat ttatcagcag tctgattttg ctcgcctgga cagccgccct cggcgttgct | 120 |
| ggtctgtggt cggcgtgggt actggtgcct ctggccatta tcctcgtgcc atttaacttt | 180 |
| gcgcctatgc gtaagtcgat gatttccgcg ccggtatttc gcggtttccg taaggtgatg | 240 |
| ccgccgatgt cgcgcactga gaaagaagcg attgatgcgg gcaccacctg gtgggagggc | 300 |
| gacttgttcc agggcaagcc ggactggaaa aagctgcata actatccgca gccgcgcctg | 360 |
| accgccgaag agcaagcgtt tctcgacggc ccggtagaag aagcctgccg gatggcgaat | 420 |
| gatttccaga tcacccatga gctggcggat ctgccgccgg agttgtgggc gtaccttaaa | 480 |
| gagcatcgtt tcttcgcgat gatcatcaaa aagagtacgc gcgggctgga gttctcggct | 540 |
| tatgcccagt ctcgcgtgct gcaaaaactc tccggcgtga gcgggatcct ggcgattacc | 600 |
| gtcggcgtgc caaactcatt aggcccgggc gaactgttgc aacattacgg cactgacgag | 660 |
| cagaaagatc actatctgcc gcgtctggcg cgtggtcagg agatcccctg cttgcactg | 720 |
| accagcccgg aagcgggttc cgatgcgggc gcgattccgg acaccgggat tgtctgcatg | 780 |
| ggcgaatggc agggccagca ggtgctgggg atgcgtctga cctggaacaa cgctacatt | 840 |
| acgctggcac cgattgcgac cgtgcttggg ctggcgttta actctccga cccggaaaaa | 900 |
| ttactcggcg gtgcagaaga tttaggcatt acctgtgcgc tgatcccaac caccacgccg | 960 |
| ggcgtggaaa ttggtcgtcg ccacttcccg ctgaacgtac cgttccagaa cggaccgacg | 1020 |
| cgcggtaaag atgtcttcgt gccgatcgat tacatcatcg gcgggccgaa atggccggg | 1080 |
| caaggctggc ggatgctggt ggagtgcctc tcggtaggcc gcggcatcac cctgccttcc | 1140 |
| aactcaaccg gcggcgtgaa atcggtagcg ctggcaaccg gcgcgtatgc tcacattcgc | 1200 |
| cgtcagttca aaatctctat tggtaagatg gaagggattg aagagccgct ggcgcgtatt | 1260 |
| gccggtaatg cctacgtgat ggatgctgcg gcatcgctga ttacctacgg cattatgctc | 1320 |
| ggcgaaaaac ctgccgtgct gtcggctatc gttaagtatc actgtaccca cgcggggcag | 1380 |
| cagtcgatta ttgatgcgat ggatattacc ggcggtaaag cattatgct cgggcaaagc | 1440 |
| aacttcctgg cgcgtgctta ccagggcgca ccgattgcca tcaccgttga agggctaac | 1500 |
| attctgaccc gcagcatgat gatcttcgga caaggagcga ttcgttgcca tccgtacgtg | 1560 |
| ctggaagaga tggaagcggc gaagaacaat gacgtcaacg cgttcgataa actgttgttc | 1620 |
| aaacatatcg gtcacgtcgg tagcaacaaa gttcgcagct ctggctggg cctgacgcgc | 1680 |
| ggtttaacca gcagcacgcc aaccggcgat gccactaaac gctactatca gcacctgaac | 1740 |
| cgcctgagcg ccaacctcgc cctgctttct gatgtctcga tggcagtgct gggcggcagc | 1800 |
| ctgaaacgtc gcgagcgcat ctcggcccgt ctgggggata ttttaagcca gctctacctc | 1860 |
| gcctctgccg tgctgaagcg ttatgacgac gaaggccgta atgaagccga cctgccgctg | 1920 |
| gtgcactggg gcgtacaaga tgcgctgtat caggctgaac aggcgatgga tgatttactg | 1980 |
| caaaacttcc cgaaccgcgt ggttgccggg ctgctgaatg tggtgatctt cccgaccgga | 2040 |
| cgtcattatc tggcacctcc tgacaagctg atcataaag tggcgaagat ttacaagtg | 2100 |
| ccgaacgcca cccgttcccg cattggtcgc ggtcagtacc tgacgccgag cgagcataat | 2160 |

```
ccggttggct tgctggaaga ggcgctggtg gatgtgattg ccgccgaccc aattcatcag   2220
cggatctgta aagagctggg taaaaacctg ccgtttaccc gtctggatga actggcgcac   2280
aacgcgctgg tgaagggggct gattgataaa gatgaagccg ctattctggt gaaagctgaa   2340
gaaagccgtc tgcgcagtat taacgttgat gactttgatc cggaagagct ggcgacgaag   2400
ccggtaaagt tgccggagaa agtgcggaaa gttgaagccg cgtaa                    2445
```

<210> SEQ ID NO 14
<211> LENGTH: 814
<212> TYPE: PRT
<213> ORGANISM: Escherichia coli

<400> SEQUENCE: 14

```
Met Met Ile Leu Ser Ile Leu Ala Thr Val Val Leu Gly Ala Leu
1               5                   10                  15

Phe Tyr His Arg Val Ser Leu Phe Ile Ser Ser Leu Ile Leu Leu Ala
                20                  25                  30

Trp Thr Ala Ala Leu Gly Val Ala Gly Leu Trp Ser Ala Trp Val Leu
            35                  40                  45

Val Pro Leu Ala Ile Ile Leu Val Pro Phe Asn Phe Ala Pro Met Arg
    50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asp Ala Gly Thr Thr
                85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Gln Ala Phe Leu
        115                 120                 125

Asp Gly Pro Val Glu Glu Ala Cys Arg Met Ala Asn Asp Phe Gln Ile
    130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
    210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Val Leu Gly Met Arg
            260                 265                 270

Leu Thr Trp Asn Lys Arg Tyr Ile Thr Leu Ala Pro Ile Ala Thr Val
        275                 280                 285

Leu Gly Leu Ala Phe Lys Leu Ser Asp Pro Glu Lys Leu Leu Gly Gly
    290                 295                 300

Ala Glu Asp Leu Gly Ile Thr Cys Ala Leu Ile Pro Thr Thr Thr Pro
305                 310                 315                 320
```

```
Gly Val Glu Ile Gly Arg Arg His Phe Pro Leu Asn Val Pro Phe Gln
            325                 330                 335

Asn Gly Pro Thr Arg Gly Lys Asp Val Phe Val Pro Ile Asp Tyr Ile
            340                 345                 350

Ile Gly Gly Pro Lys Met Ala Gly Gln Gly Trp Arg Met Leu Val Glu
            355                 360                 365

Cys Leu Ser Val Gly Arg Gly Ile Thr Leu Pro Ser Asn Ser Thr Gly
            370                 375             380

Gly Val Lys Ser Val Ala Leu Ala Thr Gly Ala Tyr Ala His Ile Arg
385                     390                 395                 400

Arg Gln Phe Lys Ile Ser Ile Gly Lys Met Glu Gly Ile Glu Pro
                405                 410                 415

Leu Ala Arg Ile Ala Gly Asn Ala Tyr Val Met Asp Ala Ala Ala Ser
            420                 425             430

Leu Ile Thr Tyr Gly Ile Met Leu Gly Glu Lys Pro Ala Val Leu Ser
            435                 440                 445

Ala Ile Val Lys Tyr His Cys Thr His Arg Gly Gln Gln Ser Ile Ile
        450                 455                 460

Asp Ala Met Asp Ile Thr Gly Lys Gly Ile Met Leu Gly Gln Ser
465                 470                 475                 480

Asn Phe Leu Ala Arg Ala Tyr Gln Gly Ala Pro Ile Ala Ile Thr Val
                485                 490                 495

Glu Gly Ala Asn Ile Leu Thr Arg Ser Met Met Ile Phe Gly Gln Gly
            500                 505                 510

Ala Ile Arg Cys His Pro Tyr Val Leu Glu Glu Met Glu Ala Ala Lys
            515                 520                 525

Asn Asn Asp Val Asn Ala Phe Asp Lys Leu Leu Phe Lys His Ile Gly
        530                 535                 540

His Val Gly Ser Asn Lys Val Arg Ser Phe Trp Leu Gly Leu Thr Arg
545                 550                 555                 560

Gly Leu Thr Ser Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
            580                 585                 590

Ser Met Ala Val Leu Gly Gly Ser Leu Lys Arg Arg Glu Arg Ile Ser
            595                 600                 605

Ala Arg Leu Gly Asp Ile Leu Ser Gln Leu Tyr Leu Ala Ser Ala Val
            610                 615                 620

Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
                645                 650                 655

Asp Asp Leu Leu Gln Asn Phe Pro Asn Arg Val Val Ala Gly Leu Leu
            660                 665                 670

Asn Val Val Ile Phe Pro Thr Gly Arg His Tyr Leu Ala Pro Ser Asp
            675                 680                 685

Lys Leu Asp His Lys Val Ala Lys Ile Leu Gln Val Pro Asn Ala Thr
            690                 695             700

Arg Ser Arg Ile Gly Arg Gly Gln Tyr Leu Thr Pro Ser Glu His Asn
705                 710                 715                 720

Pro Val Gly Leu Leu Glu Glu Ala Leu Val Asp Val Ile Ala Ala Asp
                725                 730                 735

Pro Ile His Gln Arg Ile Cys Lys Glu Leu Gly Lys Asn Leu Pro Phe
```

|  | 740 |  |  | 745 |  |  | 750 |  |  |
|---|---|---|---|---|---|---|---|---|---|
| Thr | Arg | Leu | Asp | Glu | Leu | Ala | His | Asn | Ala | Leu | Val | Lys | Gly | Leu | Ile |
|  |  | 755 |  |  |  |  | 760 |  |  |  |  | 765 |

Asp Lys Asp Glu Ala Ala Ile Leu Val Lys Ala Glu Glu Ser Arg Leu
770     775     780

Arg Ser Ile Asn Val Asp Asp Phe Asp Pro Glu Leu Ala Thr Lys
785     790     795     800

Pro Val Lys Leu Pro Glu Lys Val Arg Lys Val Glu Ala Ala
     805     810

<210> SEQ ID NO 15
<211> LENGTH: 5905
<212> TYPE: DNA
<213> ORGANISM: Artificial Sequence
<220> FEATURE:
<223> OTHER INFORMATION: Synthetic polynucleotide

<400> SEQUENCE: 15

| ggcatccgct | tacagacaag | ctgtgaccgt | ctccgggagc | tgcatgtgtc | agaggttttc | 60 |
| accgtcatca | ccgaaacgcg | cgaggcagca | gatcaattcg | cgcgcgaagg | cgaagcggca | 120 |
| tgcatttacg | ttgacaccat | cgaatggtgc | aaaacctttc | gcggtatggc | atgatagcgc | 180 |
| ccggaagaga | gtcaattcag | ggtggtgaat | gtgaaaccag | taacgttata | cgatgtcgca | 240 |
| gagtatgccg | gtgtctctta | tcagaccgtt | tcccgcgtgg | tgaaccaggc | cagccacgtt | 300 |
| tctgcgaaaa | cgcgggaaaa | agtggaagcg | gcgatggcgg | agctgaatta | cattcccaac | 360 |
| cgcgtggcac | aacaactggc | gggcaaacag | tcgttgctga | ttggcgttgc | cacctccagt | 420 |
| ctggccctgc | acgcgccgtc | gcaaattgtc | gcggcgatta | aatctcgcgc | cgatcaactg | 480 |
| ggtgccagcg | tggtggtgtc | gatggtagaa | cgaagcggcg | tcgaagcctg | taaagcggcg | 540 |
| gtgcacaatc | ttctcgcgca | acgcgtcagt | gggctgatca | ttaactatcc | gctggatgac | 600 |
| caggatgcca | ttgctgtgga | agctgcctgc | actaatgttc | cggcgttatt | cttgatgtc | 660 |
| tctgaccaga | cacccatcaa | cagtattatt | ttctcccatg | aagacggtac | gcgactgggc | 720 |
| gtggagcatc | tggtcgcatt | gggtcaccag | caaatcgcgc | tgttagcggg | cccattaagt | 780 |
| tctgtctcgg | cgcgtctgcg | tctggctggc | tggcataaat | atctcactcg | caatcaaatt | 840 |
| cagccgatag | cggaacggga | aggcgactgg | agtgccatgt | ccggttttca | acaaaccatg | 900 |
| caaatgctga | atgagggcat | cgttcccact | gcgatgctgg | ttgccaacga | tcagatggcg | 960 |
| ctgggcgcaa | tgcgcgccat | taccgagtcc | gggctgcgcg | ttggtgcgga | tatctcggta | 1020 |
| gtgggatacg | acgataccga | agacagctca | tgttatatcc | cgccgttaac | caccatcaaa | 1080 |
| caggattttc | gcctgctggg | gcaaaccagc | gtggaccgct | tgctgcaact | ctctcagggc | 1140 |
| caggcggtga | agggcaatca | gctgttgccc | gtctcactgg | tgaaaagaaa | aaccaccctg | 1200 |
| gcgcccaata | cgcaaaccgc | ctctccccgc | gcgttggccg | attcattaat | gcagctggca | 1260 |
| cgacaggttt | cccgactgga | aagcgggcag | tgagcgcaac | gcaattaatg | taagttagcg | 1320 |
| cgaattgatc | tggtttgaca | gcttatcatc | gactgcacgg | tgcaccaatg | cttctggcgt | 1380 |
| caggcagcca | tcggaagctg | tggtatggct | gtgcaggtcg | taaatcactg | cataattcgt | 1440 |
| gtcgctcaag | gcgcactccc | gttctggata | atgttttttg | cgccgacatc | ataacggttc | 1500 |
| tggcaaatat | tctgaaatga | gctgttgaca | attaatcatc | cggctcgtat | aatgtgtgga | 1560 |
| attgtgagcg | gataacaatt | tcacacagga | aacagcgccg | ctgagaaaaa | gcgaagcggc | 1620 |
| actgctcttt | aacaatttat | cagacaatct | gtgtgggcac | tcgaccggaa | ttatcgatta | 1680 |

```
actttattat taaaaattaa agaggtatat attaatgtat cgattaaata aggaggaata    1740
aaccatggat ccgagctcga gatctgcagc tggtaccata tgggaattcg aagctttcta    1800
gaacaaaaac tcatctcaga agaggatctg aatagcgccg tcgaccatca tcatcatcat    1860
cattgagttt aaacggtctc cagcttggct gttttggcgg atgagagaag attttcagcc    1920
tgatacagat taaatcagaa cgcagaagcg gtctgataaa acagaatttg cctggcggca    1980
gtagcgcggt ggtcccacct gaccccatgc cgaactcaga agtgaaacgc cgtagcgccg    2040
atggtagtgt ggggtctccc catgcgagag tagggaactg ccaggcatca aataaaacga    2100
aaggctcagt cgaaagactg ggcctttcgt tttatctgtt gtttgtcggt gaacgctctc    2160 ctgagcgcc tgatgcggta ttttctcctt acgcatctgt gcggtatttc acaccgcata    2220
tggtgcactc tcagtacaat ctgctctgat gccgcatagt taagccagcc ccgacacccg    2280
ccaacacccg ctgacgagct tagtaaagcc ctcgctagat tttaatgcgg atgttgcgat    2340
tacttcgcca actattgcga taacaagaaa aagccagcct ttcatgatat atctcccaat    2400
ttgtgtaggg cttattatgc acgcttaaaa ataataaaag cagacttgac ctgatagttt    2460
ggctgtgagc aattatgtgc ttagtgcatc taacgcttga gttaagccgc gccgcgaagc    2520
ggcgtcggct tgaacgaatt gttagacatt atttgccgac taccttggtg atctcgcctt    2580
tcacgtagtg gacaaattct tccaactgat ctgcgcgcga ggccaagcga tcttcttctt    2640
gtccaagata agcctgtcta gcttcaagta tgacgggctg atactgggcc ggcaggcgct    2700
ccattgccca gtcggcagcg acatccttcg gcgcgatttt gccggttact gcgctgtacc    2760
aaatgcggga caacgtaagc actacatttc gctcatcgcc agcccagtcg ggcggcgagt    2820
tccatagcgt taaggtttca tttagcgcct caaatagatc ctgttcagga accggatcaa    2880
agagttcctc cgccgctgga cctaccaagg caacgctatg ttctcttgct tttgtcagca    2940
agatagccag atcaatgtcg atcgtggctg gctcgaagat acctgcaaga atgtcattgc    3000
gctgccattc tccaaattgc agttcgcgct tagctggata acgccacgga atgatgtcgt    3060
cgtgcacaac aatggtgact tctacagcgc ggagaatctc gctctctcca ggggaagccg    3120
aagtttccaa aaggtcgttg atcaaagctc gccgcgttgt ttcatcaagc cttacggtca    3180
ccgtaaccag caaatcaata tcactgtgtg gcttcaggcc gccatccact gcggagccgt    3240
acaaatgtac ggccagcaac gtcggttcga gatggcgctc gatgacgcca actacctctg    3300
atagttgagt cgatacttcg gcgatcaccg cttccctcat gatgtttaac tttgttttag    3360
ggcgactgcc ctgctgcgta acatcgttgc tgctccataa catcaaacat cgacccacgg    3420
cgtaacgcgc ttgctgcttg gatgcccgag gcatagactg taccccaaaa aaacagtcat    3480
aacaagccat gaaaaccgcc actgcgccgt taccaccgct gcgttcggtc aaggttctgg    3540
accagttgcg tgagcgcata cgctacttgc attacagctt acgaaccgaa caggcttatg    3600
tccactgggt tcgtgccttc atccgtttcc acggtgtgcg tcaccggca accttgggca    3660 gcagcgaagt cgaggcattt ctgtcctggc tggcgaacga gcgcaaggtt cggtctcca    3720 cgcatcgtca ggcattggcg gccttgctgt tcttctacgg caaggtgctg tgcacggatc    3780
tgccctggct tcaggagatc ggaagacctc ggccgtcgcg gcgcttgccg gtggtgctga    3840
ccccggatga agtggttcgc atcctcggtt ttctggaagg cgagcatcgt ttgttcgccc    3900
agcttctgta tggaacgggc atgcggatca gtgagggttt gcaactgcgg gtcaaggatc    3960
tggatttcga tcacggcacg atcatcgtgc gggagggcaa gggctccaag gatcgggcct    4020
```

| | |
|---|---|
| tgatgttacc cgagagcttg gcacccagcc tgcgcgagca ggggaattaa ttcccacggg | 4080 |
| ttttgctgcc cgcaaacggg ctgttctggt gttgctagtt tgttatcaga atcgcagatc | 4140 |
| cggcttcagc cggtttgccg gctgaaagcg ctatttcttc cagaattgcc atgatttttt | 4200 |
| ccccacggga ggcgtcactg gctcccgtgt tgtcggcagc tttgattcga taagcagcat | 4260 |
| cgcctgtttc aggctgtcta tgtgtgactg ttgagctgta acaagttgtc tcaggtgttc | 4320 |
| aatttcatgt tctagttgct ttgttttact ggtttcacct gttctattag gtgttacatg | 4380 |
| ctgttcatct gttacattgt cgatctgttc atggtgaaca gctttgaatg caccaaaaac | 4440 |
| tcgtaaaagc tctgatgtat ctatctttt tacaccgttt tcatctgtgc atatggacag | 4500 |
| ttttcccttt gatatgtaac ggtgaacagt tgttctactt ttgtttgtta gtcttgatgc | 4560 |
| ttcactgata gatacaagag ccataagaac ctcagatcct tccgtattta gccagtatgt | 4620 |
| tctctagtgt ggttcgttgt ttttgcgtga gccatgagaa cgaaccattg agatcatact | 4680 |
| tactttgcat gtcactcaaa aattttgcct caaaactggt gagctgaatt tttgcagtta | 4740 |
| aagcatcgtg tagtgttttt cttagtccgt tatgtaggta ggaatctgat gtaatggttg | 4800 |
| ttggtatttt gtcaccattc attttatct ggttgttctc aagttcggtt acgagatcca | 4860 |
| tttgtctatc tagttcaact tggaaaatca acgtatcagt cgggcggcct cgcttatcaa | 4920 |
| ccaccaattt catattgctg taagtgttta aatctttact tattggtttc aaaacccatt | 4980 |
| ggttaagcct tttaaactca tggtagttat tttcaagcat taacatgaac ttaaattcat | 5040 |
| caaggctaat ctctatattt gccttgtgag ttttcttttg tgttagttct tttaataacc | 5100 |
| actcataaat cctcatagag tatttgtttt caaaagactt aacatgttcc agattatatt | 5160 |
| ttatgaattt ttttaactgg aaaagataag gcaatatctc ttcactaaaa actaattcta | 5220 |
| attttttcgct tgagaacttg gcatagtttg tccactggaa aatctcaaag cctttaacca | 5280 |
| aaggattcct gatttccaca gttctcgtca tcagctctct ggttgcttta gctaatacac | 5340 |
| cataagcatt ttccctactg atgttcatca tctgagcgta ttggttataa gtgaacgata | 5400 |
| ccgtccgttc tttccttgta gggttttcaa tcgtggggtt gagtagtgcc acacagcata | 5460 |
| aaattagctt ggtttcatgc tccgttaagt catagcgact aatcgctagt tcatttgctt | 5520 |
| tgaaaacaac taattcagac atacatctca attggtctag gtgattttaa tcactatacc | 5580 |
| aattgagatg ggctagtcaa tgataattac tagtcctttt cctttgagtt gtgggtatct | 5640 |
| gtaaattctg ctagacccttt gctggaaaac ttgtaaattc tgctagaccc tctgtaaatt | 5700 |
| ccgctagacc tttgtgtgtt ttttttgttt atattcaagt ggttataatt tatagaataa | 5760 |
| agaaagaata aaaaagata aaagaatag atcccagccc tgtgtataac tcactacttt | 5820 |
| agtcagttcc gcagtattac aaaaggatgt cgcaaacgct gtttgctcct ctacaaaaca | 5880 |
| gaccttaaaa ccctaaaggc ttaag | 5905 |

<210> SEQ ID NO 16
<211> LENGTH: 4032
<212> TYPE: DNA
<213> ORGANISM: Artificial Sequence
<220> FEATURE:
<223> OTHER INFORMATION: Synthetic polynucleotide

<400> SEQUENCE: 16

| | |
|---|---|
| tcgagttaat taaggcagtg agcgcaacgc aattaatgtg agttagctca ctcattaggc | 60 |
| accccaggct ttacacttta tgcttccggc tcgtatgttg tgtggaattg tgagcggata | 120 |
| acaatttcac acaggaaaca gctatgacca tgattacgga ttcactggcc gtcgttttac | 180 |

```
aatctagagg ccagcctggc cataaggaga tatacatatg agtattcaac atttccgtgt    240
cgcccttatt ccctttttg cggcattttg ccttcctgtt tttgctcacc cagaaacgct     300
ggtgaaagta aaagatgctg aagatcagtt gggtgcacga gtgggttaca tcgaactgga    360
tctcaacagc ggtaagatcc ttgagagttt tcgccccgaa gagcgttttc caatgatgag    420
cacttttaaa gttctgctat gtggcgcggt attatcccgt gttgacgccg gcaagagca     480 actcggtcgc cgcatacact attctcagaa tgacttggtt gagtactcac cagtcacaga    540
aaagcatctt acggatggca tgacagtaag agaattatgc agtgctgcca taaccatgag    600
tgataacact gcggccaact tacttctgac aacgatcgga ggaccgaagg agctaaccgt    660
ttttttgcac accatggggg atcatgtaac tcgccttgat cgttgggaac cggagctgaa    720
tgaagccata ccaaacgacg agcgtgacac cacgatgcct acagcaatgg caacaacgtt    780
gcgcaaacta ttaactggcg aactacttac tctagcttcc cggcaacaat aatagactg     840 gatggaggcg gataaagttg caggaccact tctgcgctcg gcccttccgg ctggctggtt    900
tattgctgat aaatctggag ccggtgagcg tgggtctcgc ggtatcattg cagcactggg    960
gccagatggt aagccctccc gtatcgtagt tatctacacg acggggagtc aggcaactat    1020
ggatgaacga aatagacaga tcgctgagat aggtgcctca ctgattaagc attggggcca    1080
aactggccac catcaccatc accattaggg aagagcagat gggcaagctt gacctgtgaa    1140
gtgaaaaatg gcgcacattg tgcgacattt ttttttgaat tctacgtaaa aagcagccga    1200
tacatcggct gctttttttt tgatagaggt tccaacttgt ggtataatga ataagatca     1260 ctccggagcg tatttttga gttatcgaga ttttcaggag ctaaggaggc taaaatggag     1320
aaaaaaatca ctggatatac caccgttgat atatcccaat ggcatcgtaa agaacatttt    1380
gaggcatttc agtcagttgc tcaatgtacc tataaccaga ccgttcagct ggatattacg    1440 gccttttaa agaccgtaaa gaaaaataag cacaagtttt atccggcctt tattcacatt     1500
cttgcccgcc tgatgaatgc tcatccggag ttccgtatgg caatgaaaga cggtgagctg    1560
gtgatatggg atagtgttca cccttgttac accgttttcc atgagcaaac tgaaacgttt    1620
tcatcgctct ggagtgaata ccacgacgat ttccggcagt ttctacacat atattcgcaa    1680
gatgtggcgt gttacggtga aaacctggcc tatttcccta aagggtttat tgagaatatg    1740
tttttcgtct cagccaatcc ctgggtgagt ttcaccagtt tgatttaaa cgtggccaat     1800 atggacaact tcttcgcccc cgttttcacc atgggcaaat attatacgca aggcgacaag    1860
gtgctgatgc cgctggcgat tcaggttcat catgccgtct gtgatggctt ccatgtcggc    1920
agaatgctta atgaattaca acagtactgc gatgagtggc agggcggggc gtaactgcag    1980
gagctcaaac agcagcctgt attcaggctg cttttttcgt tttggtctgc gcgtaatctc    2040
ttgctctgaa acgaaaaaa ccgccttgca gggcggtttt tcgaaggttc tctgagctac     2100
caactctttg aaccgaggta actggcttgg aggagcgcag tcaccaaaac ttgtcctttc    2160
agtttagcct taaccggcgc atgacttcaa gactaactcc tctaaatcaa ttaccagtgg    2220
ctgctgccag tggtgctttt gcatgtcttt ccggggttgga ctcaagacga tagttaccgg    2280
ataaggcgca gcggtcggac tgaacggggg gttcgtgcat acagtccagc ttggagcgaa    2340
ctgcctaccc ggaactgagt gtcaggcgtg gaatgagaca aacgcggcca taacagcgga    2400
atgacaccgg taaccgaaa ggcaggaaca ggagagcgca cgagggagcc gccagggga     2460 aacgcctggt atctttatag tcctgtcggg tttcgccacc actgatttga gcgtcagatt    2520
```

```
tcgtgatgct tgtcaggggg gcggagccta tggaaaaacg ctttgccgc ggccctctca    2580 cttccctgtt aagtatcttc ctggcatctt ccaggaaatc tccgcccgt tcgtaagcca    2640 tttccgctcg ccgcagtcga acgaccgagc gtagcgagtc agtgagcgag gaagcggaat   2700
atatcctgta tcacatattc tgctgacgca ccggtgcagc cttttttctc ctgccacatg   2760
aagcacttca ctgacaccct catcagtgaa ccaccgctgg tagcggtggt ttttttaggc   2820
ctatggcctt ttttttttgt gggaaacctt tcgcggtatg gtattaaagc gcccggaaga   2880
gagtcaatta agggtggtga atgtgaaacc agtaacgtta tacgatgtcg cagagtatgc   2940
cggtgtctct tatcagaccg tttcccgcgt ggtgaaccag gccagccacg tttctgcgaa   3000
aacgcgggaa aaagtggaag cggcgatggc ggagctgaat tacattccca accgcgtggc   3060
acaacaactg gcgggcaaac agtcgttgct gattggcgtt gccacctcca gtctggccct   3120
gcacgcgccg tcgcaaattg tcgcggcgat taaatctcgc gccgatcaac tgggtgccag   3180
cgtggtggtg tcgatggtag aacgaagcgg cgtcgaagcc tgtaaagcgg cggtgcacaa   3240
tcttctcgcg caacgcgtca gtgggctgat cattaactat ccgctggatg accaggatgc   3300
cattgctgtg gaagctgcct gcactaatgt tccggcgtta tttcttgatg tctctgacca   3360
gacacccatc aacagtatta ttttctccca tgaagacggt acgcgactgg gcgtggagca   3420
tctggtcgca ttgggtcacc agcaaatcgc gctgttagcg ggcccattaa gttctgtctc   3480
ggcgcgtctg cgtctggctg ctggcataa atatctcact cgcaatcaaa ttcagccgat   3540
agcggaacgg gaaggcgact ggagtgccat gtccggtttt caacaaacca tgcaaatgct   3600
gaatgagggc atcgttccca ctgcgatgct ggttgccaac gatcagatgg cgctgggcgc   3660
aatgcgcgcc attaccgagt ccgggctgcg cgttggtgcg gacatctcgg tagtgggata   3720
cgacgatacc gaagacagct catgttatat cccgccgtta accaccatca acaggatttt   3780
tcgcctgctg ggcaaaacca gcgtggaccg cttgctgcaa ctctctcagg ccaggcggt    3840 gaagggcaat cagctgttgc ccgtctcact ggtgaaaaga aaaccaccc tggcgcccaa    3900 tacgcaaacc gcctctcccc gcgcgttggc cgattcatta atgcagctgg cacgacaggt   3960
ttcccgactg gaaagcgggc agtgagcggt acccgataaa agcggcttcc tgacaggagg   4020
ccgttttgtt tc                                                       4032
```

<210> SEQ ID NO 17
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 17
gaccttaaaa ccctaaaggc ttaagggcat ccgcttacag aca                     43

<210> SEQ ID NO 18
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 18
cagccacttg cgagaggact ccgcggacta cgccataaaa gagg                    44

<210> SEQ ID NO 19
<211> LENGTH: 682

<212> TYPE: DNA
<213> ORGANISM: Artificial Sequence
<220> FEATURE:
<223> OTHER INFORMATION: Synthetic polynucleotide

<400> SEQUENCE: 19

| | | | | | |
|---|---|---|---|---|---|
| gatatctcgg | tagtgggata | cgacgatacc | gaagacagct | catgttatat | cccgccgtta | 60 |
| accaccatca | aacaggattt | tcgcctgctg | gggcaaacca | gcgtggaccg | cttgctgcaa | 120 |
| ctctctcagg | gccaggcggt | gaagggcaat | cagctgttgc | ccgtctcact | ggtgaaaaga | 180 |
| aaaaccaccc | tggcgcccaa | tacgcaaacc | gcctctcccc | gcgcgttggc | cgattcatta | 240 |
| atgcagctgg | cacgacaggt | ttcccgactg | gaaagcgggc | agtaataatt | taaattggtt | 300 |
| tgacagctta | tcatcgactg | cacggtgcac | caatgcttct | ggcgtcaggc | agccatcgga | 360 |
| agctgtggta | tggctgtgca | ggtcgtaaat | cactgcataa | ttcgtgtcgc | tcaaggcgca | 420 |
| ctcccgttct | ggataatgtt | ttttgcgccg | acataattgt | gagcgctcac | aatttctgaa | 480 |
| atgagctgtt | gacaattaat | catccggctc | gtataatgtg | tggaattgtg | agcggataac | 540 |
| aatttcacac | aggaaacagc | gccgctgaga | aaaagcgaag | cggcactgct | ctttaacaat | 600 |
| ttatcagaca | atctgtgtgg | gcactcgacc | ggaattatcg | attaacttta | ttattaaaaa | 660 |
| ttaaaggagg | aataaaccat | gg | | | | 682 |

<210> SEQ ID NO 20
<211> LENGTH: 73
<212> TYPE: DNA
<213> ORGANISM: Artificial Sequence
<220> FEATURE:
<223> OTHER INFORMATION: Synthetic polynucleotide

<400> SEQUENCE: 20

| | | | | | |
|---|---|---|---|---|---|
| acaatctaga | ggccagcctg | gccataagga | gatatacata | tgaagaaggt | ttggcttaac | 60 |
| cgttatcccg | cgg | | | | | 73 |

<210> SEQ ID NO 21
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 21

| | | | | | |
|---|---|---|---|---|---|
| gcttcgcgcg | ccgtttcacc | tgttatttcg | gattactccg | gtttgaccgg | tggtagtggt | 60 |
| acta | | | | | | 64 |

<210> SEQ ID NO 22
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 22
taaaccatgg cgactcaaca acagaaca    28

<210> SEQ ID NO 23
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 23
ctatgtcgac ttaggcggtt ttatcgtcag tatca                          35

<210> SEQ ID NO 24
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 24
tgatactgac gataaaaccg cctaagtcga caaggaggaa taaaccatga caatgattac    60
gccgagct                                                            68

<210> SEQ ID NO 25
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 25
ttatacccgc ggctcggccg g                                         21

<210> SEQ ID NO 26
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 26
ccggccgagc cgcgggtata aaaggagata tacatatgaa gaaggtttgg cttaaccg     58

<210> SEQ ID NO 27
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 27
ccgagtaagt tctagatctt cattaggctt tattgtccac tttgc               45

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
tgtggaattg tgagcggata                                           20

<210> SEQ ID NO 29
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 29
cgcttctgcg ttctgattt                                            19

```
<210> SEQ ID NO 30
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 30
tgatactgac gataaaaccg cctaagtcga caaggaggaa taaaccatga ccttagagtg     60
gaaaccaaaa c                                                         71

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 31
ttatacccgc ggctcggccg g                                              21

<210> SEQ ID NO 32
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 32
ccggccgagc cgcgggtata aaaggagata tacatatgaa gaaggtttgg cttaaccg      58

<210> SEQ ID NO 33
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 33
ccgagtaagt tctagatctt cattaggctt tattgtccac tttgc                    45

<210> SEQ ID NO 34
<211> LENGTH: 906
<212> TYPE: DNA
<213> ORGANISM: Artificial Sequence
<220> FEATURE:
<223> OTHER INFORMATION: Synthetic polynucleotide

<400> SEQUENCE: 34
atgaccttag agtggaaacc aaaaccgaaa ttacctcagc ttcttgacga ccacttcggc     60
ctgcatggtt tagtattccg cagaacgttt gccataagaa gctacgaagt aggaccagat    120
cgttctacct ctatacttgc tgtgatgaat catatgcagg aagccacgtt aaatcacgca    180
aagagcgtcg ggatccttgg ggacggattc ggcaccacat tggaaatgag taagcggggac   240 ctgatgtggg ttgttcgtcg tacccacgta gcggtcgaac ggtatccaac atggggcgat    300
actgttgaag tggagtgctg gattggcgct tccggaaaca acggaatgcg cagagatttt    360
ctggtgcggg actgtaaaac tggggaaatc ttaacgcgct gtacctccct gtccgttctg    420
atgaacacgc gtacccggag attaagtacg attccggacg aagtccgtgg tgaaatcggt    480
cccgctttta ttgacaacgt ggcggtaaaa gacgacgaga tcaaaaagtt gcagaaattg    540
aacgattcca cagcagatta catacagggc ggtcttacgc cccgttggaa cgacttggat    600
```

```
gtgaatcagc acgtaaataa ccttaaatat gtggcgtggg tgttcgagac cgttcccgac    660 tctattttg aaagtcacca catttccagc tttacgctgg agtacagacg cgagtgtacg     720
cgcgattccg ttttacgttc cctcaccacg gtgtctggcg gatcttccga agctgggtta    780
gtgtgtgatc acttgctgca acttgaaggc ggaagtgaag ttcttcgggc ccgcacggaa    840
tggcgtccca aactgaccga ttccttccgc ggaatatcag taattccggc cgagccgcgg    900
gtataa                                                               906
```

```
<210> SEQ ID NO 35
<211> LENGTH: 301
<212> TYPE: PRT
<213> ORGANISM: Umbellularia california

<400> SEQUENCE: 35

Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
                20                  25                  30

Arg Ser Tyr Glu Val Gly Pro Asp Arg Ser Thr Ser Ile Leu Ala Val
            35                  40                  45

Met Asn His Met Gln Glu Ala Thr Leu Asn His Ala Lys Ser Val Gly
        50                  55                  60

Ile Leu Gly Asp Gly Phe Gly Thr Thr Leu Glu Met Ser Lys Arg Asp
65                  70                  75                  80

Leu Met Trp Val Val Arg Arg Thr His Val Ala Val Glu Arg Tyr Pro
                85                  90                  95

Thr Trp Gly Asp Thr Val Glu Val Glu Cys Trp Ile Gly Ala Ser Gly
            100                 105                 110

Asn Asn Gly Met Arg Arg Asp Phe Leu Val Arg Asp Cys Lys Thr Gly
        115                 120                 125

Glu Ile Leu Thr Arg Cys Thr Ser Leu Ser Val Leu Met Asn Thr Arg
130                 135                 140

Thr Arg Arg Leu Ser Thr Ile Pro Asp Glu Val Arg Gly Glu Ile Gly
145                 150                 155                 160

Pro Ala Phe Ile Asp Asn Val Ala Val Lys Asp Asp Glu Ile Lys Lys
                165                 170                 175

Leu Gln Lys Leu Asn Asp Ser Thr Ala Asp Tyr Ile Gln Gly Gly Leu
            180                 185                 190

Thr Pro Arg Trp Asn Asp Leu Asp Val Asn Gln His Val Asn Asn Leu
        195                 200                 205

Lys Tyr Val Ala Trp Val Phe Glu Thr Val Pro Asp Ser Ile Phe Glu
210                 215                 220

Ser His His Ile Ser Ser Phe Thr Leu Glu Tyr Arg Arg Glu Cys Thr
225                 230                 235                 240

Arg Asp Ser Val Leu Arg Ser Leu Thr Thr Val Ser Gly Gly Ser Ser
                245                 250                 255

Glu Ala Gly Leu Val Cys Asp His Leu Leu Gln Leu Glu Gly Gly Ser
            260                 265                 270

Glu Val Leu Arg Ala Arg Thr Glu Trp Arg Pro Lys Leu Thr Asp Ser
        275                 280                 285

Phe Arg Gly Ile Ser Val Ile Pro Ala Glu Pro Arg Val
    290                 295                 300

<210> SEQ ID NO 36
```

<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 36

```
atggcgactc aacaacagaa caacggtgca tctgcatccg gcgtcttgga aattcttcgt      60
ggaaagcacg ttcttatcac aggtactacc ggattttttgg gcaaagtggt tctggaaaag    120
ttgattcgta ctgttccgga tattggaggt attcatctgc tgattcgtgg caataaacgt    180
catccagccg ctcgcgaacg tttcctgaac gaaattgcgt cctcctccgt cttcgaacgt    240
ttgcgtcacg atgataatga agccttcgag accttcttgg aagaacgtgt tcactgtatt    300
accggtgaga ttactgaatc ccgttttggt ttgacacctg agcgttttcg tgctttggcc    360
ggtcaggttg acgcttttat tcatagcgct gcaagcgtga actttcgtga gcaattggat    420
aaagccctga aaatcaacac cttgtgtctt gaaaatgttg ctgctcttgc agaattgaac    480
tccgctatgg cggtcattca ggtttccact tgttacgtta acggtaaaac ctccggtcaa    540
attaccgaat ccgtcattaa atcggctggc gaatccattc ccgttccac tgacggttac      600
tacgagatcg aagaattggt ccatctgttg caagacaaga tttccgatgt aaagctcgt     660
tactccggcc gtgttatggg gaaaaaattg gttgatttgg gtattcgtga ggccaataat    720
tacggatggt ccgacaccta cacattcacc aaatggttgg gtgaacaact gctgatgaag    780
gccttgtctg gtcgttcttt gactattgtg cgtccctcta ttattgagtc cgctttggaa    840
gaaccttccc ctggttggat cgaaggcgtt aaagttgccg atgccattat cttggcttat    900
gcccgtgaaa aagttagcct gttccctgga aaacgttccg gcattattga tgttattcct    960
gtcgatttgg ttgcgaactc catcatcttg tctctggctg aggcgttgtc tggttctggt   1020
caacgtcgta tttatcaatg ttgcagcggt ggttctaatc caatctccct gggtaagttc   1080
attgattatt tgaacgccga ggctaagacc aactatgctg cctacgatca actgttttat   1140
cgtcgtccta ctaaacctt cgtcgccgtg aaccgtaaat tgtttgacgt tgttgttggt    1200
gtcatgcgtg ttgtccttc tattgcccgc aaagctatgc gtttggctgg tgtaaatcgt   1260
gagttgaaag tgcttaagaa ccttgatacg acccgtaaac ttgcaaccat ttttggcttc   1320
tatactgctc ccgactatat cttccgtaac gatagcttga tggccctggc tcagcgtatg   1380
ggtgaattgg atcgtgttct tttcccagtt gatgctcgtc aaattgattg gcagttgtac   1440
ttgtgtaaaa ttcatttgcg tggtctgaac cgttacgctt tgaaggaacg taaactgtat   1500
tcttcgcgtg ctgctgatac tgacgataaa accgcctaa                          1539
```

<210> SEQ ID NO 37
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 37

```
Met Ala Thr Gln Gln Gln Asn Asn Gly Ala Ser Ala Ser Gly Val Leu
1               5                   10                  15

Glu Ile Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45
```

```
Gly Gly Ile His Leu Leu Ile Arg Gly Asn Lys Arg His Pro Ala Ala
         50                  55                  60
Arg Glu Arg Phe Leu Asn Glu Ile Ala Ser Ser Val Phe Glu Arg
 65                  70                  75                  80
Leu Arg His Asp Asp Asn Glu Ala Phe Glu Thr Phe Leu Glu Arg
                     85                  90                  95
Val His Cys Ile Thr Gly Glu Ile Thr Glu Ser Arg Phe Gly Leu Thr
                100                 105                 110
Pro Glu Arg Phe Arg Ala Leu Ala Gly Gln Val Asp Ala Phe Ile His
             115                 120                 125
Ser Ala Ala Ser Val Asn Phe Arg Glu Gln Leu Asp Lys Ala Leu Lys
130                 135                 140
Ile Asn Thr Leu Cys Leu Glu Asn Val Ala Ala Leu Ala Glu Leu Asn
145                 150                 155                 160
Ser Ala Met Ala Val Ile Gln Val Ser Thr Cys Tyr Val Asn Gly Lys
                165                 170                 175
Thr Ser Gly Gln Ile Thr Glu Ser Val Ile Lys Ser Ala Gly Glu Ser
             180                 185                 190
Ile Pro Arg Ser Thr Asp Gly Tyr Tyr Glu Ile Glu Glu Leu Val His
             195                 200                 205
Leu Leu Gln Asp Lys Ile Ser Asp Val Lys Ala Arg Tyr Ser Gly Arg
210                 215                 220
Val Met Gly Lys Lys Leu Val Asp Leu Gly Ile Arg Glu Ala Asn Asn
225                 230                 235                 240
Tyr Gly Trp Ser Asp Thr Tyr Thr Phe Thr Lys Trp Leu Gly Glu Gln
                245                 250                 255
Leu Leu Met Lys Ala Leu Ser Gly Arg Ser Leu Thr Ile Val Arg Pro
             260                 265                 270
Ser Ile Ile Glu Ser Ala Leu Glu Glu Pro Ser Pro Gly Trp Ile Glu
             275                 280                 285
Gly Val Lys Val Ala Asp Ala Ile Ile Leu Ala Tyr Ala Arg Glu Lys
             290                 295                 300
Val Ser Leu Phe Pro Gly Lys Arg Ser Gly Ile Ile Asp Val Ile Pro
305                 310                 315                 320
Val Asp Leu Val Ala Asn Ser Ile Ile Leu Ser Leu Ala Glu Ala Leu
                325                 330                 335
Ser Gly Ser Gly Gln Arg Arg Ile Tyr Gln Cys Cys Ser Gly Gly Ser
             340                 345                 350
Asn Pro Ile Ser Leu Gly Lys Phe Ile Asp Tyr Leu Asn Ala Glu Ala
             355                 360                 365
Lys Thr Asn Tyr Ala Ala Tyr Asp Gln Leu Phe Tyr Arg Arg Pro Thr
370                 375                 380
Lys Pro Phe Val Ala Val Asn Arg Lys Leu Phe Asp Val Val Gly
385                 390                 395                 400
Val Met Arg Val Val Leu Ser Ile Ala Arg Lys Ala Met Arg Leu Ala
                405                 410                 415
Gly Val Asn Arg Glu Leu Lys Val Leu Lys Asn Leu Asp Thr Thr Arg
             420                 425                 430
Lys Leu Ala Thr Ile Phe Gly Phe Tyr Thr Ala Pro Asp Tyr Ile Phe
             435                 440                 445
Arg Asn Asp Ser Leu Met Ala Leu Ala Gln Arg Met Gly Glu Leu Asp
450                 455                 460
Arg Val Leu Phe Pro Val Asp Ala Arg Gln Ile Asp Trp Gln Leu Tyr
```

Leu Cys Lys Ile His Leu Arg Gly Leu Asn Arg Tyr Ala Leu Lys Glu
465                 470                 475                 480
                485                 490                 495

Arg Lys Leu Tyr Ser Ser Arg Ala Ala Asp Thr Asp Lys Thr Ala
                500                 505                 510

<210> SEQ ID NO 38
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 38

| | | | | | |
|---|---|---|---|---|---|
| atggcgactt | atcaacgtaa | caacggtgca | tctgcatccg | gcgtcttgga | aattcttcgt | 60 |
| ggaaagcacg | ttcttatcac | aggtactacc | ggattttttgg | gcaaagtggt | tctggaaaag | 120 |
| ttgattcgta | ctgttccgga | tattggaggt | attcatctgc | tgattcgtgg | caataaacgt | 180 |
| catcaggccg | ctcgcgaacg | tttcctgaac | gaaattgcgc | cctcctccgt | cttcgaacgt | 240 |
| ttgcgtcacg | atgataatga | agccttcgag | accttcttgg | aagaacgtgt | tcactgtatt | 300 |
| accggtgaga | ttactgaatc | ccattttggt | ttgacacctg | agcgttttcg | tgctttggcc | 360 |
| ggtcaggttg | acgcttttat | tcatagcgct | gcaagcgtga | actttcgtga | gcaattggat | 420 |
| aaagccctga | aaatcaacac | cttgtgtctt | gaaaatgttg | ctgcacttgc | agaattgaac | 480 |
| tccgctatgg | cggtcattca | ggtttccact | tgttacgtta | acggtaaaac | ctccggtcaa | 540 |
| attaccgaat | ccgtcattaa | atcggctggc | gaatccattc | cccgttccac | tgacggttac | 600 |
| tacgagatcg | aagaattggt | ccatctgttg | caagacaaga | tttccgatgt | taaagctcgt | 660 |
| tactccggcc | gtgttatggg | gaaaaaattg | gttgatttgg | gtattcgtga | ggccaataat | 720 |
| tacggatggt | ccgacaccta | cacattcacc | aaatggttgg | gtgaacaact | gctgatgaag | 780 |
| gccttgtctg | gtcgttcttt | gactattgtg | cgtccctcta | ttattgagtc | cgcttttgaa | 840 |
| gaaccttccc | ctggttggat | cgaaggcgtt | aaagttgccg | atgccattat | cttggcttat | 900 |
| gcccgtgaaa | aagttagcct | gttccctgga | aaacgttccg | gcattctgga | ttttattcct | 960 |
| gtcgatttgg | ttgcgaactc | catcatcttg | tctctggctg | aggcgttgtc | tggttctggt | 1020 |
| caacgtcgta | tttatcaatg | ttgcagcggt | ggttctaatc | cactgtccct | gggtaagttc | 1080 |
| tttgattatt | tgaacgccga | ggctaagacc | aactatgctg | cctacgatca | actgttttat | 1140 |
| cgtcgtccta | ctaaacctt | cgtcgccgtg | aaccgtaaat | tgtttgacgt | tgttgttggt | 1200 |
| gtcatgcgtg | ttgtcctttc | tattgcccat | aaagctatgc | gtttggctgg | tgtaaatcgt | 1260 |
| gagttgaaag | tgcttaagaa | ccttgatacg | acccgtaaac | ttgcaaccat | ttttggcttc | 1320 |
| tatactgctc | ccgactatat | cttccgtaac | gatagcttga | tggccctggc | tcagcgtatg | 1380 |
| ggtgaattgg | atcgtgttct | tttcccagtt | gatgctcgtc | aaattgattg | gcagttgtac | 1440 |
| ttgtgtaaaa | ttcatttgcg | tggtctgaac | cgttacgctt | tgaagggccg | taaactgtat | 1500 |
| tcttcgcgtg | ctgctgatca | tgacgatgaa | attgcctaa | | | 1539 |

<210> SEQ ID NO 39
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 39

```
Met Ala Thr Tyr Gln Arg Asn Asn Gly Ala Ser Ala Ser Gly Val Leu
1               5                   10                  15

Glu Ile Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
            35                  40                  45

Gly Gly Ile His Leu Leu Ile Arg Gly Asn Lys Arg His Gln Ala Ala
        50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Ile Thr Glu Ser His Phe Gly Leu Thr
                100                 105                 110

Pro Glu Arg Phe Arg Ala Leu Ala Gly Gln Val Asp Ala Phe Ile His
            115                 120                 125

Ser Ala Ala Ser Val Asn Phe Arg Glu Gln Leu Asp Lys Ala Leu Lys
130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Thr Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Arg
210                 215                 220

Val Met Gly Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Leu Asp Phe Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Leu Ser Leu Gly Lys Phe Phe Asp Tyr Leu Asn Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Val Met Arg Val Val Leu Ser Ile Ala His Lys Ala Met Arg Leu Ala
                405                 410                 415
```

```
Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Arg Gly Leu Asn Arg Tyr Ala Leu Lys Gly
                485                 490                 495

Arg Lys Leu Tyr Ser Ser Arg Ala Ala Asp His Asp Asp Glu Ile Ala
            500                 505                 510

<210> SEQ ID NO 40
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 40
acgttatcat tcactttaca tcagagatat accaatggcg attccgggga tccgtcgacc    60

<210> SEQ ID NO 41
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 41
agagaaatta gaaacggaag gttgcggttg caacgacctg tgtaggctgg agctgcttcg    60

<210> SEQ ID NO 42
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: A at position 1 is modified at 5' terminal by
      A*G*A*G* wherein the asterisk symbol represents a phosphorothioate
      bond

<400> SEQUENCE: 42
aaattagaaa cggaaggttg cggttgcaac gacctgcgcc attggtatat ctctgatgta    60
aagtgaatga taacgt                                                   76

<210> SEQ ID NO 43
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 43
agcttaaatg tgattcaaca tcactggaga aagtcttatg attccgggga tccgtcgacc    60

<210> SEQ ID NO 44
<211> LENGTH: 60
<212> TYPE: DNA
<213> ORGANISM: Artificial Sequence
```

<220> FEATURE:
<223> OTHER INFORMATION: Synthetic polynucleotide

<400> SEQUENCE: 44
atgcagggga gcggcaagat taaaccagtt cgttcgggca tgtaggctgg agctgcttcg     60

<210> SEQ ID NO 45
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: T at position 1 is modified at 5' terminal by
      A*G*C*T* wherein the asterisk symbol represents a phosphorothioate
      bond

<400> SEQUENCE: 45
taaatgtgat tcaacatcac tggagaaagt cttatgtgcc cgaacgaact ggtttaatct     60
tgccgctccc ctgcat                                                    76

<210> SEQ ID NO 46
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 46
atttactaaa aaagtttaac attatcagga gagcattatg attccgggga tccgtcgacc     60

<210> SEQ ID NO 47
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 47
tgccagacag cgctactgat taagcggatt ttttcgcttt tgtaggctgg agctgcttcg     60

<210> SEQ ID NO 48
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: A at position 1 is modified at 5' terminal by
      A*T*T*T* wherein the asterisk symbol represents a phosphorothioate
      bond

<400> SEQUENCE: 48
actaaaaaag tttaacatta tcaggagagc attatgaaag cgaaaaaatc cgcttaatca     60
gtagcgctgt ctggca                                                    76

<210> SEQ ID NO 49
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 49
aggataatta ctctgccaaa gtgataaata aacaatgatg attccgggga tccgtcgacc    60

<210> SEQ ID NO 50
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 50
gcaatctaaa gttaatcttc tccacattaa caatatggtg tgtaggctgg agctgcttcg    60

<210> SEQ ID NO 51
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: T at position 1 is modified at 5' terminal by
      G*C*A*A* wherein the asterisk symbol represents a phosphorothioate
      bond

<400> SEQUENCE: 51
tctaaagtta atcttctcca cattaacaat atggtgcatc attgtttatt tatcactttg    60
gcagagtaat tatcct                                                    76

<210> SEQ ID NO 52
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 52
taaaccatgg cgactcaaca acagaaca                                       28

<210> SEQ ID NO 53
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 53
ctatgtcgac ttaggcggtt ttatcgtcag tatca                               35

<210> SEQ ID NO 54
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 54
ccggaattat cgattaactt tattattaaa aattaaagga ggaataaacc atggcgactc    60
aacaacagaa c                                                         71

<210> SEQ ID NO 55
<211> LENGTH: 54
<212> TYPE: DNA
<213> ORGANISM: Artificial Sequence

```
<220> FEATURE:
<223> OTHER INFORMATION: Synthetic polynucleotide

<400> SEQUENCE: 55
ctatgactgc tattttggcg gattcagctg ttcctcctta tttggtactg gaat        54

<210> SEQ ID NO 56
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 56
accgcctaag tcgacaagga ggaataaacc atgaccttag agtggaaacc aaaa        54

<210> SEQ ID NO 57
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 57
ggctcggcgc ccatattttc ctctatatgt atacttcttc caaaccg               47

<210> SEQ ID NO 58
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 58
cgagccgcgg gtataaaagg agatatacat atgaagaagg tttggcttaa ccg         53

<210> SEQ ID NO 59
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 59
gtttcacctg ttatttcgga ttacttctag atcttgaatg agccttcgaa gaatt       55

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
acaatctgtg tgggcactcg                                              20

<210> SEQ ID NO 61
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 61
tcatggttta ttcctccttg tcgacttagg caatttcatc gtcatgatca             50
```

<210> SEQ ID NO 62
<211> LENGTH: 4036
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1223)..(1225)
<223> OTHER INFORMATION: n is a, c, g, or t
<220> FEATURE:
<221> NAME/KEY: misc_feature
<222> LOCATION: (2841)..(2841)
<223> OTHER INFORMATION: n is a, c, g, or t
<220> FEATURE:
<221> NAME/KEY: misc_feature
<222> LOCATION: (2844)..(2845)
<223> OTHER INFORMATION: n is a, c, g, or t
<220> FEATURE:
<221> NAME/KEY: misc_feature
<222> LOCATION: (2864)..(2864)
<223> OTHER INFORMATION: n is a, c, g, or t
<220> FEATURE:
<221> NAME/KEY: misc_feature
<222> LOCATION: (2867)..(2867)
<223> OTHER INFORMATION: n is a, c, g, or t
<220> FEATURE:
<221> NAME/KEY: misc_feature
<222> LOCATION: (2869)..(2869)
<223> OTHER INFORMATION: n is a, c, g, or t

<400> SEQUENCE: 62

```
tcgagttaat taaggcagtg agcgcaacgc aattaatgtg agttagctca ctcattaggc      60
accccaggct ttacacttta tgcttccggc tcgtatgttg tgtggaattg tgagcggata     120
acaatttcac acaggaaaca gctatgacca tgattacgga ttcactggcc gtcgttttac     180
aatctagagg ccagcctggc cataaggaga tatacatatg agtattcaac atttccgtgt     240
cgcccttatt ccctttttg cggcattttg ccttcctgtt tttgctcacc cagaaacgct     300
ggtgaaagta aaagatgctg aagatcagtt gggtgcacga gtgggttaca tcgaactgga     360
tctcaacagc ggtaagatcc ttgagagttt cgccccgaa gagcgttttc caatgatgag     420
cacttttaaa gttctgctat gtggcgcggt attatcccgt gttgacgccg ggcaagagca     480
actcggtcgc cgcatacact attctcagaa tgacttggtt gagtactcac cagtcacaga     540
aaagcatctt acggatggca tgacagtaag agaattatgc agtgctgcca taaccatgag     600
tgataacact gcggccaact tacttctgac aacgatcgga ggaccgaagg agctaaccgt     660
tttttgcac accatggggg atcatgtaac tcgccttgat cgttgggaac cggagctgaa     720
tgaagccata ccaaacgacg agcgtgacac cacgatgcct acagcaatgg caacaacgtt     780
gcgcaaacta ttaactggcg aactacttac tctagcttcc cggcaacaat taatagactg     840
gatggaggcg gataaagttg caggaccact tctgcgctcg gcccttccgg ctggctggtt     900
tattgctgat aaatctggag ccggtgagcg tgggtctcgc ggtatcattg cagcactggg     960
gccagatggt aagccctccc gtatcgtagt tatctacacg acggggagtc aggcaactat    1020
ggatgaacga aatagacaga tcgctgagat aggtgcctca ctgattaagc attggggcca    1080
aactggccac catcaccatc accattaggg aagagcagat gggcaagctt gacctgtgaa    1140
gtgaaaaatg gcgcacattg tgcgacattt ttttttgaat tctacgtaaa aagcagccga    1200
tacatcggct gcttttttt tgnnngaggt tccaacttgt ggtataatga aataagatca    1260
ctccggagcg tatttttga gttatcgaga ttttcaggag ctaaggagga actaaaatgg    1320
agaaaaaaat cactggatat accaccgttg atatatccca atggcatcgt aaagaacatt    1380
```

```
ttgaggcatt tcagtcagtt gctcaatgta cctataacca gaccgttcag ctggatatta    1440 cggcctttt aaagaccgta aagaaaaata agcacaagtt ttatccggcc tttattcaca    1500
ttcttgcccg cctgatgaat gctcatccgg agttccgtat ggcaatgaaa gacggtgagc    1560
tggtgatatg ggatagtgtt cacccttgtt acaccgtttt ccatgagcaa actgaaacgt    1620
tttcatcgct ctggagtgaa taccacgacg atttccggca gtttctacac atatattcgc    1680
aagatgtggc gtgttacggt gaaaacctgg cctatttccc taaagggttt attgagaata    1740 tgttttcgt ctcagccaat ccctgggtga gtttcaccag ttttgattta acgtggcca    1800 atatggacaa cttcttcgcc cccgttttca ccatgggcaa atattatacg caaggcgaca    1860
aggtgctgat gccgctggcg attcaggttc atcatgccgt ctgtgatggc ttccatgtcg    1920
gcagaatgct taatgaatta caacagtact gcgatgagtg cagggcggg cgtaactgc    1980 aggagctcaa acagcagcct gtattcaggc tgcttttttc gttttggtct gcgcgtaatc    2040
tcttgctctg aaaacgaaaa aaccgccttg cagggcggtt tttcgaaggt tctctgagct    2100
accaactctt tgaaccgagg taactggctt ggaggagcgc agtcaccaaa acttgtcctt    2160
tcagtttagc cttaaccggc gcatgacttc aagactaact cctctaaatc aattaccagt    2220
ggctgctgcc agtggtgctt ttgcatgtct ttccggggttg gactcaagac gatagttacc    2280
ggataaggcg cagcggtcgg actgaacggg gggttcgtgc atacagtcca gcttggagcg    2340
aactgcctac ccggaactga gtgtcaggcg tggaatgaga caaacgcggc cataacagcg    2400
gaatgacacc ggtaaaccga aaggcaggaa caggagagcg cacgagggag ccgccagggg    2460
gaaacgcctg gtatctttat agtcctgtcg ggtttcgcca ccactgattt gagcgtcaga    2520
tttcgtgatg cttgtcaggg gggcggagcc tatggaaaaa cggctttgcc gcggccctct    2580
cacttccctg ttaagtatct tcctggcatc ttccaggaaa tctccgcccc gttcgtaagc    2640
catttccgct cgccgcagtc gaacgaccga gcgtagcgag tcagtgagcg aggaagcgga    2700
atatatcctg tatcacatat tctgctgacg caccggtgca gccttttttc tcctgccaca    2760
tgaagcactt cactgacacc ctcatcagta accaccgct ggtagcggtg ttttttttag    2820
gcctatggcc tttttttttt ntgnnaaacc tttcgcggta tggnatnana gcgcccggaa    2880
gagagtcaat taagagggtg gtgaatgtga aaccagtaac gttatacgat gtcgcagagt    2940
atgccggtgt ctcttatcag accgtttccc gcgtggtgaa ccaggccagc cacgtttctg    3000
cgaaaacgcg ggaaaaagtg gaagcggcga tggcggagct gaattacatt cccaaccgcg    3060
tggcacaaca actggcgggc aaacagtcgt tgctgattgg cgttgccacc tccagtctgg    3120
ccctgcacgc gccgtcgcaa attgtcgcgg cgattaaatc tcgcgccgat caactgggtg    3180
ccagcgtggt ggtgtcgatg gtagaacgaa gcggcgtcga agcctgtaaa gcggcggtgc    3240
acaatcttct cgcgcaacgc gtcagtgggc tgatcattaa ctatccgctg gatgaccagg    3300
atgccattgc tgtggaagct gcctgcacta atgttccggc gttatttctt gatgtctctg    3360
accagacacc catcaacagt attatttttct cccatgaaga cggtacgcga ctgggcgtgg    3420
agcatctggt cgcattgggt caccagcaaa tcgcgctgtt agcgggccca ttaagttctg    3480
tctcggcgcg tctgcgtctg gctggctggc ataaatatct cactcgcaat caaattcagc    3540
cgatagcgga acgggaaggc gactggagtg ccatgtccgg ttttcaacaa accatgcaaa    3600
tgctgaatga gggcatcgtt cccactgcga tgctggttgc caacgatcag atggcgctgg    3660
gcgcaatgcg cgccattacc gagtccgggc tgcgcgttgg tgcggacatc tcggtagtgg    3720
```

-continued

| | | | | |
|---|---|---|---|---|
| gatacgacga | taccgaagac | agctcatgtt | atatcccgcc | gttaaccacc atcaaacagg | 3780 |
| attttcgcct | gctggggcaa | accagcgtgg | accgcttgct | gcaactctct cagggccagg | 3840 |
| cggtgaaggg | caatcagctg | ttgcccgtct | cactggtgaa | aagaaaaacc accctggcgc | 3900 |
| ccaatacgca | aaccgcctct | ccccgcgcgt | tggccgattc | attaatgcag ctggcacgac | 3960 |
| aggtttcccg | actggaaagc | gggcagtgag | cggtacccga | taaaagcggc ttcctgacag | 4020 |
| gaggccgttt | tgtttc | | | | 4036 |

What is claimed is:

1. An expression vector comprising the recombinant polynucleotide sequence of SEQ ID NO:16.

2. The expression vector of claim 1, wherein said vector further comprises a gene of interest.

3. An expression vector comprising the recombinant polynucleotide sequence of SEQ ID NO:62.

4. The expression vector of claim 3, wherein said vector further comprises a gene of interest.

5. A host cell comprising the expression vector of claim 1.

6. A host cell comprising the expression vector of claim 3.

7. A recombinant polynucleotide sequence comprising SEQ ID NO:16.

8. A recombinant polynucleotide sequence comprising SEQ ID NO:62.

* * * * *